US007968334B2

(12) United States Patent
Puttaraju et al.

(10) Patent No.: US 7,968,334 B2
(45) Date of Patent: *Jun. 28, 2011

(54) EXPRESSION OF APOAI AND VARIANTS THEREOF USING SPLICEOSOME MEDIATED RNA TRANS-SPLICING

(75) Inventors: Madaiah Puttaraju, Germantown, MD (US); Edward Otto, Reston, VA (US); Mariano A. Garcia-Blanco, Durham, NC (US); Gerard J. McGarrity, Gaithersburg, MD (US); Gary F. Temple, Washington Grove, MD (US)

(73) Assignee: VIRxSYS Corporation, Gaitherburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/141,447

(22) Filed: May 31, 2005

(65) Prior Publication Data
US 2006/0194317 A1    Aug. 31, 2006

Related U.S. Application Data

(63) Continuation-in-part of application No. 11/041,155, filed on Jan. 21, 2005, which is a continuation-in-part of application No. PCT/US2005/002392, filed on Jan. 21, 2005.

(60) Provisional application No. 60/538,796, filed on Jan. 23, 2004, provisional application No. 60/584,280, filed on Jun. 30, 2004.

(51) Int. Cl.
C12N 5/00 (2006.01)
C12N 15/12 (2006.01)
C12N 15/63 (2006.01)
C12N 15/87 (2006.01)

(52) U.S. Cl. .......................... 435/325; 435/455; 435/463
(58) Field of Classification Search .................. None
See application file for complete search history.

(56) References Cited

U.S. PATENT DOCUMENTS

| 4,980,286 | A | 12/1990 | Morgan et al. |
| 5,354,678 | A | 10/1994 | Lebkowski et al. |
| 5,585,362 | A | 12/1996 | Wilson et al. |
| 5,589,377 | A | 12/1996 | Lebkowski et al. |
| 5,616,326 | A | 4/1997 | Spibey |
| 5,670,488 | A | 9/1997 | Gregory et al. |
| 5,700,470 | A | 12/1997 | Saito et al. |
| 5,731,172 | A | 3/1998 | Saito et al. |
| 5,747,072 | A | 5/1998 | Davidson et al. |
| 5,756,283 | A | 5/1998 | Wilson et al. |
| 5,789,390 | A | 8/1998 | Descamps et al. |
| 5,820,868 | A | 10/1998 | Mittal et al. |
| 5,837,484 | A | 11/1998 | Trempe et al. |
| 5,843,742 | A | 12/1998 | Natsoulis et al. |
| 5,851,806 | A | 12/1998 | Kovesdi et al. |
| 5,858,351 | A | 1/1999 | Podsakoff et al. |
| 5,866,551 | A | * 2/1999 | Benoit et al. ........... 514/44 |
| 5,869,037 | A | 2/1999 | Crystal et al. |
| 5,871,982 | A | 2/1999 | Wilson et al. |
| 5,877,011 | A | 3/1999 | Armentano et al. |
| 5,885,808 | A | 3/1999 | Spooner et al. |
| 5,891,690 | A | 4/1999 | Massie |
| 5,919,676 | A | 7/1999 | Graham et al. |
| 5,922,576 | A | 7/1999 | He et al. |
| 5,928,944 | A | 7/1999 | Seth et al. |
| 5,932,210 | A | 8/1999 | Gregory et al. |
| 5,952,221 | A | 9/1999 | Kurtzman et al. |
| 5,962,311 | A | 10/1999 | Wickham et al. |
| 5,962,313 | A | 10/1999 | Podsakoff et al. |
| 5,998,205 | A | 12/1999 | Hallenbeck et al. |
| 6,013,487 | A | 1/2000 | Mitchell |
| 6,083,702 | A | 7/2000 | Mitchell |
| 6,280,978 | B1 | 8/2001 | Mitchell |
| 7,094,399 | B2 | 8/2006 | Otto |
| 7,399,753 | B2 | 7/2008 | Mitchell |
| 2006/0094110 | A1 | 5/2006 | McGarrity |
| 2006/0134658 | A1 | 6/2006 | Garcia-Blanco |
| 2006/0154257 | A1 | 7/2006 | Mitchell |
| 2006/0160182 | A1 | 7/2006 | McGarrity |
| 2006/0172381 | A1 | 8/2006 | McGarrity |
| 2006/0177933 | A1 | 8/2006 | Puttaraju |
| 2006/0234247 | A1 | 10/2006 | Puttaraju |
| 2006/0246422 | A1 | 11/2006 | Mitchell |

FOREIGN PATENT DOCUMENTS

| WO | WO 88/09810 | 12/1988 |
| WO | WO 89/10134 | 11/1989 |
| WO | WO 98/11241 | 3/1998 |
| WO | WO 00/09734 | 2/2000 |

OTHER PUBLICATIONS

Law, S. et al., "Nucleotide sequence and the encoded amino acids of human apolipoprotein A-I mRNA", 1984, PNAS, vol. 81: pp. 66-70.*
U.S. Appl. No. 10/693,192, filed Oct. 23, 2003, "Screening Method for Identification of Efficient Pre-Trans-Splicing Molecules," Mitchell et al.
U.S. Appl. No. 10/434,727, filed May 8, 2003, "Use of Sliceosome Mediated RNA Trans-Splicing to Confer Cell Selective Replication to Adenoviruses," Otto et al.
U.S. Appl. No. 10/374,784, filed Feb. 25, 2003, "Trans-Splicing Mediated Imaging of Gene Expression," Mitchell et al.
U.S. Appl. No. 10/360,787, filed Jun. 5, 2002, "Spliceosome Mediated RNA Trans-Splicing for Correction of Factor VIII Genetic Defects," Mitchell et al.

(Continued)

Primary Examiner — Michael Burkhart
(74) Attorney, Agent, or Firm — VIRxSYS Corporation; Serge Sira, Esq.

(57) ABSTRACT

Methods and compositions for generating novel nucleic acid molecules through targeted spliceosome mediated RNA trans-splicing that result in expression of a apoAI protein, an apoAI variant, the preferred embodiment referred to herein as the apoAI Milano variant, a pre-pro-apoAI or an analogue of apoAI. The methods and compositions include pre-trans-splicing molecules (PTMs) designed to interact with a target precursor messenger RNA molecule (target pre-mRNA) and mediate a trans-splicing reaction resulting in the generation of a novel chimeric RNA molecule (chimeric RNA) capable of encoding apoAI, the apoAI Milano variant, or an analogue of apoAI. The expression of this apoAI protein results in protection against vascular disorders resulting from plaque build up, i.e., atherosclerosis, strokes and heart attacks.

25 Claims, 55 Drawing Sheets

OTHER PUBLICATIONS

Figure 1:
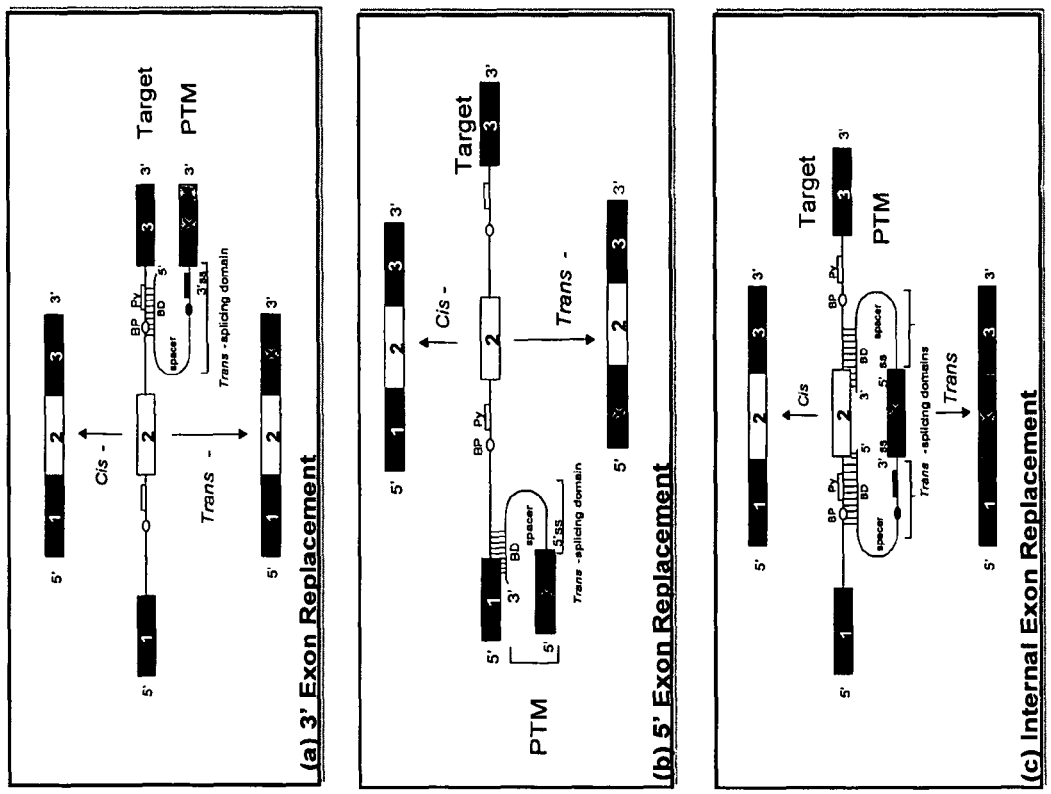

U.S. Appl. No. 10/198,447, filed Jul. 17, 2002, "Spliceosome Mediated RNA Trans-Splicing for Correction of Skin Disorders," Mitchell et al.
U.S. Appl. No. 10/136,723, filed Apr. 30, 2002, "Transgenic Animal Model for Spliceosome-mediated RNA Trans-Splicing," Puttaraju et al.
U.S. Appl. No. 10/103,294, filed Mar. 20, 2002, "Spliceosome Mediated RNA Trans-Splicing," Mitchell et al.
U.S. Appl. No. 10/075,028, filed Feb. 12, 2002, "Methods and Compositions for Use in Spliceosome Mediated RNA Trans-Splicing," Mitchell et al.
U.S. Appl. No. 10/076,248, filed Feb. 12, 2002, "Methods and Compositions for Use in Spliceosome Mediated RNA Trans-Splicing," Mitchell et al.
U.S. Appl. No. 09/838,858, filed Apr. 20, 2001, "Methods and Compositions for Use in Spliceosome Mediated RNA Trans-Splicing," Mansfield et al.
U.S. Appl. No. 09/756,097, filed Jan. 8, 2001, "Methods and Compositions for Use in Spliceosome Mediated RNA Trans-Splicing," Mitchell et al.
U.S. Appl. No. 09/756,095, filed Jan. 8, 2001, "Methods and Compositions for Use in Spliceosome Mediated RNA Trans-Splicing," Mitchell et al.
U.S. Appl. No. 09/756,096, filed Jan. 8, 2001, "Methods and Compositions for Use in Spliceosome Mediated RNA Trans-Splicing," Mitchell et al.
Bhaumik et al., "Molecular Imaging of Gene Expression in Living Subjects by Spliceosome-Mediated RNA Trans-Splicing," Jun. 8, 2004, Proc. Natl. Acad. Sci., 101:23:8693-8698.
Tahara et al., "Trans-Splicing Repair of CD4O-Ligand Deficiency Results in Naturally Regulated Correction of A Mouse Model of Hyper-IgM X-Linked Immunodeficiency," Aug. 2004, Nature Medicine, 10:835-841.
Chao et al., "Phenotype Correction of Hemophilia A Mice by Spliceosome-Mediated RNA Trans-Splicing," Aug. 2003, Nature Medicine, 9:1-5.
Liu et al., "Partial Correction of Endogenous Δ508 CFTR in Human Cystic Fibrosis Airway Epithelia by Spliceosome-Mediated RNA Trans-Splicing," Jan. 2002, Nature Biotechnology, 20:47-52.
Kim et al., "Role of the Nonsense-Mediated Decay Factor hUpf3 in the Splicing Dependent Exon-Exon Junction Complex," Sep. 7, 2001, Science 293:1832-1836.
Kim et al., "Replication-Selective Virotherapy for Cancer:Biological Principles, Risk Management and Future Directions," Jul. 2001, Nat. Med. 7:781-787.
Tian et al., "Strong RNA Splicing Enhancers Identified by a Modified Method of Cycled Selection Interact with SR Protein," Sep. 7, 2001, J. Biological Chemistry 276:33833-33839.
Mansfield et al., "Repair of CFTR mRNA by Splicesome-Mediated RNA Trans-Splicing," Jul. 28, 2000, Gene Therapy 7:1885-1895.
Tacke et al., "Determinants of SR Protein Specificity," 1999, Curr. Opin. Cell Biol. 11:358-362.
He et al. "A Simplified System for Generating Recombinant Adenoviruses," Mar. 1998, Proc. Natl. Acad. Sci., 95, 2509-2514.
Lan et al., "Ribozyme-Mediated Repair of Sickle β-Globin mRNAs in Erythrocyte Precursors" Jun. 5, 1998, Science 280:1593-1596.
Phylactou et al., "Ribozyme-Mediated Trans-Splicing of a Trinucleotide Repeat" Apr. 1998, Nature Genetics 18:378-381.
Staley et al., "Mechanical Devices of the Spliceosome: Motors, Clocks, Springs and Things," 1998, Cell 92:315-326.
Bellet et al., "Malignant Transformation of Nontrophoblastic Cells is Associated With the Expression of Chorionic Gonadotropin β Genes Normally Transcribed Introphoblastic Cells," Feb. 1, 1997, Cancer Res. 57:516-523.
Coolidge et al., "Functional Analysis of the Polypyrimidine Tract in Pre-mRNA Splicing," 1997, Nucleic Acids Res. 25:888-896.
Crouzet et al. "Recombinational Construction in *Escherichia coli* of Infectious Adenoviral Genomes," Feb. 1997, Proc. Natl. Acad. Sci., 94, 1414-1419.
Good et al., "Expression of Small, Therapeutic RNAs in Human Cell Nuclei," 1997, Gene Ther. 4:45-54.

Malek et al., "Evolution of Trans-Splicing Plant Mitochondrial Introns in Pre-Permian Times," Jan. 1997, Proc. Nat'l. Acad. Sci., 94:553-558.
Chartier, et al., "Efficient Generation of Recombinant Adenovirus Vectors by Homologous Recombination in *Escherichia coli*," Jul. 1996, Virol. 70, 4805-4810.
Hoon et al., "Detection of Metastatic Breast Cancer by β-hCG Polymerase Chain Reaction," 1996, Int J. Cancer 69:369-374.
Jones et al., "Tagging Ribozyme Reaction Sites to Follow Trans-Splicing in Mammalian Cells," Jun. 1996, Nature Medicine 2:643-648.
Krämer A., "The Structure and Function of Proteins Involved in Mammalian Pre-mRNA Splicing," 1996, Annu. Rev. Biochem. 65:367-409.
Miyake et al. "Efficient Generation of Recombinant Adenoviruses Using Adenovirus DNA-Terminal Protein Complex and A Cosmid Bearing the Full-Length Virus Genome," Feb. 1996, Proc. Natl. Acad. Sci., 93, 1320-1324.
Nilsson et al., "Multiple Affinity Domains for the Detection, Purification, and Immobilization of Recombinant Proteins," 1996, J. Mol. Recognition, 9:585-594.
Pasman et al., "The 5' and 3' Splice Sites Come Together Via a Three Dimensional Diffusion Mechanism," 1996, Nucleic Acids Res. 24(9):1638-1645.
Boelens et al., "Nuclear Retention of RNA as a Mechanism for Localization" 1995, RNA 1:273-283.
Bruzik et al., "Enhancer-Dependent Interaction Between 5' and 3' Splice Sites in Trans," 1995, Proc. Nat'l. Acad. Sci., 92:7056-7059.
Chiara et al., "A Two-Step Mechanism for 5' and 3' Splice-Site Pairing," Jun. 1995, Nature 375:510-513.
Davis et al., "RNA Trans-Splicing in Flatworms," Sep. 15, 1995, J. Biol. Chem. 270:21813-21819.
Eul et al., "Experimental Evidence for RNA Trans-Splicing in Mammalian Cells," 1995, EMBO. J. 14(13):3226-3235.
Xiang-Dong Fu, "The Superfamily of Arginine/Serine-Rich Splicing Factors," 1995, RNA 1:663-680.
Bett et al. "An Efficient and Flexible System for Construction of Adenovirus Vectors with Insertions or Deletions in Early Regions 1 and 3," Sep. 1994, Proc. Natl. Acad. Sci., 91,8802-8806.
Hollenberg et al., "Multiple Promoter Elements in the Human Chorionic Gonadotropin B Subunit Genes Distinguish their Expression from Luteinizing Hormone β Gene," 1994, Mol. Cell Endo., 106:111-119.
Ketner et al. "Efficient Manipulation of the Human Adenovirus Genome as an Infectious Yeast Artificial Chromosome Clone," Jun. 1994, Proc. Natl. Acad. Sci., 91, 6186-6190.
Sullenger et al., "Ribozyme-Mediated Repair of Defective mRNA by Targeted Trans-Splicing," Oct. 1994, Nature 371:619-622.
Goldspiel et al., "Human Gene Therapy," Jul. 1993, Clinical Pharmacy 12:488-505.
Kozarsky and Wilson et al., "Gene Therapy: Adenovirus Vectors," 1993, Current Opinion in Genetics and Development 3:499-503.
Miller and Rosman, "Use of Retroviral Vectors for Gene Transfer and Expression," 1993, Meth. Enzymol. 217:581-599.
Moore and Sharp, "Evidence for Two Active Sites in The Splicesome Provided by Stereochemistry of Pre-mRNA Splicing," Sep. 23, 1993, The Nature, 365:364-368.
Moore et al, "Splicing of Precursors to mRNA by The Spliceosome," 1993, RNA World, 303-357.
Morgan and Anderson, "Human Gene Therapy," 1993, Ann. Rev. Biochem. 62:191-217.
Mulligan, Richard C., "The Basic Science of Gene Therapy," May 14, 1993, Science 260:926-932.
Roscigno et al., "A Mutational Analysis of the Polypyrimidine Tract of Introns," May 25, 1993, J. Bio. Chem., 268:11222-11229.
Tolstoshev, Paul, "Gene Therapy, Concepts, Current Trials, and Future Directions," 1993, Ann. Rev. Pharmacol. Toxicol. 33:573-596.
Acevedo et al., "Human Chorionic Gonadotropin-Beta Subunit Gene Expression in Cultured Human Fetal and Cancer Cells of Different Types and Origins," Oct. 15, 1995, Cancer 76:1467-1475.
Bruzik et al., "Spliced Leader RNAs from Lower Eukaryotes are Trans-spliced in Mammalian Cells," Dec. 1992, Nature 360:692-695.

Vellard et al., "A Potential Splicing Factor is Encoded by the Opposite Strand of the Trans-Spliced C-myb Exon," 1992, Proc. Nat'l. Acad. Sci., 89:2511-2515.

Dingwall and Laskey, "Nuclear Targeting Sequences—A Consensus?" Dec. 1991, Trends in Biochem. Sci., 16:478-481.

Ghattas et al., "The Encephalomyocarditis Virus Internal Ribosome Entry Site Allows Efficient Coexpression of Two Genes from a Recombinant Provirus in Culture Cells and in Embryos," Dec. 1991, Mol. Cell Biol. 11:5848-5859.

Jankrecht et al., "Rapid and Efficient Purification of Native Histidine-Tagged Protein Expressed by Recombinant Vaccinia Virus," Jul. 8, 1991, Proc. Natl. Acad. Sci., 88:8972-8976.

Rosenfeld et al. "Adenovirus-Mediated Transfer of a Recombinant $\alpha_{-1}$ Antitrypsin Gene to the Lung Epithelium in Vivo," Apr. 19, 1991, Science, 252, 431-4.

Wu and Wu, "Delivery Systems for Gene Therapy," 1991, Biotherapy 3:87-95.

Gilardi et al. "Expression of Human $\alpha_{-1}$-Anti-trypsin Using a Recombinant Adenovirus Vector," 1990, EBS Lett. 267, 60-62.

Rajkovic et al., "A Spliced Leader is Present on a Subset of mRNAs from the Human Parasite Schistosoma Mansoni" Nov. 1990, Proc. Nat'l. Acad. Sci., 87:8879-8883.

Schneider and Banes, "Building Blocks for Oligonucleotide Analogs with Dimethylene-Sulfide-Sulfoxide and Sulfone Groups Replacing Phosphodiester Linkages," 1990, Tet. Letters, 31:335-338.

Senapathy et al., "Splice Junctions, Branch Point Sites, and Exons:Sequence Statistics, Identification, and Applications to Genome Project," 1990, Methods in Enzymology, 183:252-278.

Uhlmann and Peyman, "Antisense Oligonucleotides: A New Therapeutic Principle," Jun. 1990, Chemical Reviews, 90:543-584.

Kerem et al., "Identification of the Cystic Fibrosis Gene: Genetic Analysis," Sep. 8, 1989, Science, 245:1073-1080.

Letsinger et al., "Cholesteryl-Conjugated Oligonucleotide: Synthesis, Properties, and Activity as Inhibitors of Replication of Human Immunodeficiency Virus in Cell Culture," Sep. 1989, Proc. Natl. Acad. Sci., 86:6553-6556.

Reed, Robin, "The Organization of 3' Splice Sites Sequences in Mammalian Introns," 1989, Genes Dev. 3:2113-2123.

Riordan et al., "Identification of the Cystic Fibrosis Gene: Cloning and Characterization of Complementary DNA," 1989, Science, 245:1066-1073.

Rommens et al., "Identification of the Cystic Fibrosis Gene: Chromosome Walking and Jumping," Sep. 8, 1989, Science, 245:1059-1065.

Shimizu et al., "Immunoglobulin Double-Isotype Expression by Trans-mRNA In a Human Immunoglobulin Transgenic Mouse," Oct. 1989, Proc. Nat'l. Acad. Sci. 86:8020-8023.

Smith et al., "Scanning From an Independently Specified Branch Point Defines the 3' Splice Site of Mammalian Introns," 1989, Nature, 342:243-247.

Van der Krol et al., "Modulation of Eukaryotic Gene Expression by Complementary RNA or DNA Sequences," 1988, BioTechniques, 6:958-976.

Reed & Maniatis, "The Role of The Mammalian Branchpoint Sequence In the Pre-mRNA Splicing," 1988, Genes Dev. 2:1268.

Smith et al, "Single-Step Purification of Polypeptides Expressed in *Escherichia coli* as Fusions with Glutathione S-Transferase," 1988, Gene, 67:31.

Zon et al., "Oligonucleotide Analogues as Potential Chemotherapeutic Agents," 1988, Pharm. Res., 5:539-549.

Krause M et al., "A Trans-Spliced Leader Sequence on Actin mRNA in C. Elegans," 1987, Cell 49:753-761.

Lemaitre et al., "Specific Antiviral Activity of a Poly(L-lysine)-Conjugated Oligodeoxyribonucleotide Sequence Complementary to Vesicular Stomatitis Virus N Protein mRNA Initiation Site," 1987, Proc. Natl. Acad. Sci., 84:648-652.

Wu and Wu, "Receptor-Mediated in Vitro Gene Transformation by a Soluble DNA Carrier System," 1987, J. Biol. Chem., 262:429-4432.

Dingwall and Laskey, "Protein Import into the Cell Nucleus," 1986, Ann. Rev. Cell Biol. 2:367-390.

Murphy et al., "Identification of a Novel Y Branch Structure as an Intermediate in Trypanosome mRNA Processing: Evidence for Trans Splicing," 1986, Cell, 47:517.

Smith et al., "$M_r$ 26,000 Antigen of Schistosoma Japonicum Recognized by Resistant WEH1 129/J Mice is a Parasite Glutathione S-Transferase," 1986, Proc. Natl. Acad. Sci., 83:8703-8707.

Sutton et al., "Evidence for Trans Splicing in Trypanosomes," 1986, Cell 47:527-535.

Konarska et al., "Trans Splicing of mRNA Precursors In Vitro" 1985, Cell 46:165-171.

Solnick et al, "Trans Splicing of mRNA Precursors," 1985, Cell 42:157-164.

Talmadge et al., "Only Three of the Seven Human Chorionic Gonadotropin Beta Subunit Genes can be Expressed in the Placenta," 1984, Nucleic Acids Res. 12:8415.

Accession No. K01722, Corynebacteriophage beta diptheria toxin (DT) gene, Apr. 27, 1993.

Berkner, et al. "Generation of Adenovirus by Transfection of Plasmids," 1983, Nucleic Acids Res. 11, 6003-6020.

Greenfield, "Nucleotide Sequence of the Structural Gene for the Diptheria Toxin Carried by Corynebacteriophage β," 1983, Proc. Natl. Acad. Sci., 80:6853-6857.

Brinster et al., "Regulation of Metallothionein-Thymidine Kinase Fusion Plasmids Injected into Mouse Eggs," 1982, Nature 296:39-42.

Benoist et al., "In Vivo Sequence Requirements of the SV40 Early Promoter Region," 1981, Nature, 290:304-310.

Wagner et al., "Nucleotide Sequence of the Thymidine Kinase Gene of Herpes Simplex Virus Type 1," Mar. 1981, Proc. Natl. Acad. Sci., 78(3):1441-1445.

Yamamoto et al., "Identification of a Functional Promoter in the Long Terminal Repeat of Rous Sarcoma Virus," 1980, Cell, 22:787-797.

Berget et al., Spliced Segments at the 5' Terminus of Adenovirus 2 Late mRNA, 1977, Proc. Natl. Acad. Sci., 74(8):3171-3175.

Chow et al., "An Amazing Sequence Arrangement at the 5' Ends of Adenovirus 2 Messenger RNA," 1977, Cell 12:1-8.

Graham et al., "Characteristics of a Human Cell Line Transformed by DNA from Human Adenovirus Type 5," 1977, J. Gen. Virol. 36:59-72.

Uchida et al, "Diptheria Toxin and Related Proteins: Isolation and Properties of Mutant Proteins Related to Diptheria Toxin," 1973 J. Biol. Chem., 248:3838.

Puttaraju et al., Spliceosome-Mediated RNA Trans-Splicing as a Tool for Gene Therapy, Nat. Biotech., 1999, vol. 17, 246-252.

Voss et al., "Efficiency Assessment of the Gene Trap Approach", 1998, Development Dynamics, 212:171-180.

Puttaraju et al., "Messenger RNA Repair and Restoration of Protein Function by Spliceosome-Mediated mRNA Trans-Splicing", Mol. Therapy, 2001, vol. 4, 105-114.

Song et al., "Intramuscular Administration of Recombinant Adeno-Associated Virus 2 α-1 Antitrypsin (rAAV-SERPINA1) Vectors in a Nonhuman Primate Model: Safety and Immunologic Aspects", Sep. 3, 2002, Molecular Therapy 6:329-335.

Garcia-Blanco et al, "Spliceosome-Mediated RNA trans-Splicing in Gene Therapy and Genomics," Apr. 20, 200, Gene Therapy and Regulation, 1:141-163.

Garcia-Blanco et al "Mending the Message", Nat. Biotech., 2003, vol. 21, No. 12, 1448-1449.

Liu et al., "Spliceosome-Mediated RNA trans-Splicing with Recombinant Adeno-Associated Virus Partially Restores Cystic Fibrosis Transmembrane Conductance Regulator Function to Polarized Human Cystic Fibrosis Airway Epithelial Cells," Sep. 2005 *Human Gene Therapy* 16:1116-1123.

Mansfield, et al. "5' Exon Replacement and Repair by Spliceosome-Mediated RNA trans-Splicing", RNA, 2003, vol. 9, 1290-1297.

Mansfield, et al., Repair of CFTR mRNA by Spliceosome-Mediated RNA Trans-Splicing, Gene Therapy, 2000, vol. 7, 1885-1895.

Manzano, et al., "Failure to Generate Atheroprotective Apolipoprotein A1 Phenotypes Using Synthetic RNA/DNA Oligonucleotides (chimeraplasts)", J. Gene Med., 2003, vol. 5, 795-802.

Parolini, et al., "Targeted Replacement of Mouse Apolipoprotein A-I with Human ApoA-I or the Mutant ApoA-I", J. Bio. Chem., 2003, vol. 278, 4740-4746.

Martinez-Sales, E., Internal Ribosome Entry Site Biology and Its Use in Expression Vectors, 1999, Current Opinion in Biology, 10:458-464.

Kikumori et al., "Promiscuity of Pre-mRNA Spliceosome-Meidated Trans Splicing: A Problem for Gene Therapy?," Jul. 20, 2001, Human Gene Therapy, 12:1429-1441.

U.S. Appl. No. 09/941,492, filed Aug. 29, 2001, "Methods and Compositions for Use in Spliceosome Mediated RNA Trans-Splicing," Mitchell et al.

U.S. Appl. No. 08/786,531, filed Jan. 21, 1997, "Vehicles for Stable Transfer of Green Fluorescent Protein Gene and Methods of Use for Same," Link. Jr., et al.

* cited by examiner

Nucleotide and amino acid sequences of ApoAI wild type

ApoAI wild type: (SEQ ID NO. 20)

```
AGAGACTGCG AGAAGGAGT CCCCCACGGC CCTTCAGG ATG GCT GCG AAA GCT GCG GTG CTG ACC TTG GCC GTG CTC TTC CTG ACG GGG AGC CAG GCT CGG CAT TTC TGG CAG
                                         m   k   a   a   v   l   t   l   a   v   l   f   l   t   g   s   q   a   r   h   f   w   q

CAA GAT GAA CCC CCC CAG AGC CCC TGG GAT CGA GTG AAG GAC CTG GCC ACT GTG TAC GTG GAT GTC CTC AAA GAC AGC GGC AGA GAC TAT GTG TCC CAG TTT
 q   d   e   p   p   q   s   p   w   d   r   v   k   d   l   a   t   v   y   v   d   v   l   k   d   s   g   r   d   y   v   s   q   f

GAA GGC TCC GCC TTG GGA AAA CAG CTA AAC CTA AAG CTC CTT GAC AAC TGG GAC AGC GTG ACC TCC ACC TTC AGC AAG CTG CGC GAA CAG CTC GGC CCT GTG
 e   g   s   a   l   g   k   q   l   n   l   k   l   l   d   n   w   d   s   v   t   s   t   f   s   k   l   r   e   q   l   g   p   v

ACC CAG GAG TTC TGG GAT AAC CTG GAA AAG GAG ACA GAG GGC CTG AGG CAG GAG ATG AGC AAG GAT CTG GAG GAG GTG AAG GCC AAG GTG CAG CCC TAC CTG
 t   q   e   f   w   d   n   l   e   k   e   t   e   g   l   r   q   e   m   s   k   d   l   e   e   v   k   a   k   v   q   p   y   l

GAC GAC TTC CAG AAG AAG TGG CAG GAG GAG ATG GAG CTC TAC CGC CAG AAG GTG GAG CCG CTG CGC GCA GAG CTC CAA GAG GGC GCG CAG CAG AAG CTG CAC
 d   d   f   q   k   k   w   q   e   e   m   e   l   y   r   q   k   v   e   p   l   r   a   e   l   q   e   g   a   r   q   k   l   h nt 555 (C>T converts Wild type to Milano)
GAG CTG CAA GAG GAG AAG CTG AGC CCA CTG GGT GAA ATG CGC GAC CGC CGC GAC GCG CGC GCC CAT GTG GAC GCC CTG CGC ACG CAT CTG GCC CCC TAC AGC GAC GAG
 e   l   q   e   e   k   l   s   p   l   g   e   e   m   r   d   r   a   r   a   h   v   d   a   l   r   t   h   l   a   p   y   s   d   e CTG CGC CAG CGC TTG GCC GCG CGC CTT GAG GCT CTC AAG GAG AAC GGC GGC GCC AGA CTG GCC GAG TAC CAC GCC AAG GCC ACC GAG CAT CTG AGC ACG CTC
 l   r   q   r   l   a   a   r   l   e   a   l   k   e   n   g   g   a   r   l   a   e   y   h   a   k   a   t   e   h   l   s   t   l AGC GAG AAG GCC AAG CCC GCG CTC GAG GAC CTC CGC CAA GGC TTG CTG CCC GTG CTG GAG AGC TTC AAG GTC AGC TTC CTG AGC GCT CTC GAG GAG TAC ACT
 s   e   k   a   k   p   a   l   e   d   l   r   q   g   l   l   p   v   l   e   s   f   k   v   s   f   l   s   a   l   e   e   y   t AAG AAG CTC AAC ACC CAG TGA GGCGCCCCCCC TTCCCGGTGC TCAGAATAAA CGTTTCCAAA GTGGG
 k   k   l   n   t   q   stop
```

ApoAI-Milano: Molecular analysis have confirmed a Arg → Cys substitution at position 173 amino acid that converts the wild type apoAI into apoAI Milano variant. At the nucleotide level, a single nucleotide substitution C → T was confirmed.

Figure 3A

This apoAI variant shows a single amino acid substitution (Arg → Cys) at position 173, that leads to the formation of homodimers and heterodimers.

Strategy to create ApoAI-Milano

1. PCR amplify apoAI (wt) cDNA from a clone from ATCC (use primers – Apo4 and 5) and digest w/ <u>NheI</u>

Apo4: CTAG GCTAGC AGAGACTGCG AGAAGGAGGT CCCCCACG  (SEQ ID NO. 21)
   Apo5: CTAG AAGCTT CCCACTTGG AAACGTTTAT TCTGAGCACC GG  (SEQ ID NO. 24)

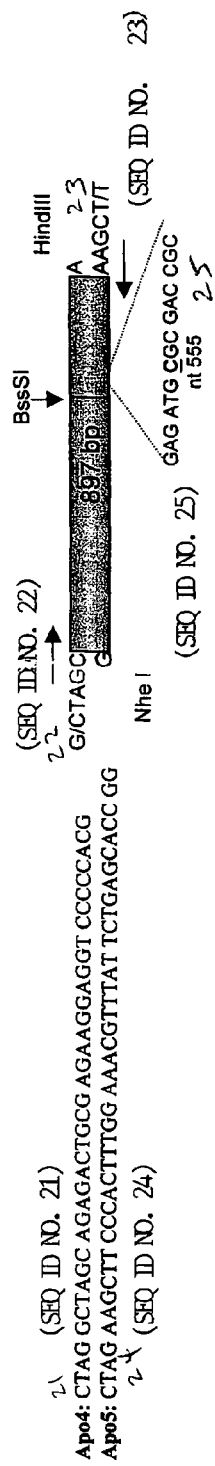

(SEQ ID NO. 22)

(SEQ ID NO. 25) GAG ATG CGC GAC CGC  (SEQ ID NO. 23)
nt 555

2. Digest w/ <u>BssS1</u> → results in 2 fragments (513 bp + 384 bp), gel purify 513bp fragment

1. PCR amplify apoAI milano fragment (3' fragment – 384 bp) using primers Apo5 & 6, wt cDNA as template. The new primers introduces Cys → Arg mutation at position nt 555.

(SEQ ID NO. 26) Apo6: CTAG CACGAGCT GCAAGAGAAG CTGAGCCCAC TGGGCGAGGA GATG<u>T</u>GCGACCGGCGC
Underlined nucleotide indicate C>T mutation to make milano version

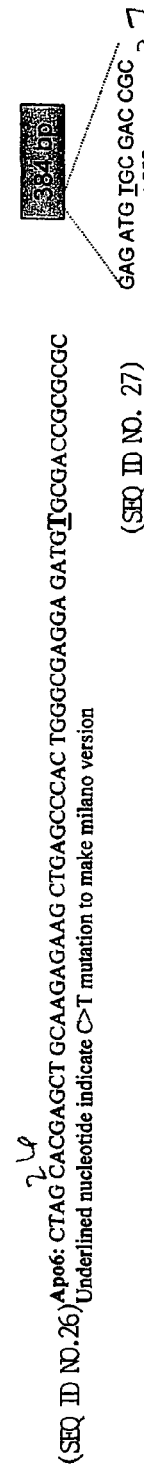

GAG ATG <u>T</u>GC GAC CGC  (SEQ ID NO. 27)
nt 555

2. Digest with BssSI and HindIII, gel purify, ligate two fragments into pcDNA3.1 expression vector 3. Transform and isolate mini-prep DNA. Confirm the intended nucleotide change by sequencing the plasmid DNA.

Figure 3C

Target gene and PTM Structure
**4A. Schematic structure human wild type apoAI full-length target gene for *in vitro* studies:**
4B. Schematic structure of human apoAI-Milano PTM1 (exon 4):
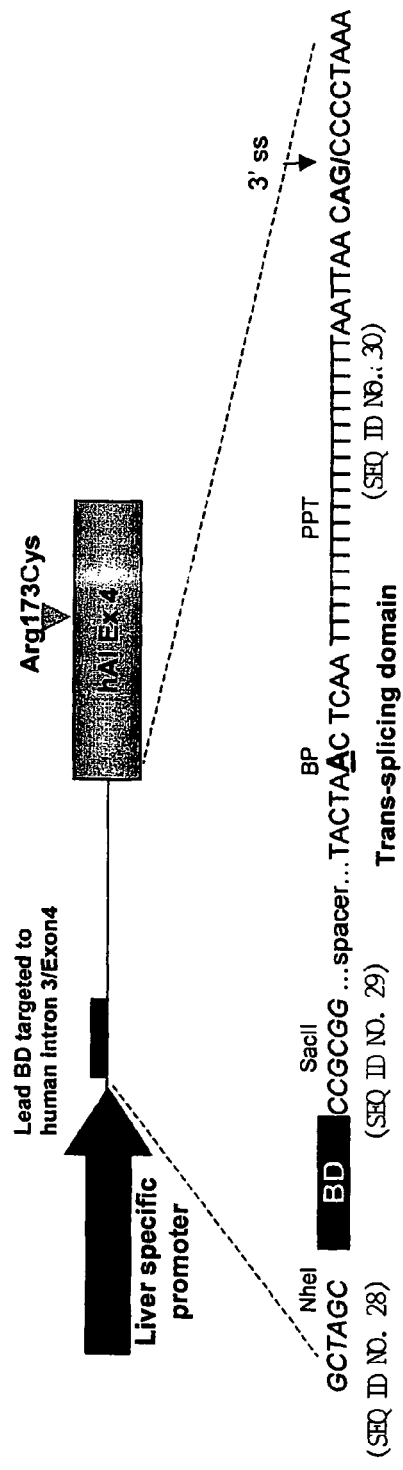
Figure 4A - B

Mini-gene target and PTM Structure
A) <u>Schematic structure human apoB mini-gene target for *in vitro* studies:</u>
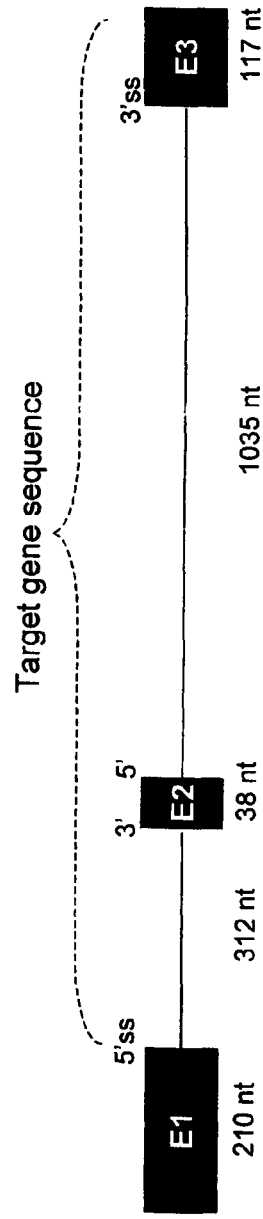
B) <u>Schematic structure of human apoAI-Milano PTM2 (-ATG):</u>
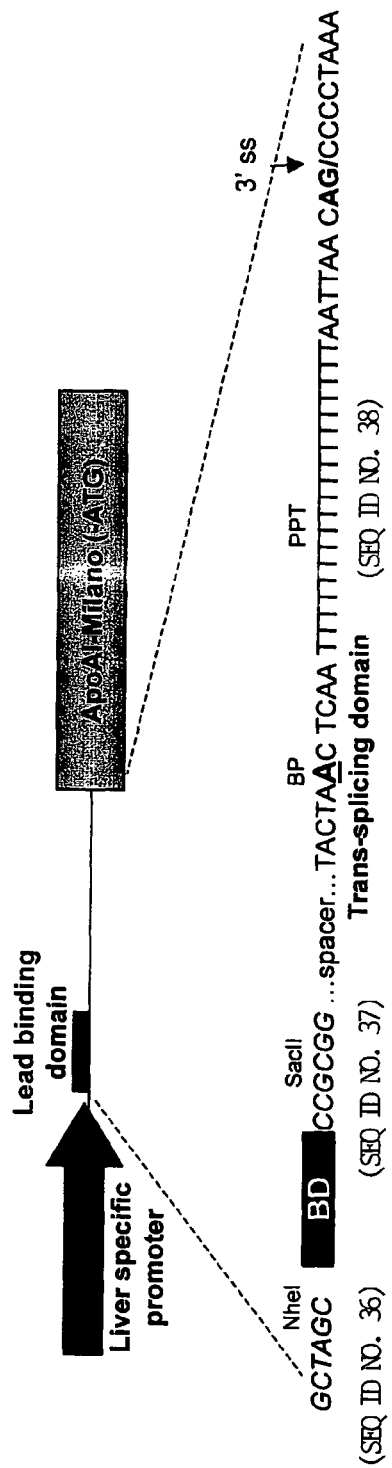
Figure 8

Human albumin Gene Structure

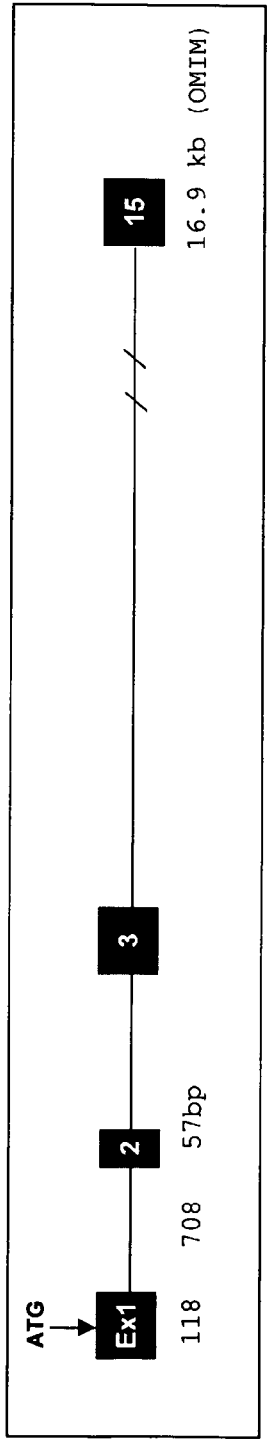

Gene: The human albumin gene is 16.96 kb long with 15 exons and 14 introns, located in chromosome 4 mRNA: 2.21 kb

Exon 1: 118 bp; codes for ~26 aa's of which the first 24 aa (-18 to -1 pre; -6 to -1 pro) codes for signal peptide

Protein: Soluble, monomeric protein which comprises about <u>one-half of the blood serum protein</u>. Normal range ~35 – 50 mg/ml.

Site of synthesis: Liver

Synthesized as <u>preproalbumin</u> which has an N-terminal signal peptide that is removed before the nascent protein is released from the rough endoplasmic reticulum. The product, proalbumin, is in turn cleaved in the golgi vesicles to produce the secreted albumin.

Figure 10

Human ApoAI

➤ Apolipoprotein A-I is the major apolipoprotein of HDL and is a relatively abundant plasma protein with a concentration of 1.0 - 1.5 mg/ml.

➤ Play an important role in promoting cholesterol efflux from cells and tissues.

➤ Gene: 1.87 kb, 4 exons
- Ex 1 non-coding; Ex2 & part of Ex3 codes for signal peptide, and Ex3 + Ex4 codes for the mature protein ➤ mRNA: 897 nt long including 5'UTR and 3'UTR sequences

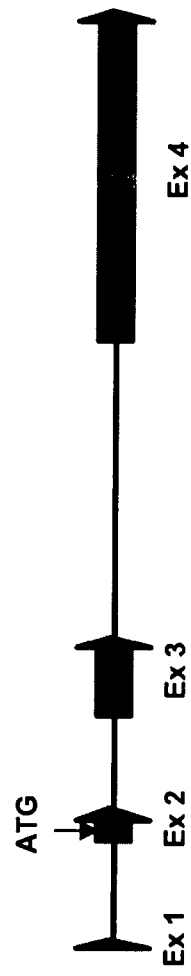

Figure 11

Human ApoAI gene & mRNA .... Details

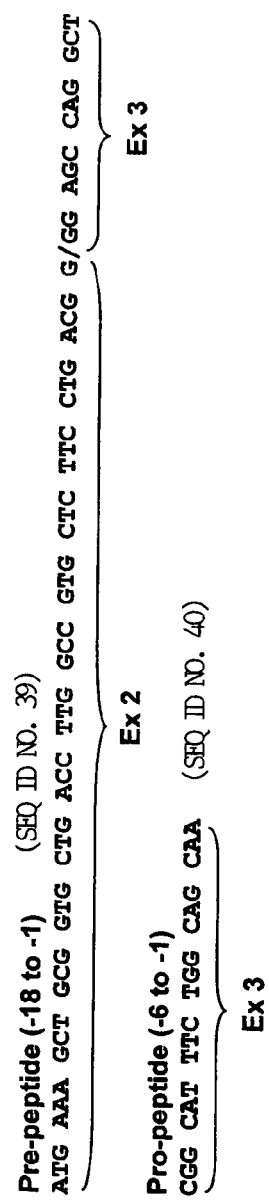

Ex 1: 18 bp, un-translated
Ex 2: 63 bp, codes for signal peptide
Ex 3: 152 bp, parts of Ex3 codes for pre & pro segment; remaining codes for mature AI protein
Ex4: 659 bp, codes for mature AI protein Pre-peptide (-18 to -1)   (SEQ ID NO. 39)
ATG AAA GCT GCG GTG CTG ACC CTC TTG GCC GTG CTC TTC CTG ACG G/GG AGC CAG GCT
                        Ex 2                                          Ex 3

Pro-peptide (-6 to -1)   (SEQ ID NO. 40)
CGG CAT TTC TGG CAG CAA
        Ex 3

Coding sequences for the mature protein (part of Ex 3 + Ex 4) :   (SEQ ID NO 41)

GAT GAA CCC CCC CAG AGC CCC TGG GAT CGA GTG AAG GAC CTG GCC ACT GTG TAC GTG GAT GTG CTC ...

ApoAI coding sequence to be included in the PTM (part of Ex 3 and entire Ex 4).

Figure 12

Figure. Schematic illustration of human and mouse albumin exon 1 – human ApoAI trans-spliced cDNAs.

Sequences of Human Albumin-hApoAI Trans-spliced cDNA

Human albumin-hApoAI trans-spliced cDNA:

Human albumin Signal peptide — Human ApoAI (Ex3-4) — stop — 3'UTR (SEQ ID NO. 43)

```
ATG AAG TGG GTA ACC TTT ATT TCC CTT CTT TTT CTC TTT AGC TCG GCT TAT TCC AGG GGT
GTG TTT CGT CGA GAT GCA C/CC AAA GAC AGC AGC AGA GAC TAT GTG TCC CAG TTT GAA GGC TCC ACT
GCC TTG GGA AAA CAG CTA AAC CAG CTC CTT GTG ACC TAT GAC AGC GTG AAG GAC TTT GAA GGC TCC ACC
TTC AGC AAG CTG CGC GAA CAG CTC GGC CCT GTG ACC CAG GAG TTC TGG GAT AAC CTG GAA
AAG GAG ACA GAG GGC CTG AGG CAG GAG ATG AGC AAG GAT CTG GAG GAG GTG AAG GCC AAG
GTG CAG CCC TAC CTG GAC GAC TTC CAG AAG AAG TGG CAG GAG GAG ATG GAG CTC TAC CGC
CAG AAG GTG GAG CCG CTG CGC GCA CTG GGC CTC CAA GAG GGC GCG CAG GCC GAG
CTG CAA GAG AAG CTG AGC CCA CTG GGC GAG GAG ATG CGC GAC CGC CTG CGC CAG CAT GTG
GAC GCG CTG CGC ACG CAT AAG GAG AAC GGC GAG ATG CGC GAC GAG CTG GCC CGC CTG CAA GAG CGG
CGC CTT GAG GCT CTC AAG GAG AAC GGC GGC GCC AGA CCC AAG GAG TAC CAC GCC AAG GCC
ACC GAG CAT CTG AGC ACG CTC AGC GAG AAG GCC AAG CCC GCG CTC GAG GAC CTC CGC CAA
GGC CTG CCC GTG CTG GAG TCG CTG AAG GTC AAG GCT CTG GCT CTC CGG TGC GAG TAC
ACT AAG AAG CTC AAC ACC CAG TGA GGC GCC CGC CGC CCC CCC CGG TGC TCA GAA
TAA ACG TTT CCA AAG TGG G
```

Figure. Nucleotide sequences of human albumin-human ApoAI (wild type) cDNA. Underlined sequence represents human albumin signal peptide; / indicate junction between albumin and ApoAI.

Figure 14

Western analysis of mouse and human Alb-hApoAI cDNA in 293 cells

Test for production & secretion

Details:
1. 293 cells transfected with 1 μg cDNA expression plasmids (3x10⁵ cells in 12 well plate)
2. 42 hr, supernatant collected & concentrated (8K/10 min)
3. Cell lysate was prepared (cells washed 1X w/ PBS, 300 ul lysis buffer, 10 min at RT, spin 8K/10 min)
4. Both cell lysate and supernatant was analyzed by western blot using wt apoAI monoclonal antibody that recognizes both wild type and milano variant.

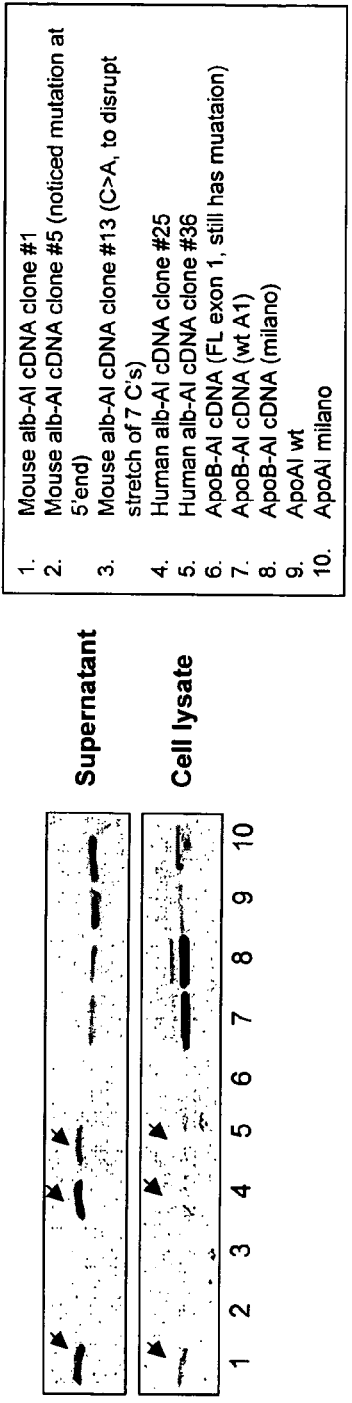

1. Mouse alb-AI cDNA clone #1
2. Mouse alb-AI cDNA clone #5 (noticed mutation at 5'end)
3. Mouse alb-AI cDNA clone #13 (C>A, to disrupt stretch of 7 C's)
4. Human alb-AI cDNA clone #25
5. Human alb-AI cDNA clone #36
6. ApoB-AI cDNA (FL exon 1, still has muataion)
7. ApoB-AI cDNA (wt AI)
8. ApoB-AI cDNA (milano)
9. ApoAI wt
10. ApoAI milano

Results:
1. Normal translation, processing and secretion observed from both mouse and human albumin-human ApoAI (wt) cDNA constructs. Very little protein observed in the lysate (compare lanes 1, 5 & 6 upper & lower panels).
2. On the other hand, majority of ApoB-hAI chimeric protein is in the cell lysate (lanes 7 & 8, lower & upper panels) which confirmed previous results.

Figure 15

Western analysis of mouse and human Alb-hApoAI cDNAs - Test for production & secretion in 293 & HepG2 cells

Details:
1. 293 and HepG2 cells transfected with 1 μg cDNA expression plasmids (3x10⁵ cells in 12 well plate)
2. 48 hr, supernatant collected and analyzed by Western blot using wt apoAI monoclonal antibody.

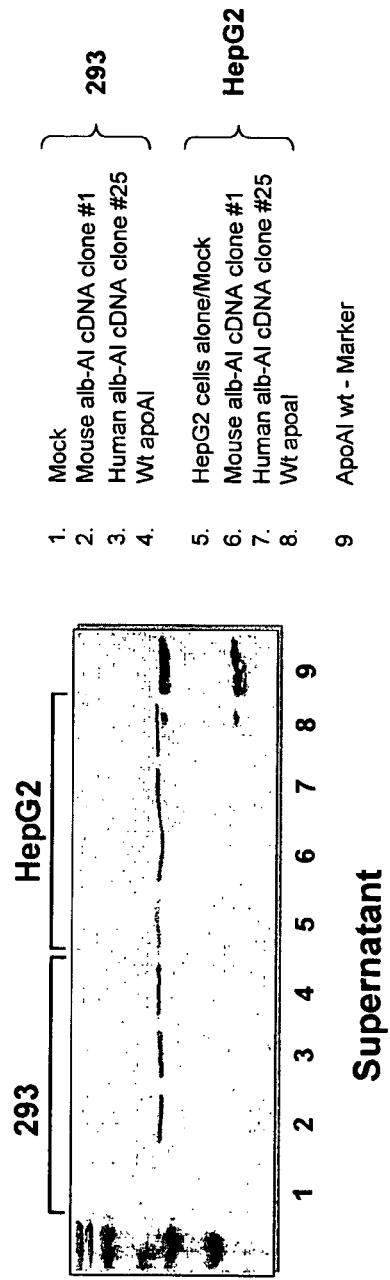

293
1. Mock
2. Mouse alb-AI cDNA clone #1
3. Human alb-AI cDNA clone #25
4. Wt apoAI HepG2
5. HepG2 cells alone/Mock
6. Mouse alb-AI cDNA clone #1
7. Human alb-AI cDNA clone #25
8. Wt apoaI 9. ApoAI wt - Marker

Conclusion:
1. In both 293 and HepG2 cells, normal translation, processing and secretion was observed with mouse as well as human albumin-human apoAI cDNAs.

Figure 16

Target Construct for Binding Domain Screen

5'GFP-AlbIn1Ex2 Target:

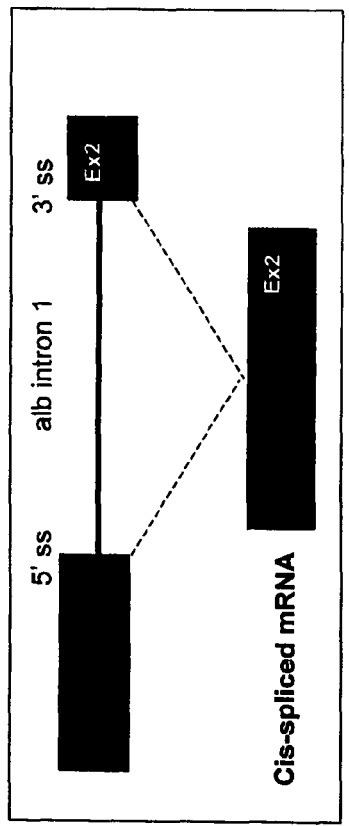

Partial sequence of cis-spliced product:  (SEQ ID NO. 44)

....GGA AAC AG /A CAA GAG TGA GGT TGC TCA TCG GTT TAA AGA TTT GGG AGA AGA AAA TTT CAA AGC CTT

Figure. Schematic structure of 5'GFP-AlbIn1Ex2 target gene for *in vitro* studies. Target pre-mRNA construct contains partial coding sequence for GFP fluorescent protein folloed by 5' splice albumin intron, 3' acceptor site and albumin exon 2.

Figure 17

5'GFP-AlbIn1Ex2 Pre-mRNA Target Sequence

*ATGGCTCAGTCAAAGCACCGGTCTAACAAAAGAAATGACAAATGAAATACCGTATGGAAGGGTGCGTCGATG*
*GACATAAATTTGTGATCACGGGAGAGGCATTGGATATCCGTTCAAAGGGAAACAGGCTATTAATCTGTG*
*TGTGGTCGAAGGTGGACCATTGCCATTGCCGAAGACATATTGTCAGCTGCCTTTATGTACGGAAACAG/* (SEQ ID NO. 45)

5' splice junction

GTAAGAAATCCATTTTCTATTGTTCAACTTTTATTCTATTTCCCAGTAAAATAAAGTTTTAGTAAACT
CTGCATCTTTAAAGAATTATTTTGGCATTTATTTCTAAAATGGCATAGTATTTTGTATTTGTGAAGTCTT
ACAAGGTTATCTTATTAATAAAATTCAAACATCCTAGGTAAAAAAAAAAGGTCAGAATTGTTTAGTG (SEQ ID NO. 46)
ACTGTAATTTTCTTTTGCGCACTAAGGAAAGTGCAAAGTAACTTAGAGTGACTGAAACTTCACAGAATAG
GGTTGAAGATTGAATTCATAACTATCCCAAAGACCTATCCATTGCACTATGCTTTATTTAAAAACCACAA
AACCTGTCGCTGTTGATCTCATAAATAGAACTTGTATTTATATTTATTTCATTTTAGTCTGTCTTCTTGG
TTGCTGTTGATAGACACTAAAGAGTATTAGATATTATCTAAGTTTGAATATAAGGCTATAAATATTTAA
TAATTTTAAAATAGTATTCTTGGTAATTGAATTATTCTTCTGTTTAAAGGCAGAAGAAATAATTGAACA
TCATCCTGAGTTTTCTGTAGGAATCAGAGCCCAATATTTGAAACAAATGCATAATCTAAGTCAAATGG
AAAGAAATATAAAAAGTAACATTATTACTTCTTCTGTTTTCTTCAGTATTTAACAATCCTTTTTTCTTCC

3' splice junction

CTTGCCCAG/<u>ACAAGAGTGAGGTTGCTCATCGGTTCATCGGTTAAAGATTTGGGAGAAGAAAATTTCAAAGCCTT</u> (SEQ ID NO. 47)

Figure. Nucleotide sequence of 5'GFP-AlbIn1Ex2 target gene for *in vitro* studies. Sequences shown in italics indicate first half of the coding sequence for GFP fluorescent protein followed by human albumin intron 1 and exon 2 sequences (underlined). "/" indicate 5' and 3' splice junctions.

Figure 18

Binding Domain Screening Strategy

A: High Capacity Screen:

BD library: PCR amplify albumin intron 1 and exon 2, ligate to concatamerize, sonicate, end fill, gel purify 50-250 bp sized fragments and construct BD library with pc3.1B-GR1 vector (modified vector backbone).

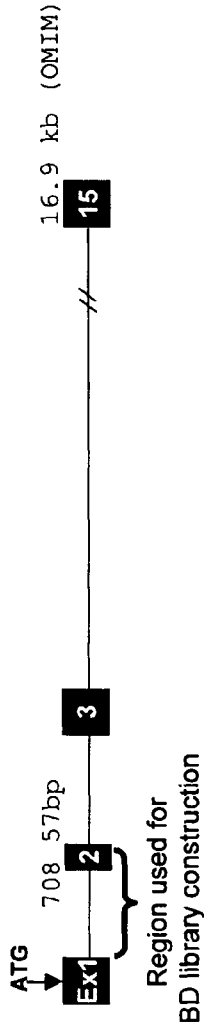

Region used for BD library construction

B: Rational design:

BDs: Design 7-10 BDs (~100 nt in size) spanning across intron 1 and exon 2; screen for cryptic donor sites based on strength (nt match to authentic donor site), clone BDs and test using 5'GFP-mAlbIn1Ex2 target.

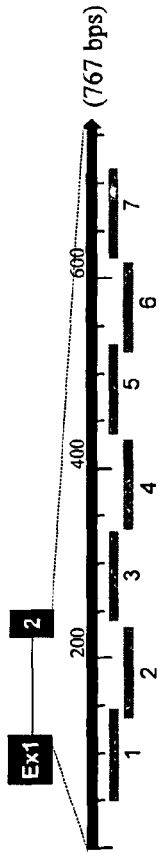

Figure 20

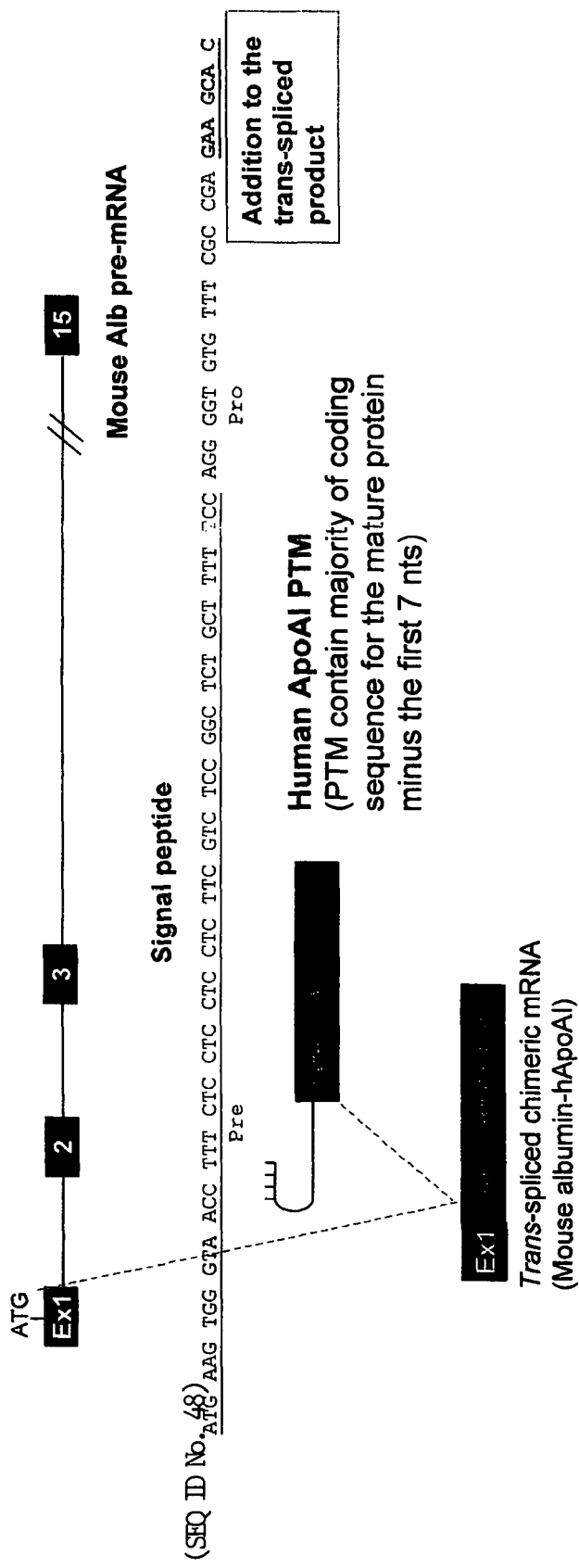
Fig. 21. SMaRT™ concept showing *trans*-splicing mediated human ApoAI expression.

Figure 23:
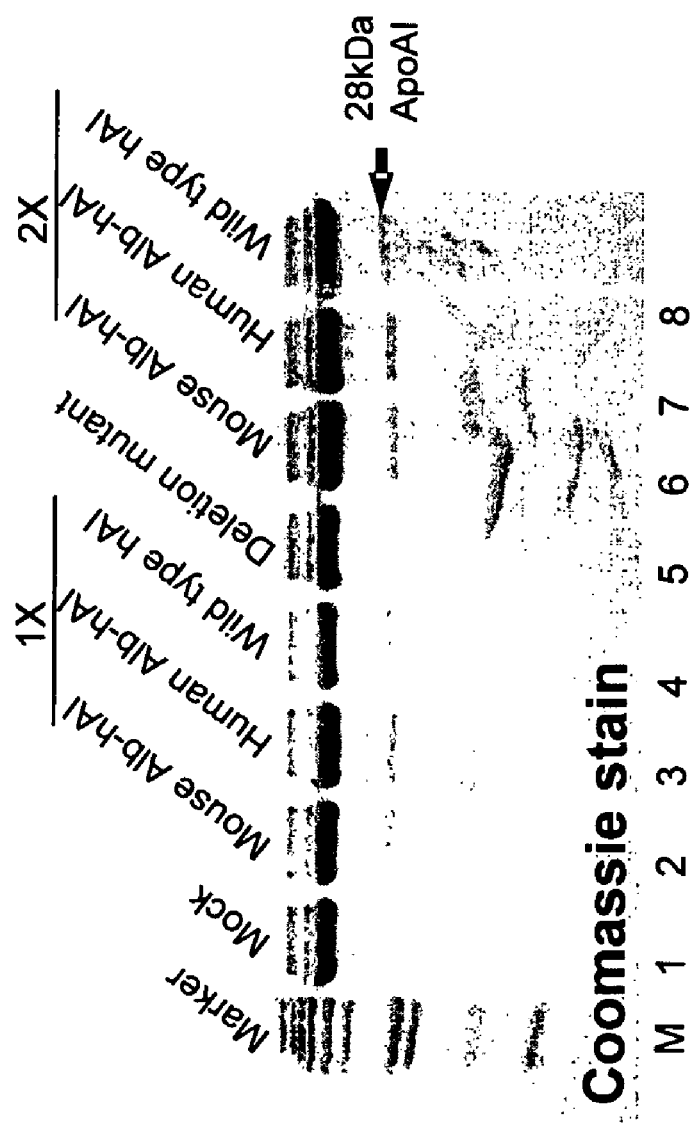

Fig. 23. SDS gel showing the production of human Apo A-I protein in 293 cells.

Figure 25:
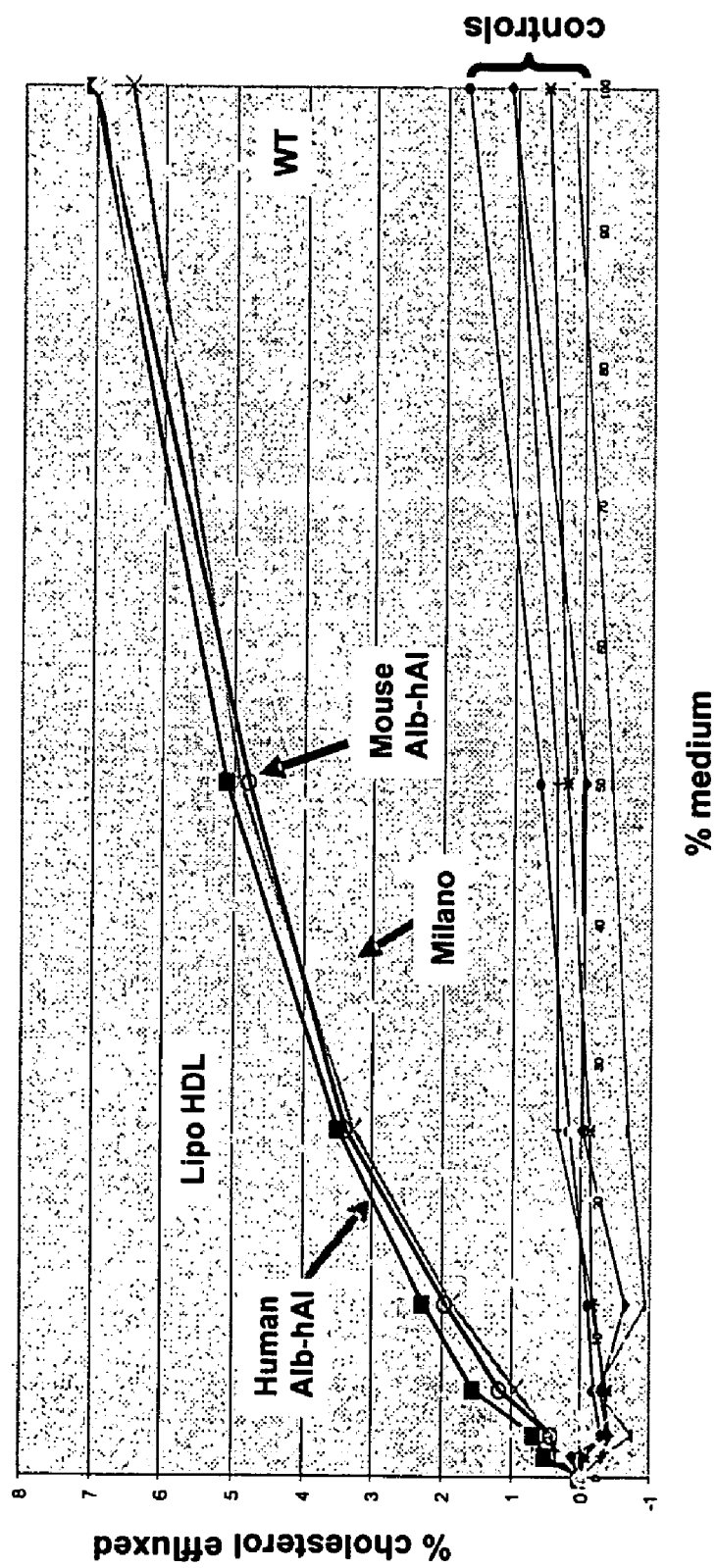

Fig. 25. Cholesterol efflux from HeLa control and ABC1 cells with conditioned media from albumin-hApoAI expressing 293 cells.

Figure 26:
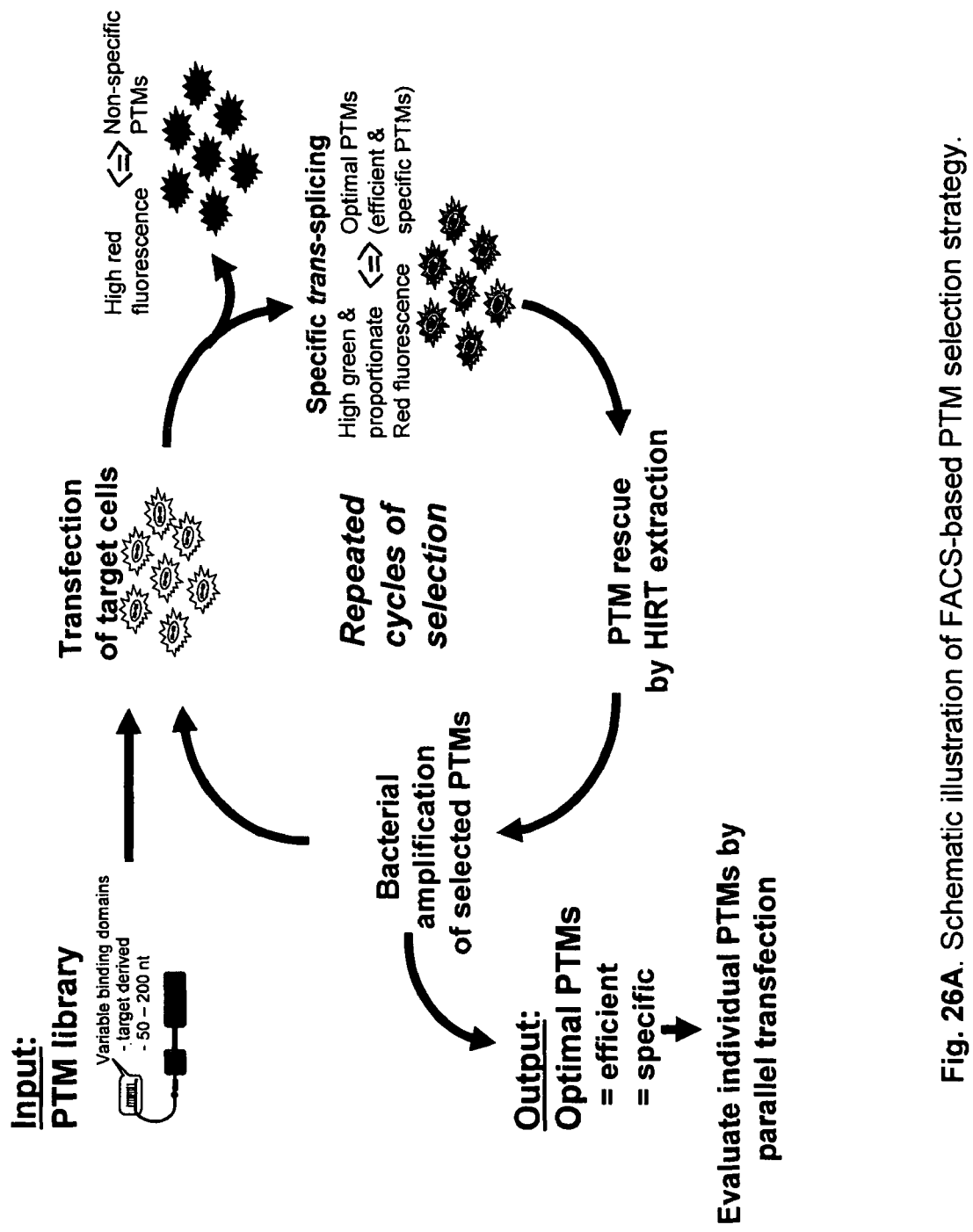

Fig. 26A. Schematic illustration of FACS-based PTM selection strategy.

Previous Protocol:

1. Library in pQC vector backbone (w/ Maz)

2. Cells collected as single fraction (mean $10^1$-$10^4$)

3. After first round, routinely tested 20-40 clones by parallel transfection 4. Selected the winner from these clones

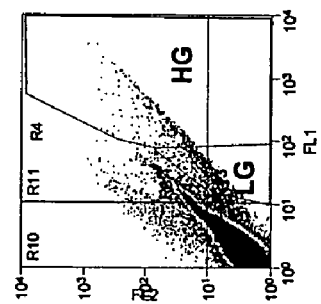

Current (modified) Protocol:

1. Library in pc3.1B vector backbone (pc3.1 with Maz to reduce cryptic *cis*-splicing to amp gene, and, is a high copy number plasmid).

2. Cells collected as two fractions, LG (mean $10^1$-$10^2$) and HG (mean $10^2$-$10^4$)

3. After first round, pre-tested 40 clones from each fraction and found that the HG fraction had higher (& brighter) GFP positive cells than LG fraction (2:1)

4. Tested ~100 PTMs from HG fraction by parallel transfection

5. Selected 20 PTMs for further analysis.

6. Also, tested the effect of target conc. to "better" discriminate the winner from the pool. Based on the results, reducing the target conc. that is comparable to stables produced better results.

7. The lead candidate BDs were selected from 140 clones.

Fig. 26B. Comparison between previously described HCS vs. the current HCS steps.

Figure 27:
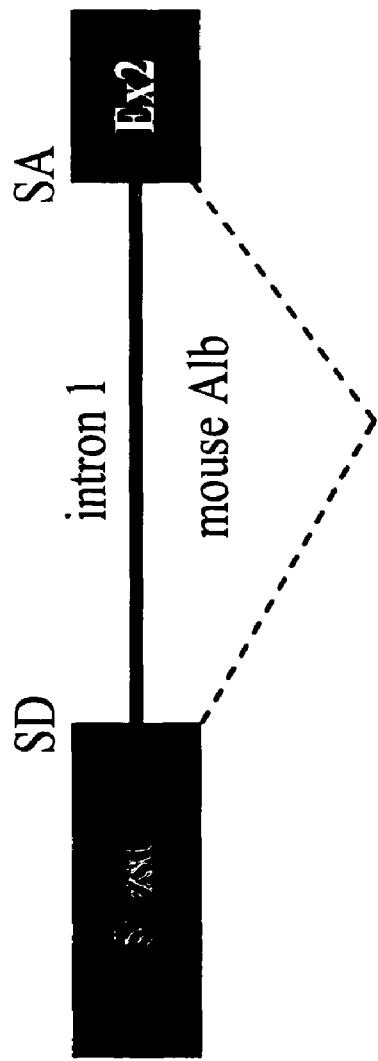

Fig. 27. Schematic diagram of the pre-mRNA target used in the HCS. Abbreviations: SD, splice donor site; SA, splice acceptor site. Dotted lines indicate target cis-splicing.

Figure 29:
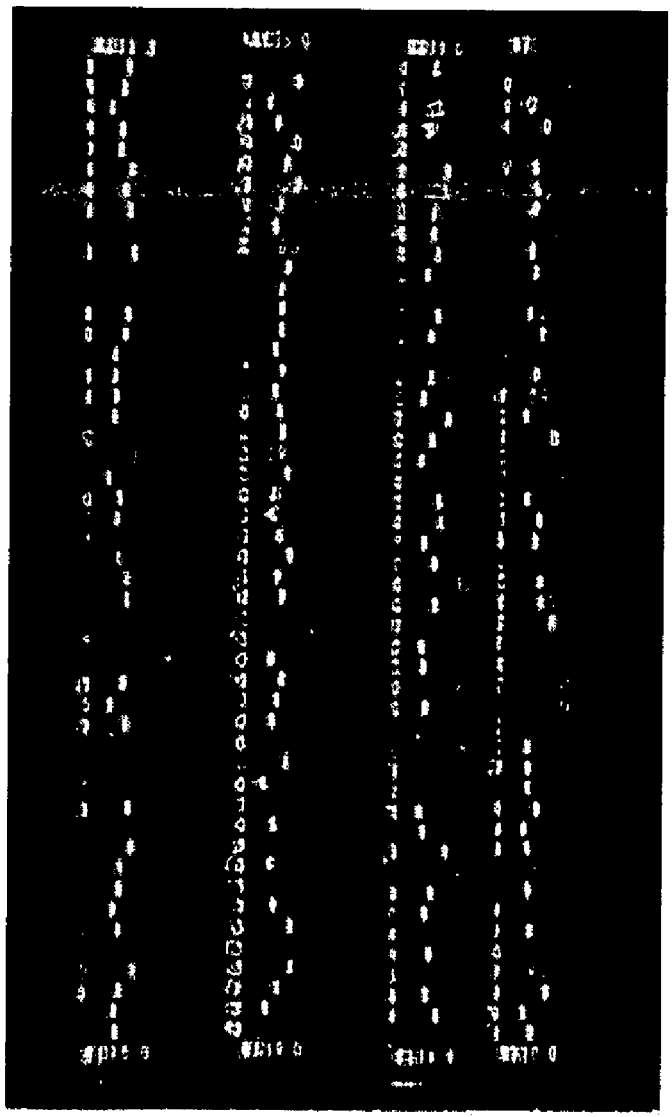

Fig. 29. PCR screen showing the cloning efficiency and diversity of the mouse albumin BD library.

Figure 30:
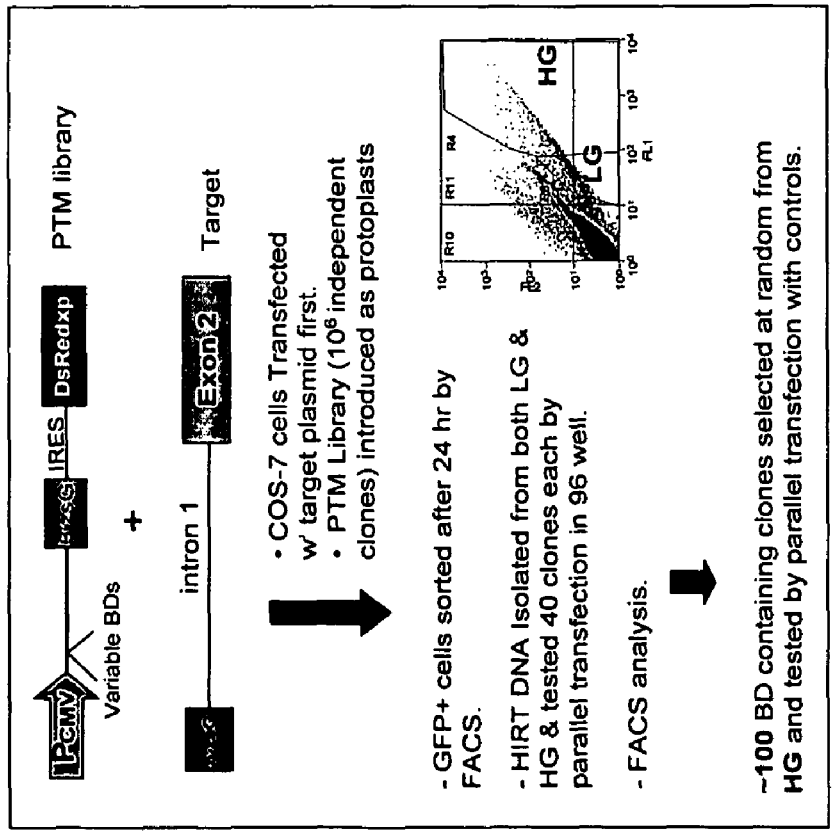

Fig. 30. Schematic illustration of HCS steps.

Figure 31:
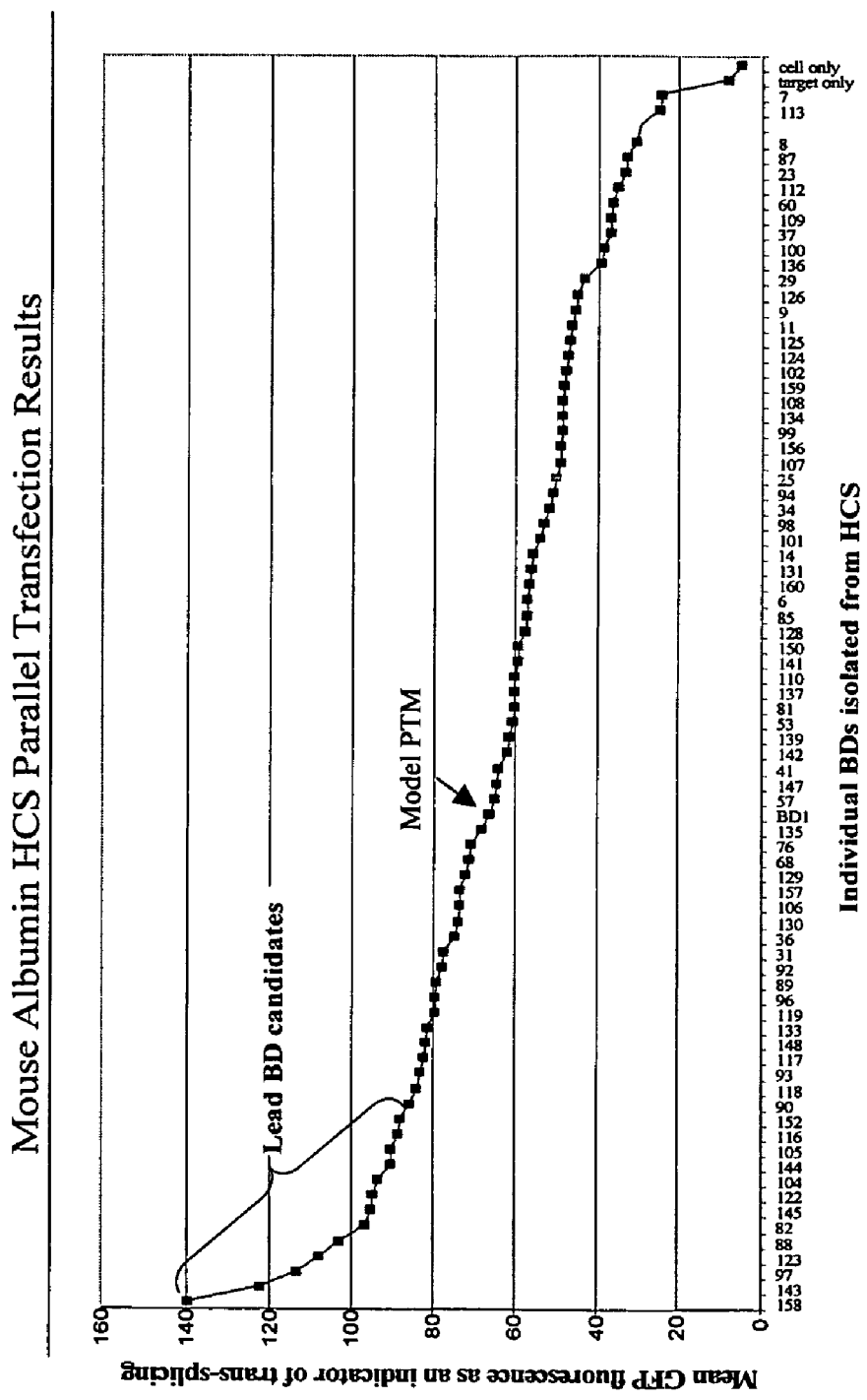

Fig. 31. *Trans*-splicing efficiency of PTMs selected from HCS for mouse albumin target.

Figure 32:
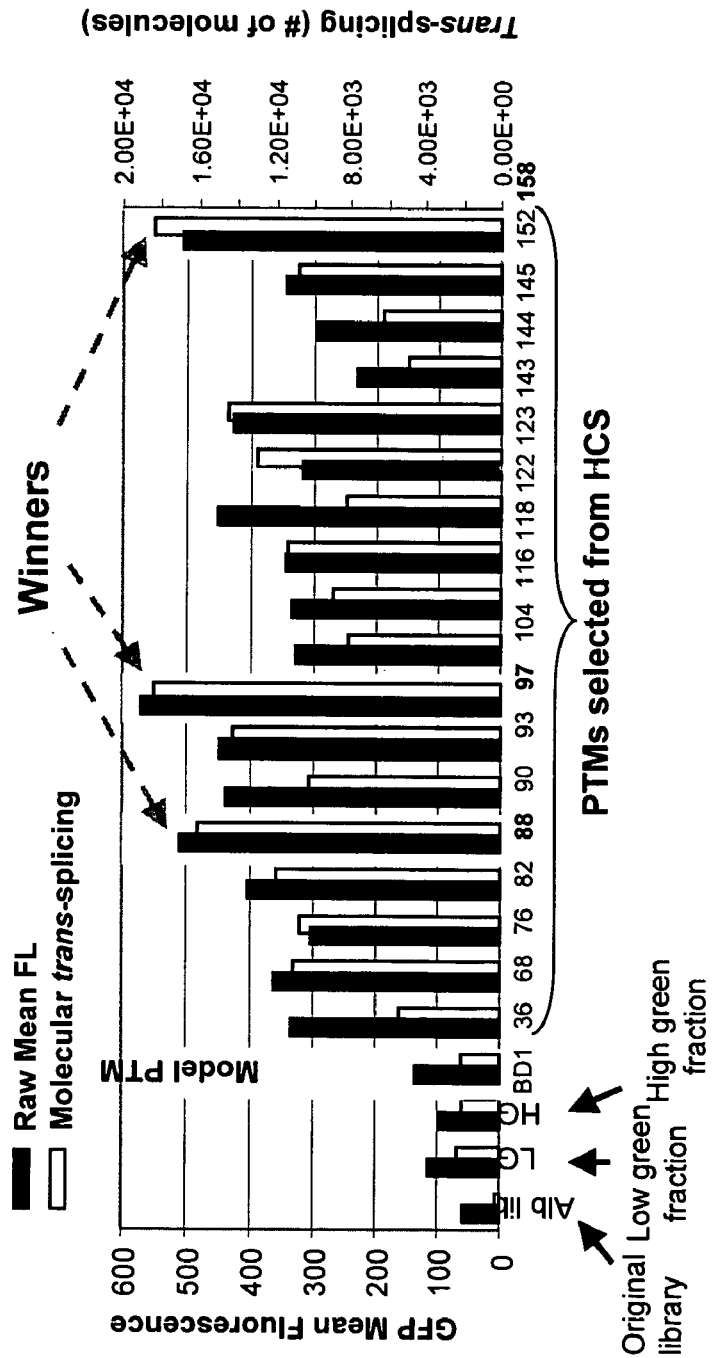

Fig. 32. *Trans*-splicing efficiency of top 20 PTMs selected from the HCS assessed by FACS and qRT-PCR.

Figure 33:
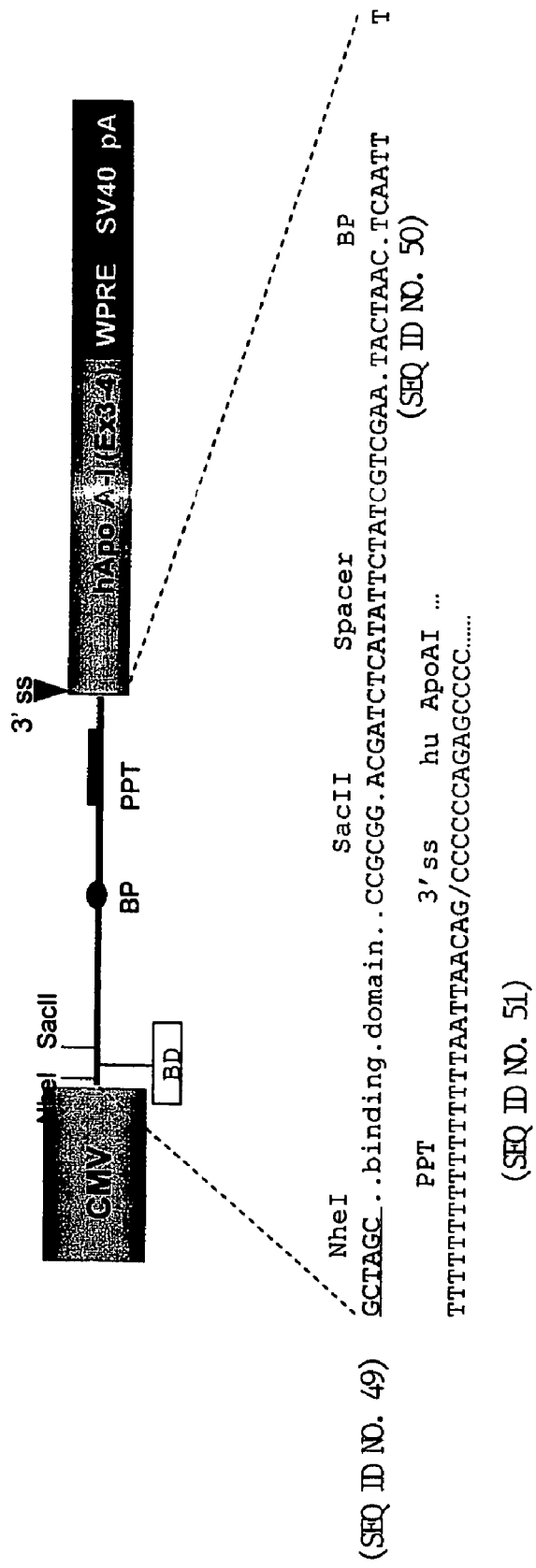

Fig. 33. Schematic illustration of human Apo A-I PTM expression cassette used for *in vitro* POP studies.

Figure 34:
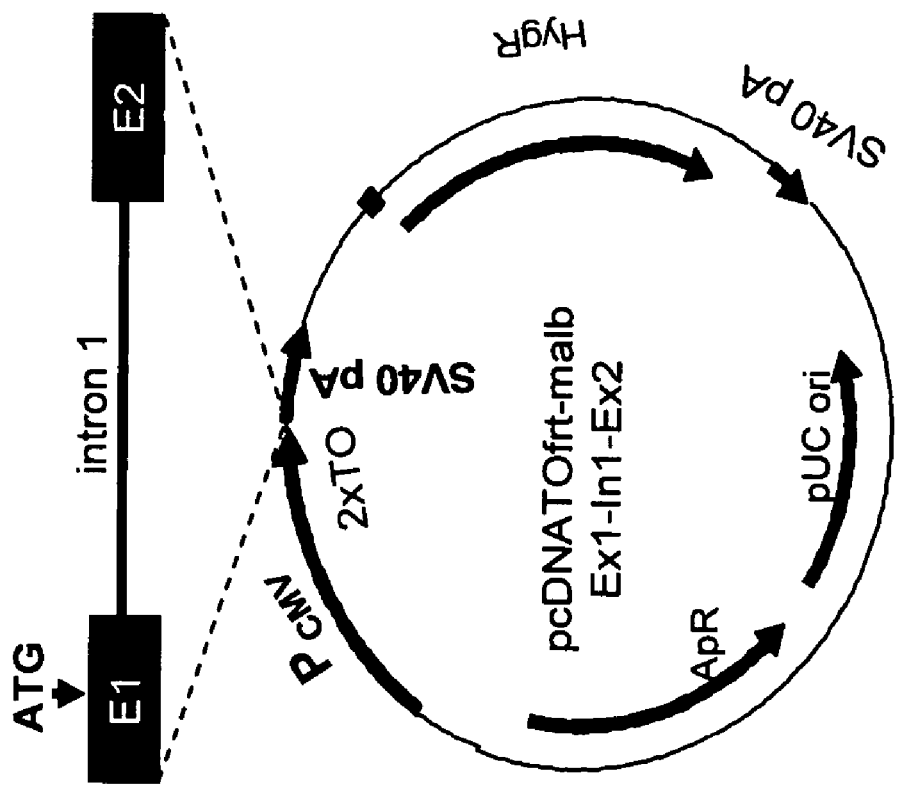

Fig. 34. Schematic diagram of the mouse albumin mini-gene pre-mRNA target.

Figure 35:
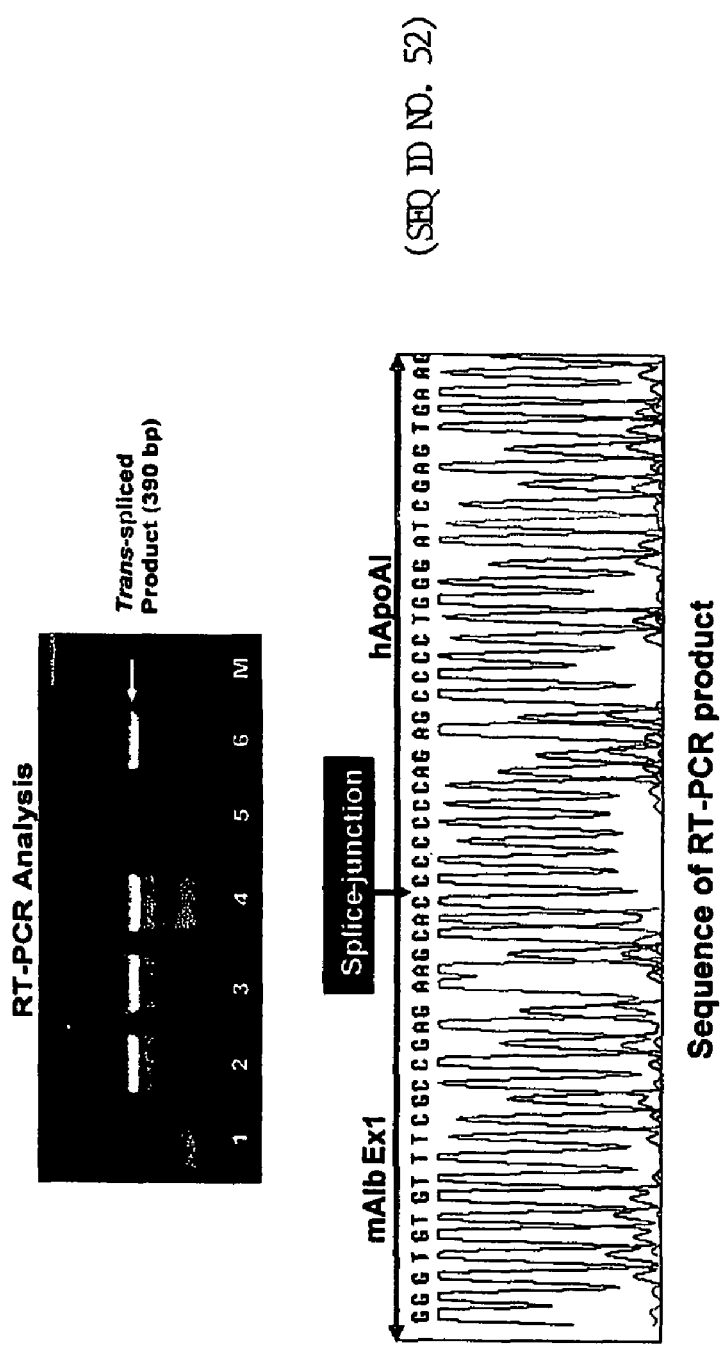

Fig. 35. Evidence of precise trans-splicing of mAlbPTMs into albumin exon 1 in stable cells.

Figure 36:
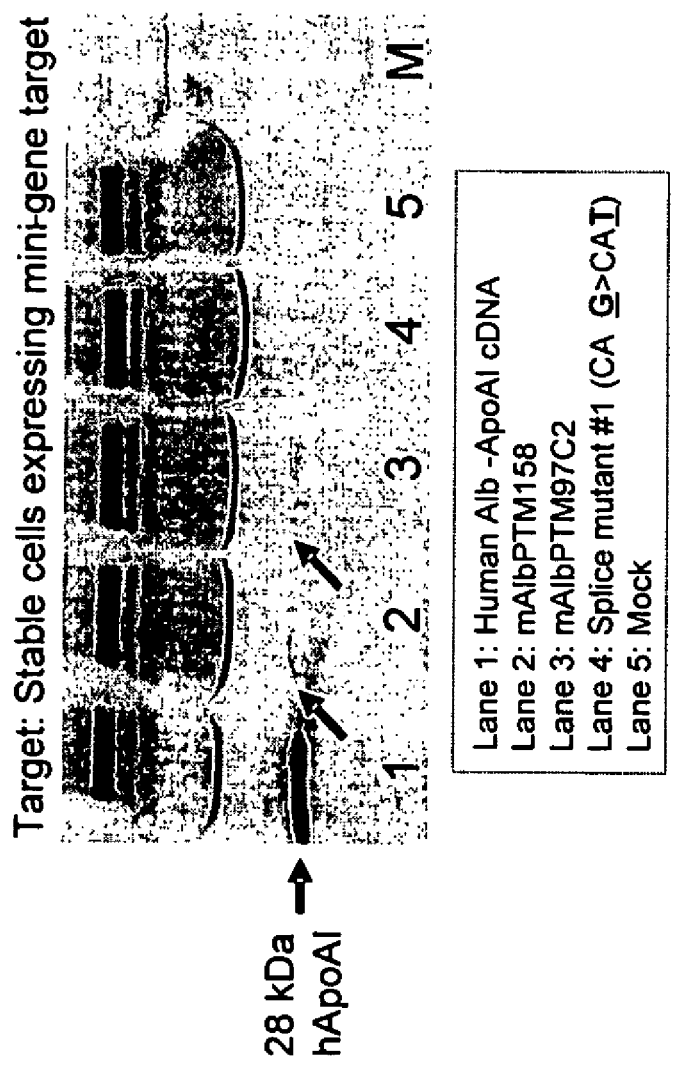

Fig. 36. Detection of *trans*-spliced human Apo A-I protein by Western blot.

Figure 37:
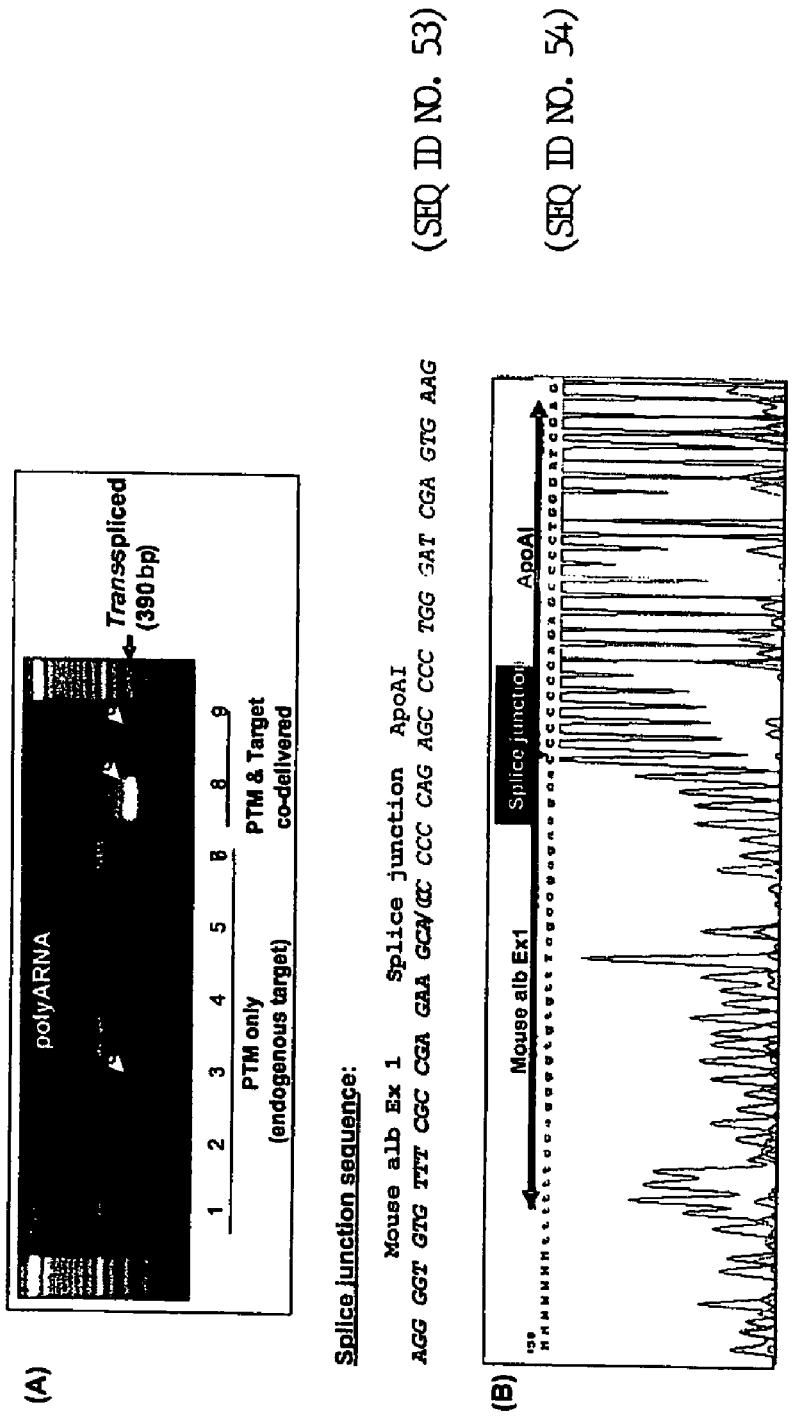

Fig. 37. PTM mediated *trans*-splicing into endogenous albumin exon 1 in mice.

Strategies to eliminate albumin sequence in the final *trans*-spliced product.

PTM ApoAI sequences (human NP_000030. apolipoprotein A-I...[gi:4557321])
» SIGNAL PEPTIDE CLEAVAGE AT RER
« PRO PEPTIDE CLEAVAGE AT GOLGI Pre          Pro        Pro     hApoAI 1. MKWVTFISLLFLFSSAYS»RGVFRR«DAPRGVFRR«*DEPP*.....ApoAI sequence
cDNA construct designed to include additional albumin propeptide (underlined) followed by the entire mature coding sequence for ApoAI. Proline (in bold) was used as a junction amino acid.

2. MKWVTFISLLFLFSSAYS»RGVFRR«DAPRHFWQQ«*DEPP*....ApoAI sequence
cDNA construct designed to include human ApoAI pro-peptide (underlined) in addition to albumin pro-peptide followed by the entire mature coding sequence for ApoAI. Proline (in bold) was used as a junction amino acid.

3. MKWVTFISLLFLFSSAYS»RGVFRR«DARHFWQQ«*DEPP*....ApoAI sequence
cDNA construct designed to include human ApoAI pro-peptide (underlined) in addition to albumin pro-peptide followed by the entire mature coding sequence for ApoAI. The additional ApoAI pro-peptide was linked directly into albumin sequence without Proline.

With the presence of a second pro-peptide (albumin or ApoAI), these chimeric proteins will now undergo a second cleavage resulting in the final trans-spliced product that is identical to the wild type ApoAI sequence i.e., without any albumin sequence.

Similarly, PTMs can also be engineer to include peptidase cleavage site(s) or signal peptides which after trans-splicing would be recognized and cleaved to release the final product that is identical to ApoAI sequence i.e., without any albumin sequence.

Fig. 39. Schematic showing the strategies to eliminate albumin sequence in the final *trans*-spliced product.

*In Vivo* POP Studies in Normal Mice - PCR Results

Experimental Details:

➤ Total RNA from liver tissue isolated and analyzed by end-point PCR using mouse albumin exon 1 and human ApoAI specific primers.
  ➤ RNA per reaction = 1 µg
  ➤ PCR cycles = 25

Results:

mAlb-hAI cDNA:
➤ 11 out of 14 positives
  ➤ 3 that were negative (#23, 42 & 45): questionable injections.

Co-delivered samples:
➤ 100% positive for *trans*-splicing.

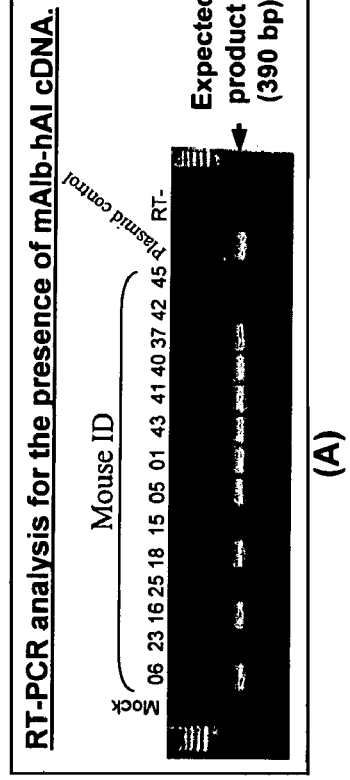

(A)

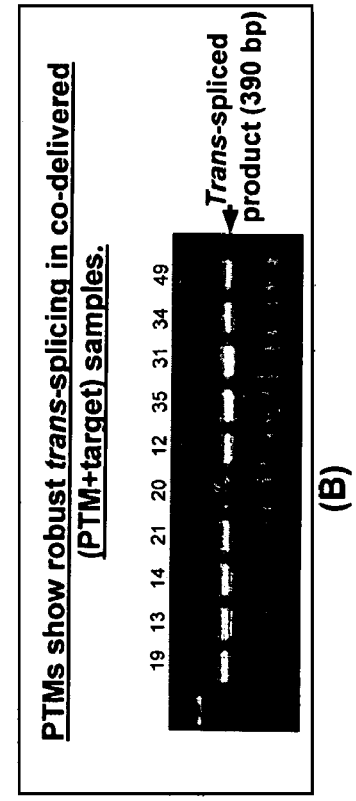

(B)

Fig. 43. RT-PCR results showing the presence of (A) mouse albumin-human Apo A-I mRNA and (B) *trans*-spliced mRNA in mice.

*In Vivo* POP Studies in Normal Mice - PCR Results
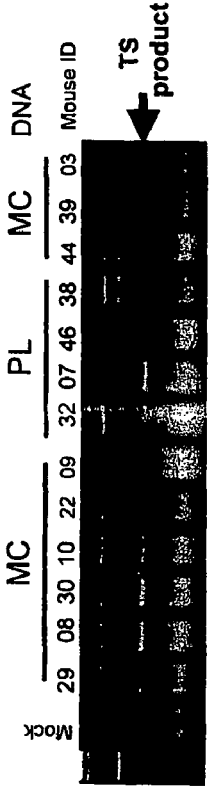
➢ PTM only samples analyzed for trans-splicing into endogenous albumin target pre-mRNA
➢ 10/13 mice were positive for trans-splicing.
• 03, 09, 22; questionable injection
Re-analysis of positive samples along with RT(-) controls
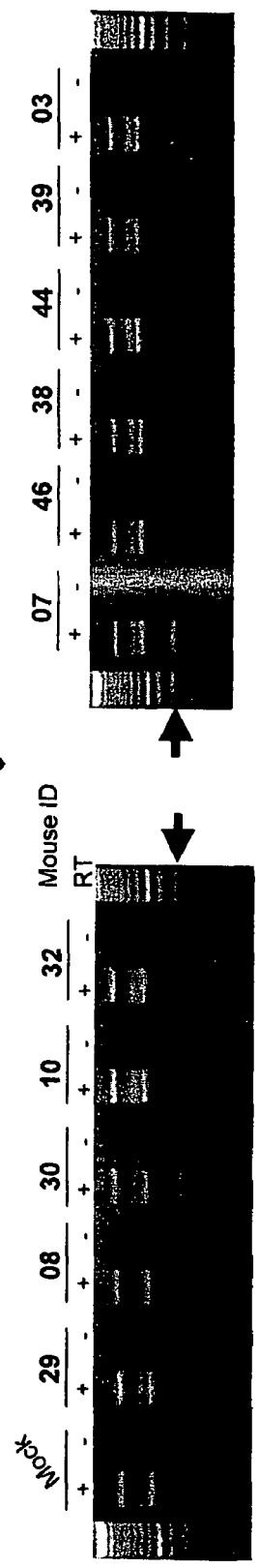
Fig. 43C.

hApoAI protein produced through *trans*-splicing in mice
Study #6
- Minicircle-PTM (75 μg/mouse)
- Time point: 48-2 wks
- Mice: C57BL/6 males
- 50 μl serum immuno-precipitated using monoclonal antibody to human ApoAI followed by Western w/ the same antibody.
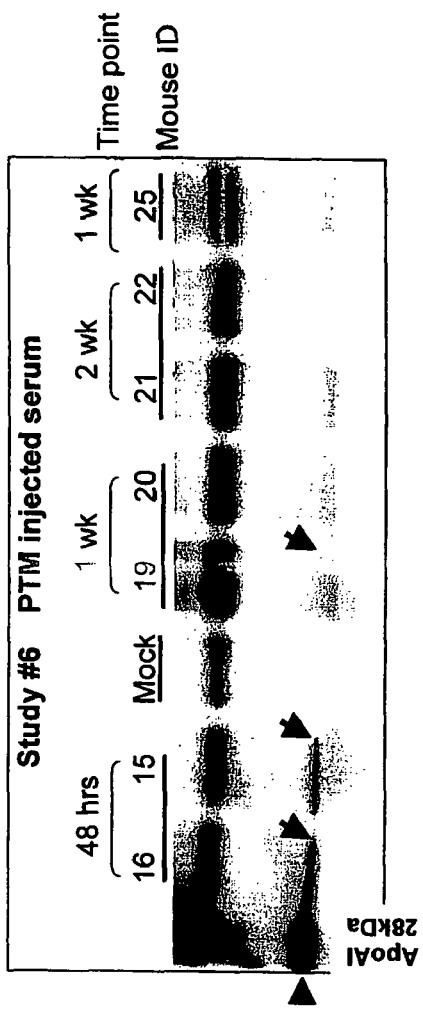
Study #7
- Minicircle-PTM (75 μg/mouse)
- Time point: 48 hrs
- Mice: C57BL/6 females
- IP and Western conditions same as above.
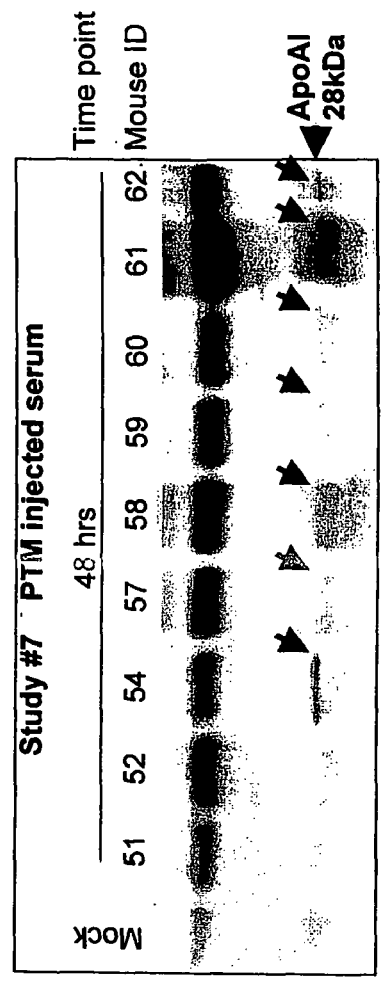
Fig. 45A.

Production of hApoA-I protein in mice: cDNA samples
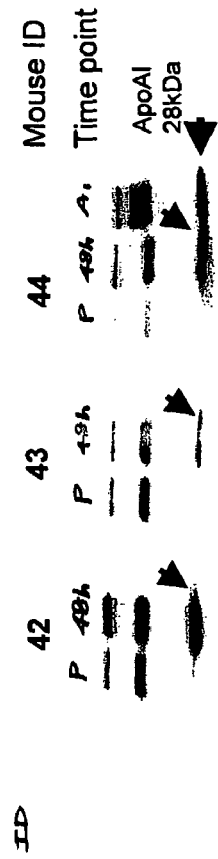
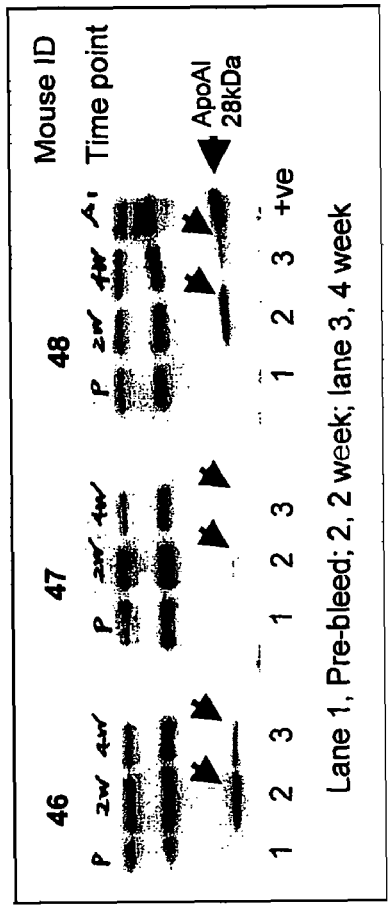
Study #6
- Minicircle-cDNA (75 µg/mouse)
- Time point: 48 hrs - 4 wks
- Mice: C57BL/6 males
- 10 µl serum used for IP. IP and Western conditions same as previously described.
Fig. 45B.

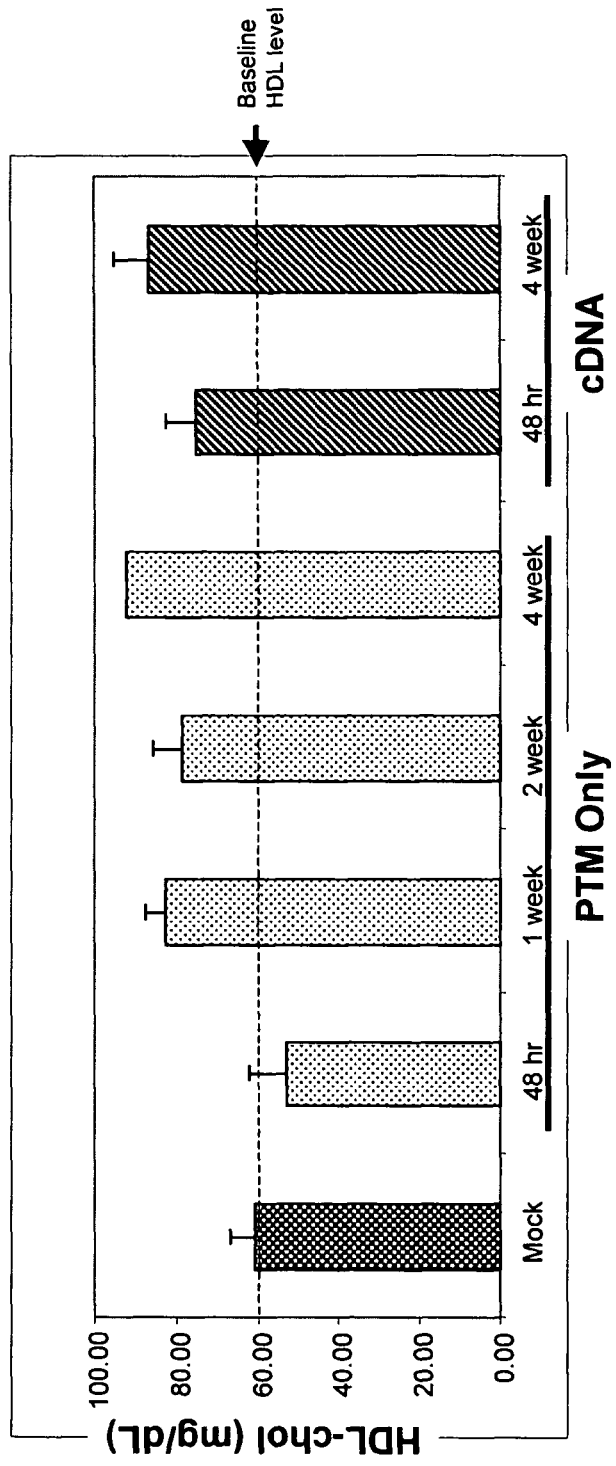
Fig. 46. HDL analysis of serum samples from mice injected with PTM and cDNA plasmids.

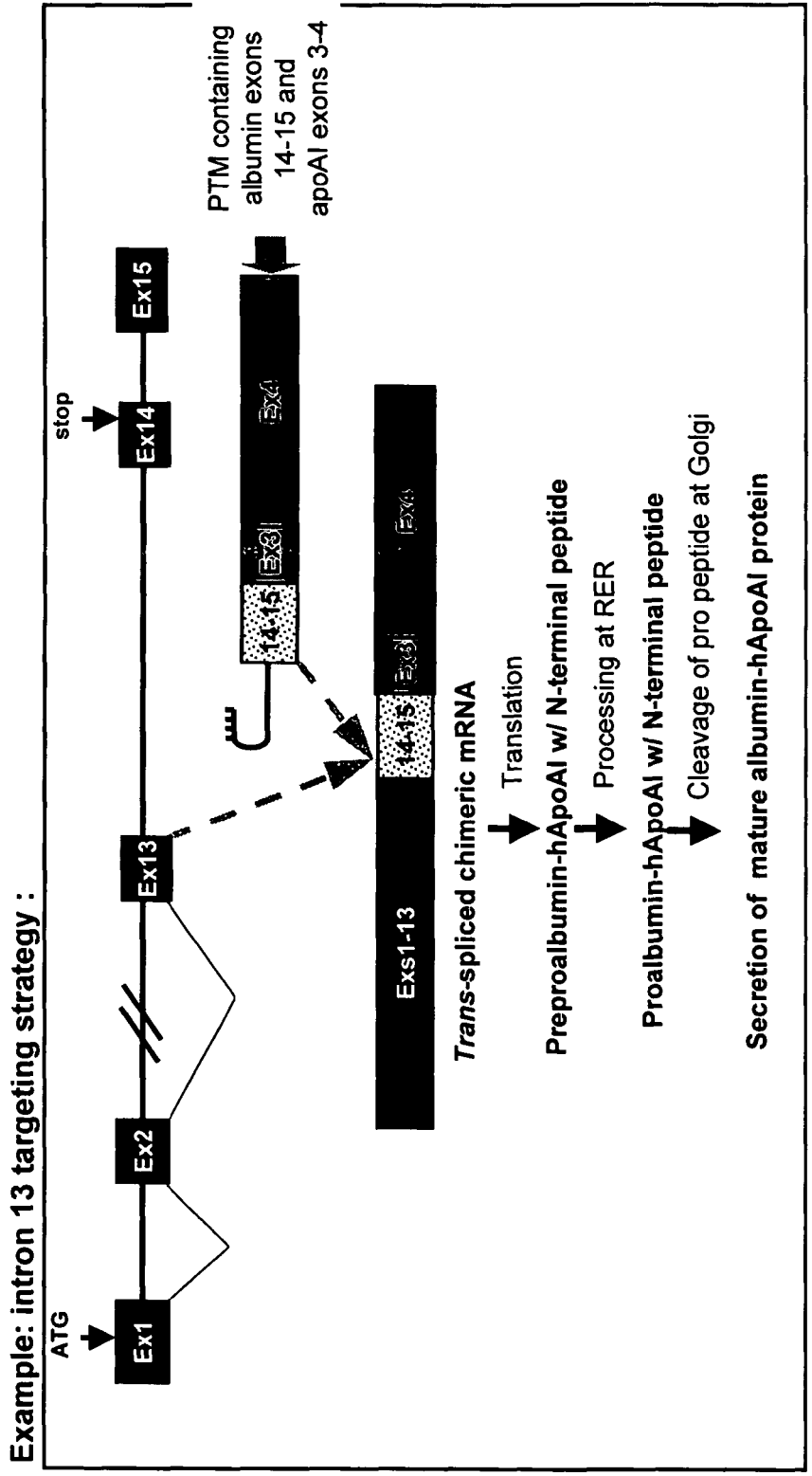
Fig. 47. Schematic illustration of trans-splicing strategy to increase biological half-life of human Apo A-I protein. Ex, exon.

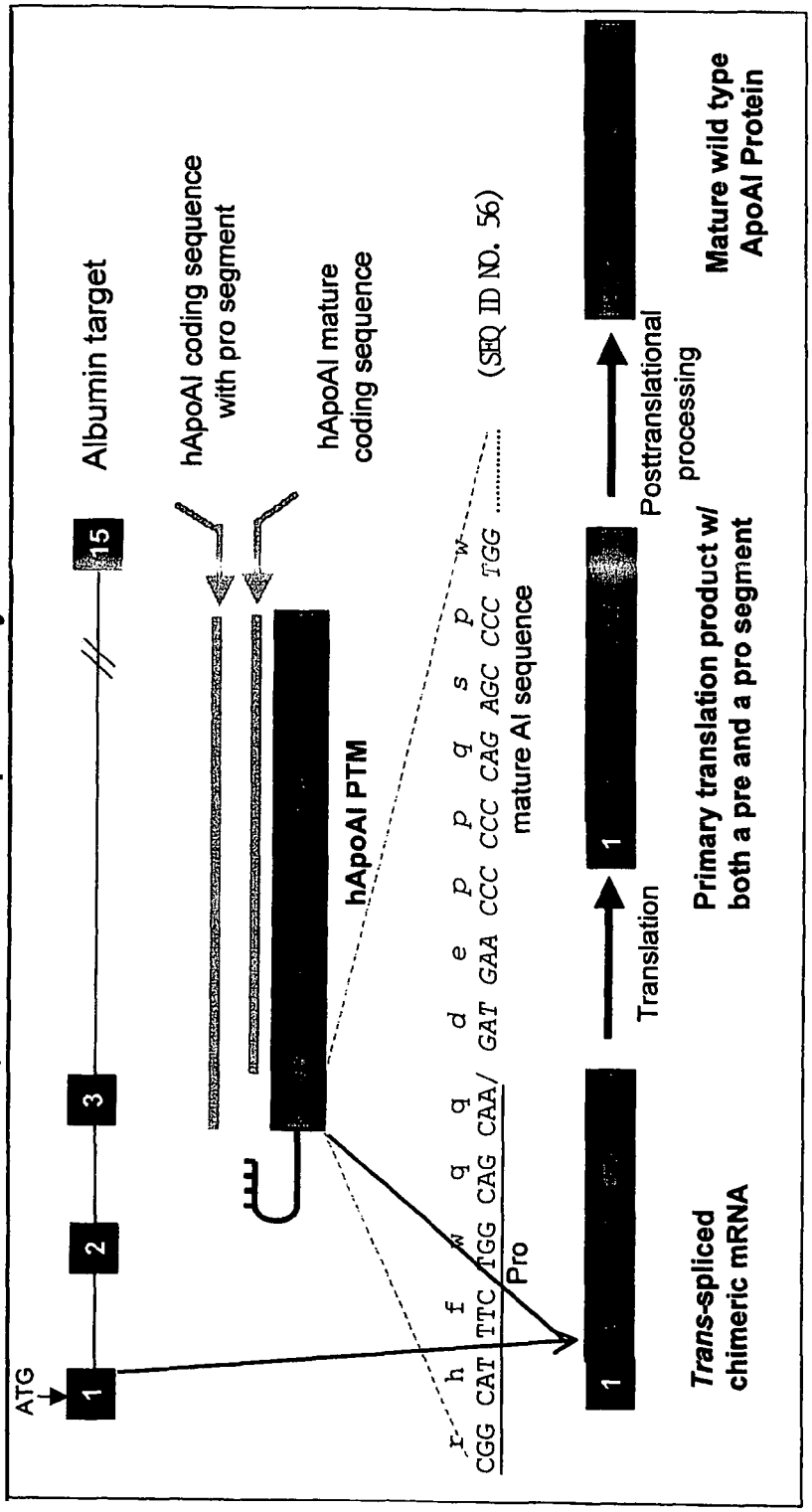
Fig. 48. Schematic illustration of *trans*-splicing (pro) strategy to improve function. Pro, sequence encoding for hApoAI pro peptide.

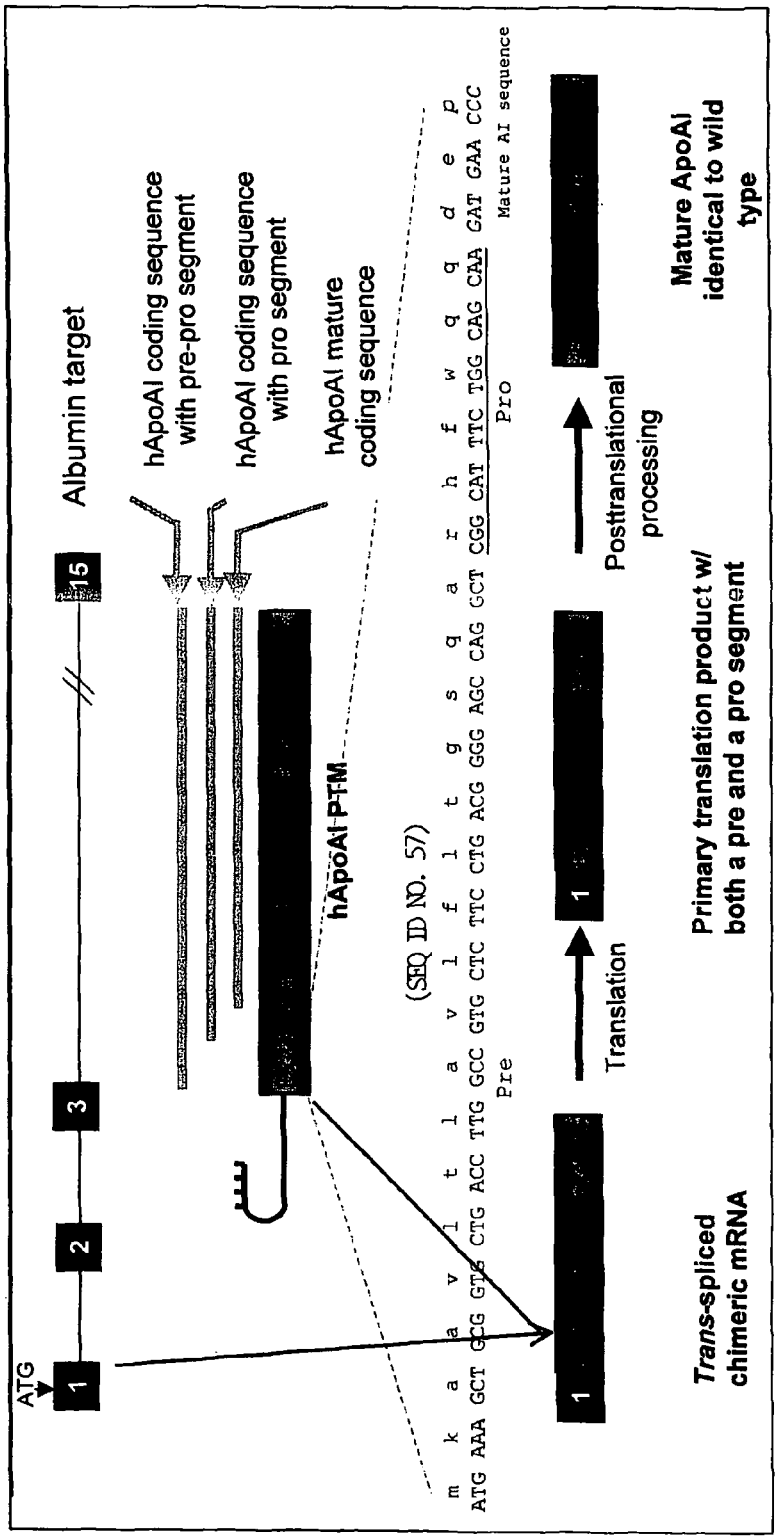
Fig. 49. Schematic illustration of *trans*-splicing (pre-pro) strategy to improve function. Pre, sequence codes for hAI pre signal peptide; Pro, sequence encoding for hAI pro signal peptide.

SEQUENCE LISTING

<160> NUMBER OF SEQ ID NOS: 57

<210> SEQ ID NO 1
<211> LENGTH: 8
<212> TYPE: RNA
<213> ORGANISM: Artificial
<220> FEATURE:
<223> OTHER INFORMATION: Chemically Synthesized

<400> SEQUENCE: 1 agguragu                                                                    8

<210> SEQ ID NO 2
<211> LENGTH: 7
<212> TYPE: RNA
<213> ORGANISM: Artificial
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: n is a, c, g, or u

<400> SEQUENCE: 2 ynyurac                                                                     7

<210> SEQ ID NO 3
<211> LENGTH: 258
<212> TYPE: DNA
<213> ORGANISM: Artificial
<220> FEATURE:
<223> OTHER INFORMATION: Chemically Synthesized

<400> SEQUENCE: 3 gtagttctttt tgttcttcac tattaagaac ttaatttggt gtccatgtct ctttttttt      60 ctagtttgta gtgctggaag gtattttgg agaaattctt acatgagcat taggagaatg      120
tatgggtgta gtgtcttgta taatagaaat tgttccactg ataatttact ctagttttt      180 atttcctcat attattttca gtggcttttt cttccacatc tttatatttt gcaccacatt      240
caacactgta gcggccgc                                                     258

<210> SEQ ID NO 4
<211> LENGTH: 270
<212> TYPE: DNA
<213> ORGANISM: Artificial
<220> FEATURE:
<223> OTHER INFORMATION: Chemically Synthesized

<400> SEQUENCE: 4
ccaactatct gaatcatgtg ccccttctct gtgaacctct atcataatac ttgtcacact      60
gtattgtaat tgtctctttt actttcccctt gtatcttttg tgcatagcag agtacctgaa    120
acaggaagta ttttaaatat tttgaatcaa atgagttaat agaatcttta caaataagaa     180
tatacacttc tgcttaggat gataattgga ggcaagtgaa tcctgagcgt gatttgataa     240
tgacctaata atgatgggtt ttatttccag                                       270

<210> SEQ ID NO 5
<211> LENGTH: 23
<212> TYPE: DNA
<213> ORGANISM: Artificial
<220> FEATURE:
<223> OTHER INFORMATION: Chemically Synthesized

<400> SEQUENCE: 5
taatacgact cactataggg aga                                              23

<210> SEQ ID NO 6
<211> LENGTH: 23
<212> TYPE: DNA
<213> ORGANISM: Artificial
<220> FEATURE:
<223> OTHER INFORMATION: Chemically Synthesized
<220> FEATURE:
<221> NAME/KEY: misc_feature
<222> LOCATION: (22)..(22)

<223> OTHER INFORMATION: n is a, c, g, or t

<400> SEQUENCE: 6
atttaggtga cactatagaa gng                                                23

<210> SEQ ID NO 7
<211> LENGTH: 23
<212> TYPE: DNA
<213> ORGANISM: Artificial
<220> FEATURE:
<223> OTHER INFORMATION: Chemically Synthesized

<400> SEQUENCE: 7
aattaaccct cactaaaggg aga                                                23

<210> SEQ ID NO 8
<211> LENGTH: 81
<212> TYPE: DNA
<213> ORGANISM: Artificial
<220> FEATURE:
<223> OTHER INFORMATION: Chemically Synthesized

<400> SEQUENCE: 8
atgaagtggg taacctttct cctcctcctc ttcgtctccg gctctgcttt ttccaggggt        60
gtgtttcgcc gagaagcacc c                                                  81

<210> SEQ ID NO 9
<211> LENGTH: 82
<212> TYPE: DNA
<213> ORGANISM: Artificial
<220> FEATURE:
<223> OTHER INFORMATION: Chemically Synthesized

<400> SEQUENCE: 9
gggtgcttct cggcgaaaca caccctgga aaaagcagag ccggagacga agaggaggag         60
gagaaaggtt acccacttca tg                                                 82

<210> SEQ ID NO 10
<211> LENGTH: 81
<212> TYPE: DNA
<213> ORGANISM: Artificial
<220> FEATURE:
<223> OTHER INFORMATION: Chemically Synthesized

<400> SEQUENCE: 10
atgaagtggg taacctttat ttccttctt tttctcttta gctcggctta ttccaggggt         60
gtgtttcgtc gagatgcacc c                                                  81

<210> SEQ ID NO 11
<211> LENGTH: 82
<212> TYPE: DNA
<213> ORGANISM: Artificial
<220> FEATURE:
<223> OTHER INFORMATION: Chemically Synthesized

<400> SEQUENCE: 11
gggtgcatct cgacgaaaca caccctgga ataagccgag ctaaagagaa aagaaggga          60 aataaaggtt acccacttca tg                                                 82

<210> SEQ ID NO 12
<211> LENGTH: 24
<212> TYPE: DNA
<213> ORGANISM: Artificial
<220> FEATURE:

<223> OTHER INFORMATION: Chemically Synthesized

<400> SEQUENCE: 12
ccccagagcc cctgggatcg agtg                                              24

<210> SEQ ID NO 13
<211> LENGTH: 42
<212> TYPE: DNA
<213> ORGANISM: Artificial
<220> FEATURE:
<223> OTHER INFORMATION: Chemically Synthesized

<400> SEQUENCE: 13
ctagaagctt cccactttgg aaacgtttat tctgagcacc gg                          42

<210> SEQ ID NO 14
<211> LENGTH: 32
<212> TYPE: DNA
<213> ORGANISM: Artificial
<220> FEATURE:
<223> OTHER INFORMATION: Chemically Synthesized

<400> SEQUENCE: 14
ctagggatcc gttttatgtt ttttcatctc tg                                     32

<210> SEQ ID NO 15
<211> LENGTH: 35
<212> TYPE: DNA
<213> ORGANISM: Artificial
<220> FEATURE:
<223> OTHER INFORMATION: Chemically Synthesized

<400> SEQUENCE: 15
ctaggcggcc gcaggccttt gaaatgttgt tctcc                                  35

<210> SEQ ID NO 16
<211> LENGTH: 34
<212> TYPE: DNA
<213> ORGANISM: Artificial
<220> FEATURE:
<223> OTHER INFORMATION: Chemically Synthesized

<400> SEQUENCE: 16
ctaggctagc acctttccta tcaaccccac tagc                                   34

<210> SEQ ID NO 17
<211> LENGTH: 35
<212> TYPE: DNA
<213> ORGANISM: Artificial
<220> FEATURE:
<223> OTHER INFORMATION: Chemically Synthesized

<400> SEQUENCE: 17
ctaggcggcc gcaggccttt gaaatgttgt tctcc                                  35

<210> SEQ ID NO 18
<211> LENGTH: 23
<212> TYPE: DNA
<213> ORGANISM: Artificial
<220> FEATURE:
<223> OTHER INFORMATION: Chemically Synthesized

<400> SEQUENCE: 18
acctttctcc tcctcctctt cgt                                               23

<210> SEQ ID NO 19

```
<211> LENGTH: 23
<212> TYPE: DNA
<213> ORGANISM: Artificial
<220> FEATURE:
<223> OTHER INFORMATION: Chemically Synthesized

<400> SEQUENCE: 19
acatagtctc tgccgctgtc ttt                                              23

<210> SEQ ID NO 20
<211> LENGTH: 897
<212> TYPE: DNA
<213> ORGANISM: Artificial
<220> FEATURE:
<223> OTHER INFORMATION: Chemically Synthesized

<400> SEQUENCE: 20
agagactgcg agaaggaggt cccccacggc ccttcaggat gaaagctgcg gtgctgacct      60
tggccgtgct cttcctgacg gggagccagg ctcggcattt ctggcagcaa gatgaacccc    120
cccagagccc ctgggatcga gtgaaggacc tggccactgt gtacgtggat gtgctcaaag    180
acagcggcag agactatgtg tcccagtttg aaggctccgc cttgggaaaa cagctaaacc    240
taaagctcct tgacaactgg gacagcgtga cctccaccct cagcaagctg cgcgaacagc    300
tcggccctgt gacccaggag ttctgggata acctggaaaa ggagacagag ggcctgaggc    360
aggagatgag caaggatctg gaggaggtga aggccaaggt gcagccctac ctggacgact    420
tccagaagaa gtggcaggag gagatggagc tctaccgcca gaaggtggag ccgctgcgcg    480
cagagctcca gagggcgcg cgccagaagc tgcacgagct gcaagagaag ctgagcccac    540
tgggcgagga gatgcgcgac cgcgcgcgcg cccatgtgga cgcgctgcgc acgcatctgg    600 cccctacag cgacgagctg cgccagcgct tggccgcgcg ccttgaggct ctcaaggaga    660
acggcggcgc cagactggcc gagtaccacg ccaaggccac cgagcatctg agcacgctca    720
gcgagaaggc caagcccgcg ctcgaggacc tccgccaagg cctgctgccc gtgctggaga    780
gcttcaaggt cagcttcctg agcgctctcg aggagtacac taagaagctc aacacccagt    840
gaggcgcccg ccgccgcccc ccttcccggt gctcagaata acgtttccaa aagtggg       897

<210> SEQ ID NO 21
<211> LENGTH: 38
<212> TYPE: DNA
<213> ORGANISM: Artificial
<220> FEATURE:
<223> OTHER INFORMATION: Chemically Synthesized

<400> SEQUENCE: 21
ctaggctagc agagactgcg agaaggaggt cccccacg                              38

<210> SEQ ID NO 22
<211> LENGTH: 6
<212> TYPE: DNA
<213> ORGANISM: Artificial
<220> FEATURE:
<223> OTHER INFORMATION: Chemically Synthesized

<400> SEQUENCE: 22 gctagc                                                                 6

<210> SEQ ID NO 23
<211> LENGTH: 6
<212> TYPE: DNA
<213> ORGANISM: Artificial
<220> FEATURE:
```

<223> OTHER INFORMATION: Chemically Synthesized

<400> SEQUENCE: 23 aagctt                                                                    6

<210> SEQ ID NO 24
<211> LENGTH: 42
<212> TYPE: DNA
<213> ORGANISM: Artificial
<220> FEATURE:
<223> OTHER INFORMATION: Chemically Synthesized

<400> SEQUENCE: 24
ctagaagctt cccactttgg aaacgtttat tctgagcacc gg                            42

<210> SEQ ID NO 25
<211> LENGTH: 15
<212> TYPE: DNA
<213> ORGANISM: Artificial
<220> FEATURE:
<223> OTHER INFORMATION: Chemically Synthesized

<400> SEQUENCE: 25
gagatgcgcg accgc                                                         15

<210> SEQ ID NO 26
<211> LENGTH: 59
<212> TYPE: DNA
<213> ORGANISM: Artificial
<220> FEATURE:
<223> OTHER INFORMATION: Chemically Synthesized

<400> SEQUENCE: 26
ctagcacgag ctgcaagaga agctgagccc actgggcgag gagatgtgcg accgcgcgc         59

<210> SEQ ID NO 27
<211> LENGTH: 15
<212> TYPE: DNA
<213> ORGANISM: Artificial
<220> FEATURE:
<223> OTHER INFORMATION: Chemically Synthesized

<400> SEQUENCE: 27
gagatgtgcg accgc                                                         15

<210> SEQ ID NO 28
<211> LENGTH: 6
<212> TYPE: DNA
<213> ORGANISM: Artificial
<220> FEATURE:
<223> OTHER INFORMATION: Chemically Synthesized

<400> SEQUENCE: 28 gctagc                                                                    6

<210> SEQ ID NO 29
<211> LENGTH: 6
<212> TYPE: DNA
<213> ORGANISM: Artificial
<220> FEATURE:
<223> OTHER INFORMATION: Chemically Synthesized

<400> SEQUENCE: 29 ccgcgg                                                                    6

<210> SEQ ID NO 30

<211> LENGTH: 47
<212> TYPE: DNA
<213> ORGANISM: Artificial
<220> FEATURE:
<223> OTHER INFORMATION: Chemically Synthesized

<400> SEQUENCE: 30
tactaactca attttttttt tttttttttt aattaacagc ccctaaa        47

<210> SEQ ID NO 31
<211> LENGTH: 9
<212> TYPE: DNA
<213> ORGANISM: Artificial
<220> FEATURE:
<223> OTHER INFORMATION: Chemically Synthesized

<400> SEQUENCE: 31 ccggtgagt        9

<210> SEQ ID NO 32
<211> LENGTH: 6
<212> TYPE: DNA
<213> ORGANISM: Artificial
<220> FEATURE:
<223> OTHER INFORMATION: Chemically Synthesized

<400> SEQUENCE: 32 cagaag        6

<210> SEQ ID NO 33
<211> LENGTH: 9
<212> TYPE: DNA
<213> ORGANISM: Artificial
<220> FEATURE:
<223> OTHER INFORMATION: Chemically Synthesized

<400> SEQUENCE: 33 caagtaagg        9

<210> SEQ ID NO 34
<211> LENGTH: 6
<212> TYPE: DNA
<213> ORGANISM: Artificial
<220> FEATURE:
<223> OTHER INFORMATION: Chemically Synthesized

<400> SEQUENCE: 34 tagaag        6

<210> SEQ ID NO 35
<211> LENGTH: 9
<212> TYPE: DNA
<213> ORGANISM: Artificial
<220> FEATURE:
<223> OTHER INFORMATION: Chemically Synthesized

<400> SEQUENCE: 35 aaggtatgg        9

<210> SEQ ID NO 36
<211> LENGTH: 6
<212> TYPE: DNA
<213> ORGANISM: Artificial
<220> FEATURE:
<223> OTHER INFORMATION: Chemically Synthesized

<400> SEQUENCE: 36 gctagc                                                                  6

<210> SEQ ID NO 37
<211> LENGTH: 6
<212> TYPE: DNA
<213> ORGANISM: Artificial
<220> FEATURE:
<223> OTHER INFORMATION: Chemically Synthesized

<400> SEQUENCE: 37 ccgcgg                                                                  6

<210> SEQ ID NO 38
<211> LENGTH: 47
<212> TYPE: DNA
<213> ORGANISM: Artificial
<220> FEATURE:
<223> OTHER INFORMATION: Chemically Synthesized

<400> SEQUENCE: 38
tactaactca attttttttt tttttttttt aattaacagc ccctaaa                    47

<210> SEQ ID NO 39
<211> LENGTH: 54
<212> TYPE: DNA
<213> ORGANISM: Artificial
<220> FEATURE:
<223> OTHER INFORMATION: Chemically Synthesized

<400> SEQUENCE: 39
atgaaagctg cggtgctgac cttggccgtg ctcttcctga cggggagcca ggct            54

<210> SEQ ID NO 40
<211> LENGTH: 18
<212> TYPE: DNA
<213> ORGANISM: Artificial
<220> FEATURE:
<223> OTHER INFORMATION: Chemically Synthesized

<400> SEQUENCE: 40
cggcatttct ggcagcaa                                                    18

<210> SEQ ID NO 41
<211> LENGTH: 66
<212> TYPE: DNA
<213> ORGANISM: Artificial
<220> FEATURE:
<223> OTHER INFORMATION: Chemically Synthesized

<400> SEQUENCE: 41 gatgaaccccc cccagagccc ctgggatcga gtgaaggacc tggccactgt gtacgtggat    60
gtgctc                                                                 66

<210> SEQ ID NO 42
<211> LENGTH: 22
<212> TYPE: DNA
<213> ORGANISM: Artificial
<220> FEATURE:
<223> OTHER INFORMATION: Chemically Synthesized

<400> SEQUENCE: 42
ccgagaagca ccccccccaga gc                                              22

<210> SEQ ID NO 43
<211> LENGTH: 859
<212> TYPE: DNA

```
<213> ORGANISM: Artificial
<220> FEATURE:
<223> OTHER INFORMATION: Chemically Synthesized

<400> SEQUENCE: 43
atgaagtggg taacctttat ttcccttctt tttctcttta gctcggctta ttccaggggt      60
gtgtttcgtc gagatgcacc ccccagagc cctgggatc gagtgaagga cctggccact      120
gtgtacgtga tgtgctcaa agacagcggc agagactatg tgtcccagtt tgaaggctcc      180
gccttgggaa aacagctaaa cctaaagctc cttgacaact gggacagcgt gacctccacc      240
ttcagcaagc tgcgcgaaca gctcggcccct gtgacccagg agttctggga taacctggaa      300
aaggagacag agggcctgag gcaggagatg agcaaggatc tggaggaggt gaaggccaag      360
gtgcagccct acctggacga cttccagaag aagtggcagg aggagatgga gctctaccgc      420
cagaaggtgg agccgctgcg cgcagagctc caagagggcg cgcgccagaa gctgcacgag      480
ctgcaagaga gctgagccc actgggcgag gagatgcgcg accgcgcgcg cgcccatgtg      540
gacgcgctgc gcacgcatct ggccccctac agcgacgagc tgcgccagcg cttggccgcg      600
cgccttgagg ctctcaagga gaacggcggc gccagactgg ccgagtacca cgccaaggcc      660
accgagcatc tgagcacgct cagcgagaag gccaagcccg cgctcgagga cctccgccaa      720
ggcctgctgc ccgtgctgga gagcttcaag gtcagcttcc tgagcgctct cgaggagtac      780
actaagaagc tcaacacccca gtgaggcgcc cgccgccgcc cccttcccg gtgctcagaa      840 taaacgtttc caaagtggg                                                     859

<210> SEQ ID NO 44
<211> LENGTH: 66
<212> TYPE: DNA
<213> ORGANISM: Artificial
<220> FEATURE:
<223> OTHER INFORMATION: Chemically Synthesized

<400> SEQUENCE: 44
ggaaacagac aagagtgagg ttgctcatcg gtttaaagat ttgggagaag aaaatttcaa      60
agcctt                                                                   66

<210> SEQ ID NO 45
<211> LENGTH: 209
<212> TYPE: DNA
<213> ORGANISM: Artificial
<220> FEATURE:
<223> OTHER INFORMATION: Chemically Synthesized

<400> SEQUENCE: 45
atggctcagt caaagcacgg tctaacaaaa gaaatgacaa tgaaataccg tatggaaggg      60
tgcgtcgatg gacataaatt tgtgatcacg ggagagggca ttggatatcc gttcaaaggg      120
aaacaggcta ttaatctgtg tgtggtcgaa ggtggaccat gccatttgc cgaagacata      180 ttgtcagctg cctttatgta cggaaacag                                          209

<210> SEQ ID NO 46
<211> LENGTH: 700
<212> TYPE: DNA
<213> ORGANISM: Artificial
<220> FEATURE:
<223> OTHER INFORMATION: Chemically Synthesized

<400> SEQUENCE: 46
gtaagaaatc cattttctca ttgttcaact tttattctat tttcccagta aaataaagtt      60
```

-continued

| | |
|---|---|
| ttagtaaact ctgcatcttt aagaattat tttggcattt atttctaaaa tggcatagta | 120 |
| ttttgtattt gtgaagtctt acaaggttat cttattaata aaattcaaac atcctaggta | 180 |
| aaaaaaaaaa aaggtcagaa ttgtttagtg actgtaattt tcttttgcgc actaaggaaa | 240 |
| gtgcaaagta acttagagtg actgaaactt cacagaatag ggttgaagat tgaattcata | 300 |
| actatcccaa agacctatcc attgcactat gctttattta aaaccacaa aacctgtgct | 360 |
| gttgatctca taaatagaac ttgtatttat atttattttc attttagtct gtcttcttgg | 420 |
| ttgctgttga tagacactaa aagagtatta gatattatct aagtttgaat ataaggctat | 480 |
| aaatatttaa taattttaa aatagtattc ttggtaattg aattattctt ctgtttaaag | 540 |
| gcagaagaaa taattgaaca tcatcctgag tttttctgta ggaatcagag cccaatattt | 600 |
| tgaaacaaat gcataatcta agtcaaatgg aaagaaatat aaaaagtaac attattactt | 660 |
| cttgttttct tcagtattta acaatccttt tttttcttcc | 700 |

<210> SEQ ID NO 47
<211> LENGTH: 67
<212> TYPE: DNA
<213> ORGANISM: Artificial
<220> FEATURE:
<223> OTHER INFORMATION: Chemically Synthesized

<400> SEQUENCE: 47

| | |
|---|---|
| cttgcccaga caagagtgag gttgctcatc ggtttaaaga tttgggagaa gaaaatttca | 60 |
| aagcctt | 67 |

<210> SEQ ID NO 48
<211> LENGTH: 79
<212> TYPE: DNA
<213> ORGANISM: Artificial
<220> FEATURE:
<223> OTHER INFORMATION: Chemically Synthesized

<400> SEQUENCE: 48

| | |
|---|---|
| atgaagtggg taacctttct cctcctcctc ttcgtctccg gctctgcttt ttccaggggt | 60 |
| gtgtttcgcc gagaagcac | 79 |

<210> SEQ ID NO 49
<211> LENGTH: 6
<212> TYPE: DNA
<213> ORGANISM: Artificial
<220> FEATURE:
<223> OTHER INFORMATION: Chemically Synthesized

<400> SEQUENCE: 49

| | |
|---|---|
| gctagc | 6 |

<210> SEQ ID NO 50
<211> LENGTH: 43
<212> TYPE: DNA
<213> ORGANISM: Artificial
<220> FEATURE:
<223> OTHER INFORMATION: Chemically Synthesized

<400> SEQUENCE: 50

| | |
|---|---|
| ccgcggacga tctcatattc tatcgtcgaa tactaactca att | 43 |

<210> SEQ ID NO 51
<211> LENGTH: 39
<212> TYPE: DNA
<213> ORGANISM: Artificial
<220> FEATURE:

<223> OTHER INFORMATION: Chemically Synthesized

<400> SEQUENCE: 51
tttttttttt tttttttaatt aacagccccc cagagcccc          39

<210> SEQ ID NO 52
<211> LENGTH: 52
<212> TYPE: DNA
<213> ORGANISM: Artificial
<220> FEATURE:
<223> OTHER INFORMATION: Chemically Synthesized

<400> SEQUENCE: 52
gggtgtgttt cgccgagaag cacccccca gagcccctgg gatcgagtga ag          52

<210> SEQ ID NO 53
<211> LENGTH: 54
<212> TYPE: DNA
<213> ORGANISM: Artificial
<220> FEATURE:
<223> OTHER INFORMATION: Chemically Synthesized

<400> SEQUENCE: 53
aggggtgtgt ttcgccgaga agcaccccc cagagcccct gggatcgagt gaag          54

<210> SEQ ID NO 54
<211> LENGTH: 64
<212> TYPE: DNA
<213> ORGANISM: Artificial
<220> FEATURE:
<223> OTHER INFORMATION: Chemically Synthesized
<220> FEATURE:
<221> NAME/KEY: misc_feature
<222> LOCATION: (1)..(7)
<223> OTHER INFORMATION: n is a, c, g, or t

<400> SEQUENCE: 54
nnnnnnnttt tttccagggg tgtgtttcgc cgagaagcac cccccagag cccctgggat          60 cgag          64

<210> SEQ ID NO 55
<211> LENGTH: 79
<212> TYPE: DNA
<213> ORGANISM: Artificial
<220> FEATURE:
<223> OTHER INFORMATION: Chemically Synthesized

<400> SEQUENCE: 55
atgaagtggg taacctttat ttcccttctt tttctcttta gctcggctta ttccaggggt          60
gtgtttcgtc gagatgcac          79

<210> SEQ ID NO 56
<211> LENGTH: 42
<212> TYPE: DNA
<213> ORGANISM: Artificial
<220> FEATURE:
<223> OTHER INFORMATION: Chemically Synthesized

<400> SEQUENCE: 56
cggcatttct ggcagcaaga tgaaccccc cagagcccct gg          42

<210> SEQ ID NO 57
<211> LENGTH: 81

-continued

```
<212> TYPE: DNA
<213> ORGANISM: Artificial
<220> FEATURE:
<223> OTHER INFORMATION: Chemically Synthesized

<400> SEQUENCE: 57
atgaaagctg cggtgctgac cttggccgtg ctcttcctga cggggagcca ggctcggcat      60
ttctggcagc aagatgaacc c                                                81
```

EXPRESSION OF APOAI AND VARIANTS THEREOF USING SPLICEOSOME MEDIATED RNA TRANS-SPLICING

CROSS-REFERENCE TO RELATED APPLICATIONS

The present application claims priority to U.S. Provisional Application Nos. 60/538,796, filed Jan. 23, 2004, and 60/584,280, filed Jun. 30, 2004 and is a continuation-in part of U.S. patent application Ser. No. 11/041,155, filed Jan. 21, 2005 and corresponding PCT Application No. US/05/02392 filed Jan. 21, 2005, the disclosures of which are incorporated by reference in their entireties.

1. INTRODUCTION

The present invention provides methods and compositions for generating novel nucleic acid molecules through targeted spliceosome mediated RNA trans-splicing that result in expression of wild type apoAI, apoAI analogues or variants such as, for example, the apoAI Milano variant, or the initial gene product, pre-pro-apoAI. The compositions of the invention include pre-trans-splicing molecules (PTMs) designed to interact with a target precursor messenger RNA molecule (target pre-mRNA) and mediate a trans-splicing reaction resulting in the generation of a novel chimeric RNA molecule (chimeric RNA) capable of encoding the wild type apoAI, apoAI analogues or, variants, such as the Milano variant, or the pre-pro-apoAI. The expression of this protein and incorporation into high density lipoprotein (HDL) results in protection against cardiovascular disorders resulting from plaque build up, i.e., atherosclerosis, strokes and heart attacks.

In particular, the PTMs of the present invention include those genetically engineered to interact with the apoAI target pre-mRNA so as to result in expression of the apoAI Milano variant. In addition, the PTMs of the invention include those genetically engineered to interact with the apoB target pre-mRNA and/or any other selected target pre-mRNAs, so as to result in expression of an apoB/apoAI Milano chimeric protein, thereby reducing apoB expression and producing apoAI Milano function. In addition, the present invention includes the use of other methods such as the trans-splicing of apoAI sequences into highly abundant transcripts, such as albumin pre-messenger RNA to generate increased levels of apoAI. In addition, the present invention includes the use of other methods, such as trans-splicing ribozymes to create apoAI Milano chimeric mRNA and proteins. The compositions of the invention further include recombinant vector systems capable of expressing the PTMs of the invention and cells expressing said PTMs.

The methods of the invention encompass contacting the PTMs of the invention with an apoAI target pre-mRNA, and/or an apoB target pre-mRNA under conditions in which a portion of the PTM is trans-spliced to a portion of the target pre-mRNA to form a mRNA molecule wherein (i) expression of apoAI is substituted with expression of the apoAI Milano variant; (ii) expression of apoB is substituted with expression of an apoB/apoAI Milano chimeric protein and the level of apoB expression is simultaneously reduced and/or (iii) the expression of albumin is substituted with the expression of apoAI or apoAI variant. The methods of the invention also encompass contacting the PTMs of the invention with other target pre-mRNAs, which are highly expressed and encode efficiently secreted liver proteins, under conditions in which a portion of the PTM is trans-spliced to a portion of the target pre-mRNA to form a mRNA molecule wherein expression of the highly expressed protein is substituted with expression of the wild type apoAI, apoAI analogues or Milano variant. The compositions of the present invention may be administered in combination with other cholesterol lowering agents or lipid regulating agents. The methods and compositions of the present invention can be used to prevent or reduce the level of vascular plaque buildup that is normally associated with cardiovascular disease.

The albumin gene is highly expressed in the liver, thereby providing an abundant target pre-mRNA for trans-splicing. The PTMs of the present invention include those genetically engineered to interact with an albumin target pre-mRNA so as to result in expression of wild type apoAI, apoAI analogues or apoAI variants such as the Milano variant. The methods of the invention encompass contacting such PTMs with an albumin target pre-mRNA under conditions in which a portion of the PTM is trans-spliced to a portion of the albumin target pre-mRNA to form a chimeric mRNA molecule wherein expression of albumin is substituted with expression of wild type apoAI, apoAI analogues or apoAI variants such the apoAI Milano variant or pre-pro-apoAI, or an analogue of apoAI.

2. BACKGROUND OF THE INVENTION

2.1. RNA Splicing

DNA sequences in the chromosome are transcribed into pre-mRNAs which contain coding regions (exons) and generally also contain intervening non-coding regions (introns). Introns are removed from pre-mRNAs in a precise process called cis-splicing (Chow et al., 1977, *Cell* 12:1-8; and Berget, S. M. et al., 1977, *Proc. Natl. Acad. Sci. USA* 74:3171-3175). Splicing takes place as a coordinated interaction of several small nuclear ribonucleoprotein particles (snRNP's) and many protein factors that assemble to form an enzymatic complex known as the spliceosome (Moore et al., 1993, in The RNA World, R. F. Gestland and J. F. Atkins eds. (Cold Spring Harbor Laboratory Press, Cold Spring Harbor, N.Y.); Kramer, 1996, *Annu. Rev. Biochem.*, 65:367-404; Staley and Guthrie, 1998, *Cell* 92:315-326).

In most cases, the splicing reaction occurs within the same pre-mRNA molecule, which is termed cis-splicing. Splicing between two independently transcribed pre-mRNAs is termed trans-splicing. Trans-splicing was first discovered in trypanosomes (Sutton & Boothroyd, 1986, *Cell* 47:527; Murphy et al., 1986, *Cell* 47:517) and subsequently in nematodes (Krause & Hirsh, 1987, *Cell* 49:753); flatworms (Rajkovic et al., 1990, *Proc. Natl. Acad. Sci. USA*, 87:8879; Davis et al., 1995, *J. Biol. Chem.* 270:21813) and in plant mitochondria (Malek et al., 1997, *Proc. Natl. Acad. Sci. USA* 94:553). In the parasite *Trypanosoma brucei*, all mRNAs acquire a splice leader (SL) RNA at their 5' termini by trans-splicing. A 5' leader sequence is also trans-spliced onto some genes in *Caenorhabditis elegans*. This mechanism is appropriate for adding a single common sequence to many different transcripts.

The mechanism of splice leader trans-splicing, which is nearly identical to that of conventional cis-splicing, proceeds via two phosphoryl transfer reactions. The first causes the formation of a 2'-5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs which catalyze the trans-splicing reaction, closely resemble their counterparts involved in cis-splicing.

Trans-splicing refers to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al., 1989, *Proc. Natl. Acad. Sci. USA* 86:8020). In addition, trans-splicing of c-myb pre-mRNA has been demonstrated (Vellard, M. et al. *Proc. Natl. Acad. Sci.*, 1992 89:2511-2515) and RNA transcripts from cloned SV40 trans-spliced to each other were detected in cultured cells and nuclear extracts (Eul et al., 1995, *EMBO. J.* 14:3226). However, naturally occurring trans-splicing of mammalian pre-mRNAs is thought to be a rare event (Flouriot G. et al., 2002 *J. Biol. Chem: Finta, C. et al.*, 2002 *J. Biol Chem* 277:5882-5890).

In vitro trans-splicing has been used as a model system to examine the mechanism of splicing by several groups (Konarska & Sharp, 1985, *Cell* 46:165-171 Solnick, 1985, *Cell* 42:157; Chiara & Reed, 1995, *Nature* 375:510; Pasman and Garcia-Blanco, 1996, *Nucleic Acids Res.* 24:1638). Reasonably efficient trans-splicing (30% of cis-spliced analog) was achieved between RNAs capable of base pairing to each other, splicing of RNAs not tethered by base pairing was further diminished by a factor of 10. Other in vitro trans-splicing reactions not requiring obvious RNA-RNA interactions among the substrates were observed by Chiara & Reed (1995, *Nature* 375:510), Bruzik J. P. & Maniatis, T. (1992, *Nature* 360:692) and Bruzik J. P. and Maniatis, T., (1995, *Proc. Natl. Acad. Sci. USA* 92:7056-7059). These reactions occur at relatively low frequencies and require specialized elements, such as a downstream 5' splice site or exonic splicing enhancers.

In addition to splicing mechanisms involving the binding of multiple proteins to the precursor mRNA which then act to correctly cut and join RNA, a third mechanism involves cutting and joining of the RNA by the intron itself, by what are termed catalytic RNA molecules or ribozymes. The cleavage activity of ribozymes has been targeted to specific RNAs by engineering a discrete "hybridization" region into the ribozyme. Upon hybridization to the target RNA, the catalytic region of the ribozyme cleaves the target. It has been suggested that such ribozyme activity would be useful for the inactivation or cleavage of target RNA in vivo, such as for the treatment of human diseases characterized by production of foreign of aberrant RNA. In such instances small RNA molecules are designed to hybridize to the target RNA and by binding to the target RNA prevent translation of the target RNA or cause destruction of the RNA through activation of nucleases. The use of antisense RNA has also been proposed as an alternative mechanism for targeting and destruction of specific RNAs.

Using the *Tetrahymena* group I ribozyme, targeted trans-splicing was demonstrated in *E. coli*. (Sullenger B. A. and Cech. T. R., 1994, *Nature* 341:619-622), in mouse fibroblasts (Jones, J. T. et al., 1996, *Nature Medicine* 2:643-648), human fibroblasts (Phylacton, L. A. et al. *Nature Genetics* 18:378-381) and human erythroid precursors (Lan et al., 1998, *Science* 280:1593-1596). For a review of clinically relevant technologies to modify RNA see Sullenger and Gilboa, 2002 *Nature* 418:252-8. The present invention relates to the use of targeted trans-splicing mediated by native mammalian splicing machinery, i.e., spliceosomes, to reprogram or alter the coding sequence of a targeted mRNA.

U.S. Pat. Nos. 6,083,702, 6,013,487 and 6,280,978 describe the use of PTMs to mediate a trans-splicing reaction by contacting a target precursor mRNA to generate novel chimeric mRNAs.

2.2. Cardiovascular Disease

Cardiovascular disease (CVD) is the most common cause of death in Western societies, and its prevalence is increasing worldwide. One of the strongest predictors of risk is the plasma concentration of high-density lipoprotein (HDL) or apolipoprotein A-1 (apoAI), the major protein component of HDL, which exhibits an inverse relationship with the development of atherosclerosis and coronary heart disease (Sirtori C R et al., 1999, *Atherosclerosis* 142:29-40; Genest J 2003, *J. Inherit. Metab. Dis.* 26:267-287). ApoAI is the major apolipoprotein of HDL and is a relatively abundant plasma protein with a concentration of 1.0-1.5 mg/ml. ApoAI plays an important role in promoting the efflux of excess cholesterol from peripheral cells and tissues for transfer to the liver for excretion, a process called reverse cholesterol transport (RCT). Numerous in vitro and in vivo studies have demonstrated the protective effects of apoAI and HDL against atherosclerosis plaque development (Rubin E M, et al., *Nature*. 1991, 353:265-7; Plump A S et al., 1994 *Proc Natl Acad Sci. USA* 91:9607-11; Paszty C, et al., 1994 *J Clin Invest.* 94:899-903; Duverger N et al., 1996, *Circulation* 94:713-7).

ApoAI Milano is one of a number of naturally occurring variants of wild type apoAI. It was first identified in 1980 in an Italian family (Franceschini G et al., 1980, *J. Clin. Invest.* 66:892-900; Weisgraber K H et al., 1980 *J Clin Invest.* 66:901-907). To date 40 carriers have been identified and all are heterozygous. These carriers have low plasma HDL-cholesterol levels and moderately elevated levels of triglycerides, a condition that is usually associated with high-risk predictors for coronary heart disease. Despite severe reductions in plasma HDL-cholesterol levels and apoAI concentrations, the affected carriers do not develop coronary artery disease. In fact, infusions of the purified recombinant apoAI Milano or expression of apoAI Milano in rabbits and apoE deficient mice show protection against plaque formation and atherosclerosis (Ameli S et al., 1994, *Circulation* 90:1935-41; Soma M R et al., 1995 *Cir. Res.* 76:405-11; Shah P K et al., 1998 *Circulation* 97:780-5; Franceschini G et al., 1999, *Arterioscler Thromb Vasc Biol.* 19:1257-1262; Chiesa G et al., 2002, *Cir. Res.* 90:974-80; Chiesa G and Sirtori C, 2003, *Curr. Opin. Lipdol.* 14:159-163). Results from clinical trials, however have shown more modest levels of reduction. The degree of plaque reduction may be related to the limited number of doses and amounts of protein administered, and/or its duration in the circulation (pharmacokinetics).

Plasma apoAI is a single polypeptide chain of 243 amino acids, whose primary sequence is known (Brewer et al, 1978, *Biochem. Biophys. Res. Commun.* 80:623-630). ApoAI is synthesized as a 267 amino acid precursor in the cell. This preproapolipoproteinA-1 is first intracellularly processed by N-terminal cleavage of 18 amino acids to yield proapolipoproteinA-1, and then further cleavage of 6 amino acids in the plasma or the lymph by the activity of specific proteases to yield mature apolipoproteinA-1. The major structural requirement of the apoAI molecule is believed to be the presence of repeat units of 11 or 22 amino acids, presumed to exist in amphipathic helical conformation (Segrest et al., 1974, *FEBS Lett* 38:247-253). This structure allows for the main biological activities of apoAI, i.e. lipid binding and lecithin:cholesterol acyltransferase (LCAT) activation.

Human apolipoproteinAI Milano (apoAI Milano) is a natural variant of apoAI (Weisgraber et al, 1980, *J. Clin. Invest* 66:901-907). In apoAI Milano the amino acid Arg173 is replaced by the amino acid Cys173. Since apoAI Milano contains one Cys residue per polypeptide chain, it may exist in a monomeric, homodimeric, or heterodimeric form. These forms are chemically interchangeable, and the term apoAI Milano does not, in the present context, discriminate between these forms. On the DNA level the variant form results from a C to T substitution in the gene sequence, i.e. the codon CGC changed to TGC, allowing the translation of a Cys instead of Arg at amino acid position 173. However, this variant of apoAI is one of the most interesting variants, in that apoAI Milano subjects are characterized by a remarkable reduction in HDL-cholesterol level, but without an apparent increased risk of arterial disease (Franceschini et al. 1980, *J. Clin. Invest* 66:892-900).

Another useful variant of apoAI is the Paris variant, where the arginine 151 is replaced with a cysteine.

The systemic infusion of apoAI alone (Miyazaki et al. 1995, *Arterioscler Thromb Vasc Biol.* 15:1882-1888) or of HDL (Badimon et al, 1989, *Lab Invest.* 60:455-461 and *J Clin Invest.* 85:1234-1241, 1990) in experimental animals and initial human clinical studies (Nanjee et al., 1999, *Arterioscler Thromb Vasc Biol.* 19:979-989 and Eriksson et al. 1999, *Circulation* 100:594-598) has been shown to exert significant biochemical changes, as well as to reduce the extent and severity of atherosclerotic lesions.

Human gene therapy may provide a superior approach for achieving plaque reduction by providing prolonged and continuous expression of genes such as wild type apoAI, pre-pro-apoAI, apoAI analogues or variants such as the Milano variant. In the case of conventional gene therapy approaches that add back the entire apoAI cDNA, un-regulated expression of this cDNA may lead to toxicity and ectopic gene expression. These problems could be overcome by utilization of spliceosome mediated RNA trans-splicing into albumin and other liver transcripts to express wild type apoAI, apoAI Milano or other useful apoAI variants.

Similarly, spliceosome mediated RNA trans-splicing may be used to simultaneously reduce the expression of apoB, a major component of low-density lipoprotein, and produce HDL, i.e., express apoAI wild type or the Milano variant or convert other expressed proteins such as albumin to produce apoAI function.

3. SUMMARY OF THE INVENTION

The present invention relates to compositions and methods for generating novel nucleic acid molecules through spliceosome-mediated targeted RNA trans-splicing, ribozyme mediated trans-splicing, or other means of converting mRNA. The compositions of the invention include pre-trans-splicing molecules (hereinafter referred to as "PTMs") designed to interact with a natural target pre-mRNA molecule (hereinafter referred to as "pre-mRNA") and mediate a spliceosomal trans-splicing reaction resulting in the generation of a novel chimeric RNA molecule (hereinafter referred to as "chimeric RNA"). The methods of the invention encompass contacting the PTMs of the invention with a natural target pre-mRNA under conditions in which a portion of the PTM is spliced to the natural pre-mRNA to form a novel chimeric RNA. The PTMs of the invention are genetically engineered so that the novel chimeric RNA resulting from the trans-splicing reaction may encode a protein that provides health benefits. Generally, the target pre-mRNA is chosen because it is expressed within a specific cell type thereby providing a means for targeting expression of the novel chimeric RNA to a selected cell type. For example, PTMs may be targeted to pre-mRNAs expressed in the liver such as apoAI and/or albumin pre-mRNA.

In particular, the compositions of the invention include pre-trans-splicing molecules (hereinafter referred to as "PTMs") designed to interact with an apoAI target pre-mRNA molecule (hereinafter referred to as "apoAI pre-mRNA") and mediate a spliceosomal trans-splicing reaction resulting in the generation of a novel chimeric RNA molecule (hereinafter referred to as "chimeric RNA").

The compositions of the invention further include PTMs designed to interact with albumin target pre-mRNA molecule (hereinafter referred to as "albumin pre-mRNA") and mediate a spliceosomal trans-splicing reaction resulting in the generation of a novel chimeric RNA molecule.

The compositions of the invention further include PTMs designed to interact with an apoB target pre-mRNA molecule (hereinafter referred to as "apoB pre-mRNA") and mediate a spliceosomal trans-splicing reaction resulting in the generation of a novel chimeric RNA molecule.

The compositions of the invention include PTMs designed to interact with an apoAI target pre-mRNA molecule, albumin target pre-mRNA, or an apoB target pre-mRNA or other pre-mRNA targets and mediate a spliceosomal trans-splicing reaction resulting in the generation of a novel chimeric RNA molecule. Such PTMs are designed to produce an apoAI wild-type protein or apoAI variants, including Milano which are useful to protect against atherosclerosis.

The general design, construction and genetic engineering of PTMs and demonstration of their ability to successfully mediate trans-splicing reactions within the cell are described in detail in U.S. Pat. Nos. 6,083,702, 6,013,487 and 6,280,978 as well as patent Ser. Nos. 09/756,095, 09/756,096, 09/756,097 and 09/941,492, the disclosures of which are incorporated by reference in their entirety herein.

The general design, construction and genetic engineering of trans-splicing ribozymes and demonstration of their ability to successfully mediate trans-splicing reactions within the cell are described in detail in and U.S. Pat. Nos. 5,667,969, 5,854,038 and 5,869,254, as well as patent Ser. No. 20030036517, the disclosures of which are incorporated by reference in their entirety herein.

The methods of the invention encompass contacting the PTMs of the invention with an apoAI target pre-mRNA, albumin target pre-mRNA, or apoB target pre-mRNA, or other expressed pre-mRNA targets, under conditions in which a portion of the PTM is spliced to the target pre-mRNA to form a chimeric RNA. The methods of the invention comprise contacting the PTMs of the invention with a cell expressing an apoAI target pre-mRNA, or an apoB target pre-mRNA or other expressed pre-mRNA targets, such as albumin pre-mRNA, under conditions in which the PTM is taken up by the cell and a portion of the PTM is trans-spliced to a portion of the target pre-mRNA to form a novel chimeric RNA molecule that results in expression of the an apoAI Milano or another variants. Alternatively, for example, when targeting the albumin or apoB pre-mRNAs, the novel chimeric RNA may encode a wild type apoAI protein.

Alternatively, nucleic acid molecules encoding the PTMs of the invention may be delivered into a target cell followed by expression of the nucleic acid molecule to form a PTM capable of mediating a trans-splicing reaction. The PTMs of the invention are genetically engineered so that the novel chimeric RNA resulting from the trans-splicing reaction may encode the apoAI Milano variant protein which has been shown to reduce plaque buildup which may be useful in the prevention or treatment of vascular disease. Alternatively, the chimeric mRNA may encode a wild type apoAI protein or apoAI analogues. Thus, the methods and compositions of the invention can be used in gene therapy for the prevention and treatment of vascular disorders resulting from accumulation of plaque which is a risk factor associated with heart attacks and strokes.

4. BRIEF DESCRIPTION OF THE DRAWINGS

FIG. 1. Schematic representation of different trans-splicing reactions. (a) trans-splicing reactions between the target 5' splice site and PTM's 3' splice site, (b) trans-splicing reactions between the target 3' splice site and PTM's 5' splice site and (c) replacement of an internal exon by a double trans-splicing reaction in which the PTM carries both 3' and 5' splice sites. BD, binding domain; BP, branch point sequence; PPT, polypyrimidine tract; and ss, splice sites.

Figure 2:
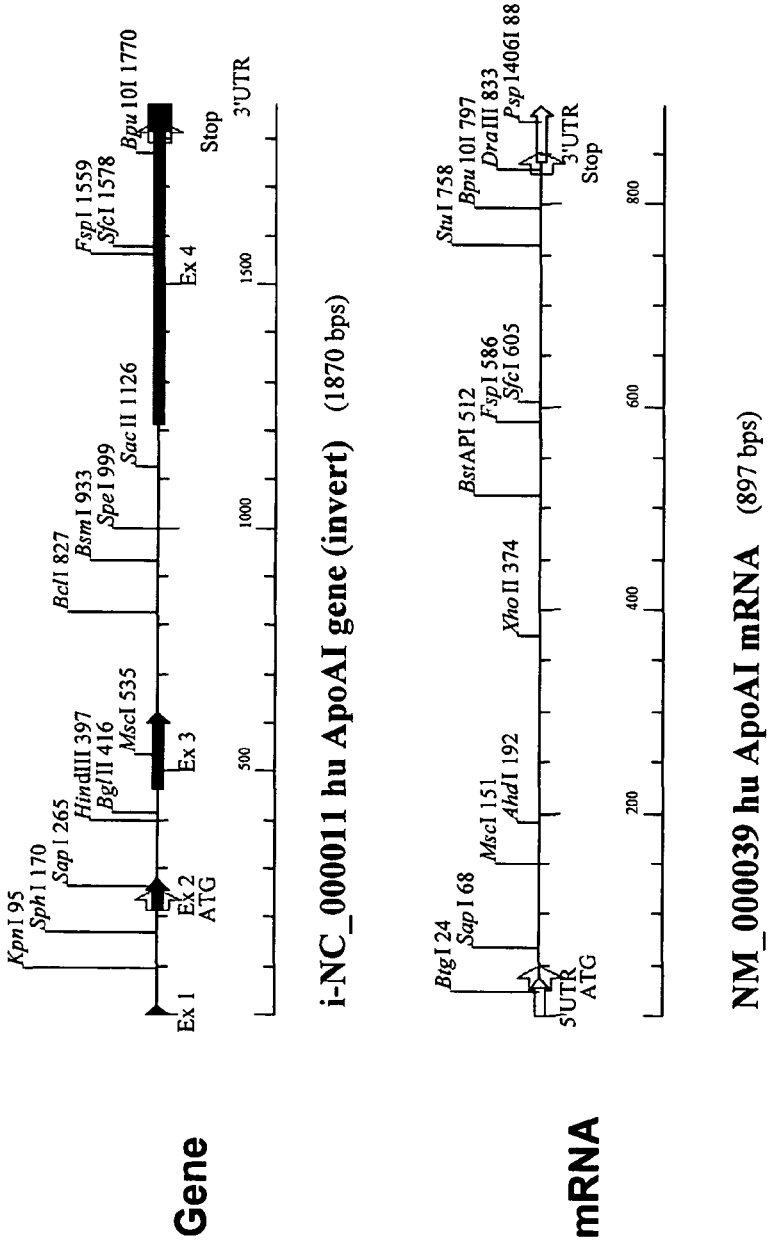

FIG. 2. Human apoAI gene and mRNA. The apoAI gene is 1.87 kb long and comprises 4 exons including a non-coding exon 1. The apoAI mRNA is 897 nucleotides long including a 5' UTR and 3' UTR. The apoAI amino acid sequence consists of 267 residues including a 24 amino acid signal peptide at the N-terminus and the mature protein is a single polypeptide chain with 243 amino acid residues.

Figure 3B:
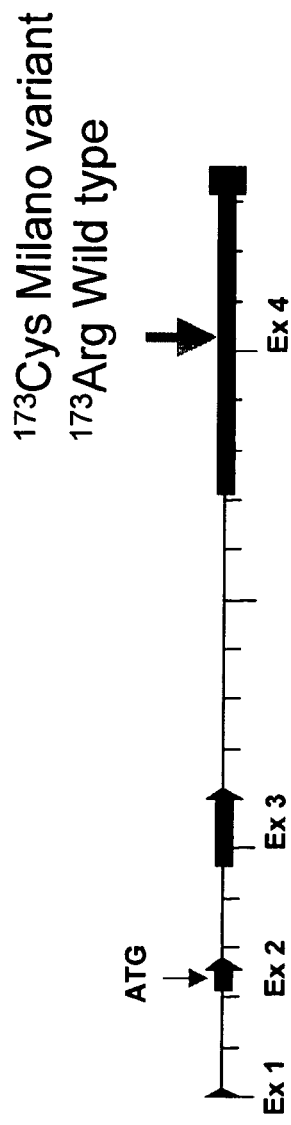

FIG. 3A. Nucleotide and amino acid sequence of wild type apoAI. FIG. 3B. apoAI-Milano variant.

FIG. 3C. Strategy to create apoAI-Milano.

FIG. 4. Target gene and PTM structure. FIG. 4A. Schematic structure of human wild type apoAI full length target gene for in vitro studies. FIG. 4B Schematic structure of human apoAI Milano PTM1 (exon 4).

Figure 5:
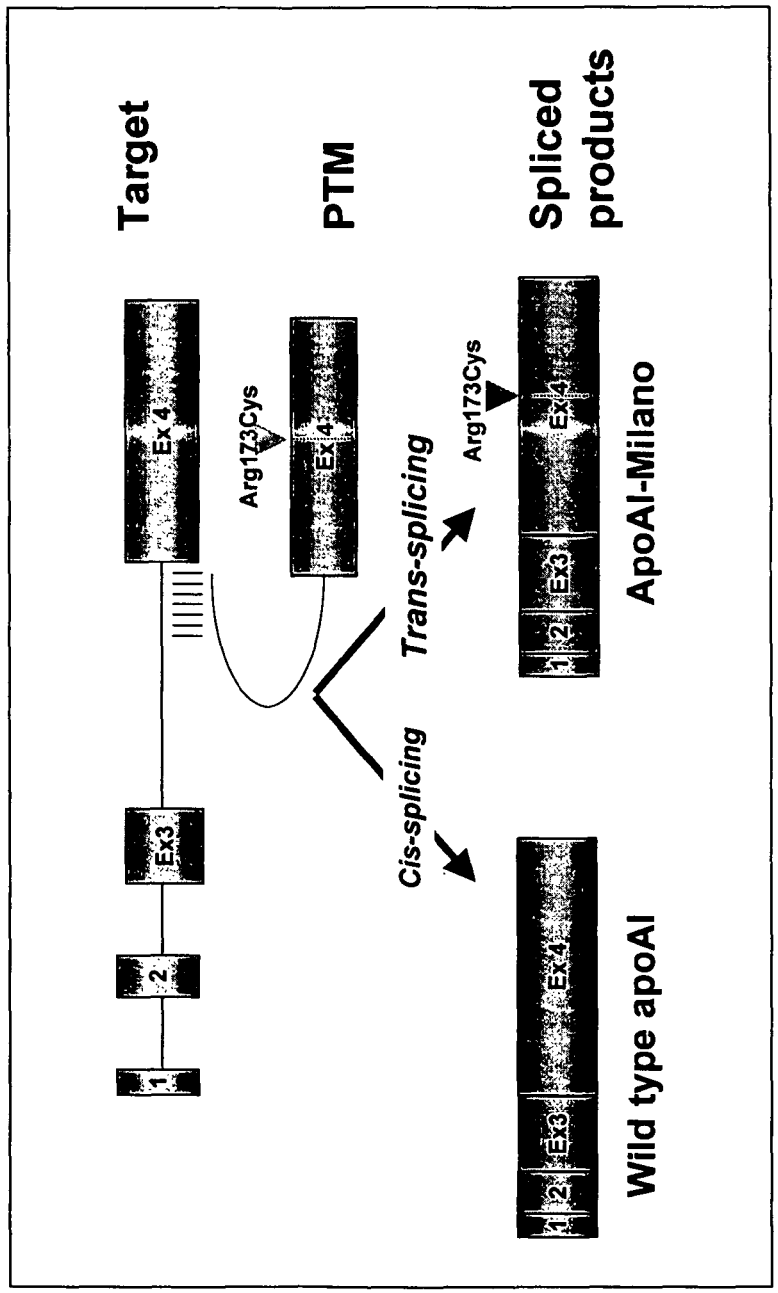

FIG. 5. Schematic illustration of trans-splicing reaction between apoAI target pre mRNA and PTM.

Figure 6:
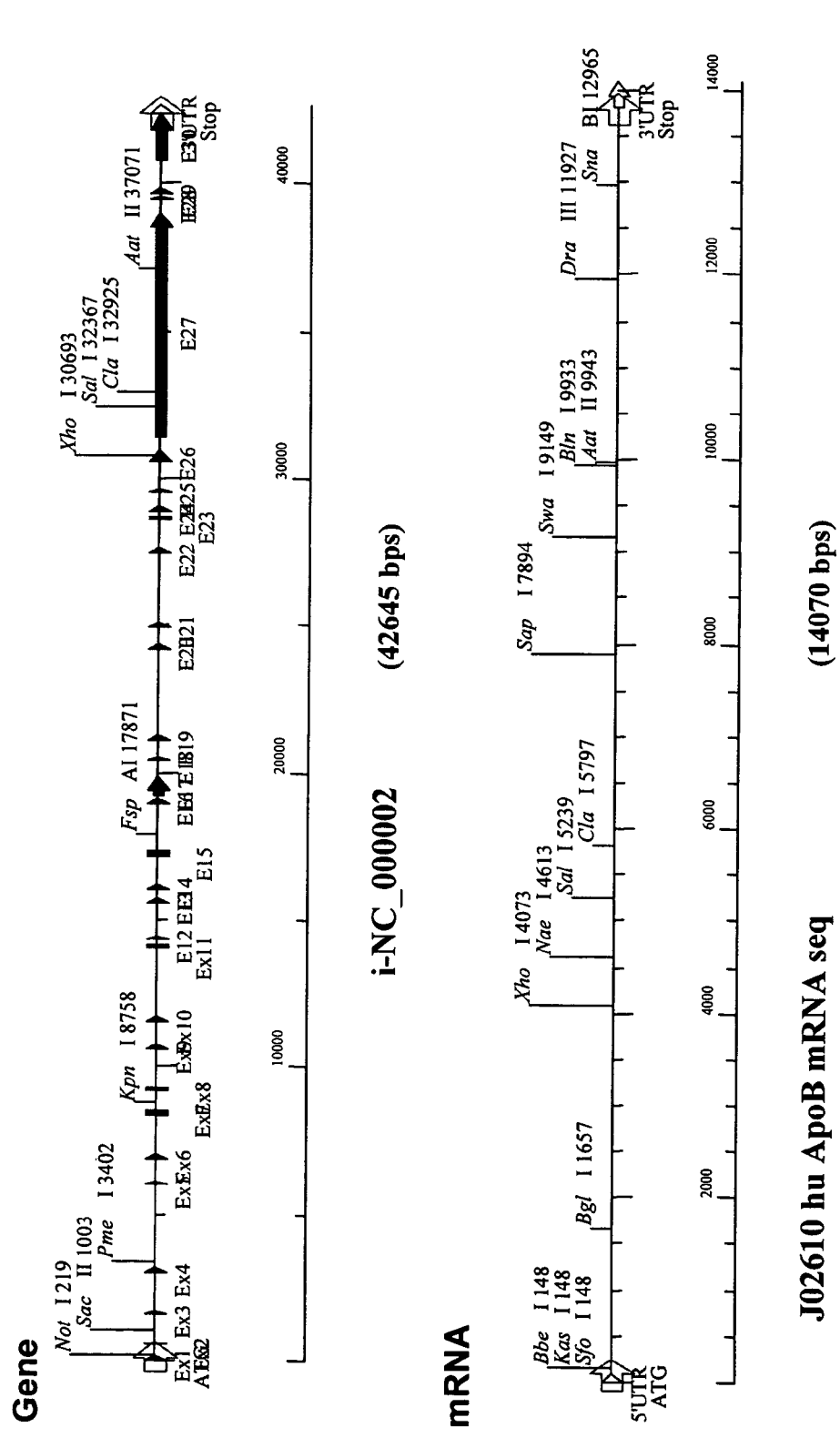

FIG. 6. ApoB-100 gene and mRNA.

Figure 7:
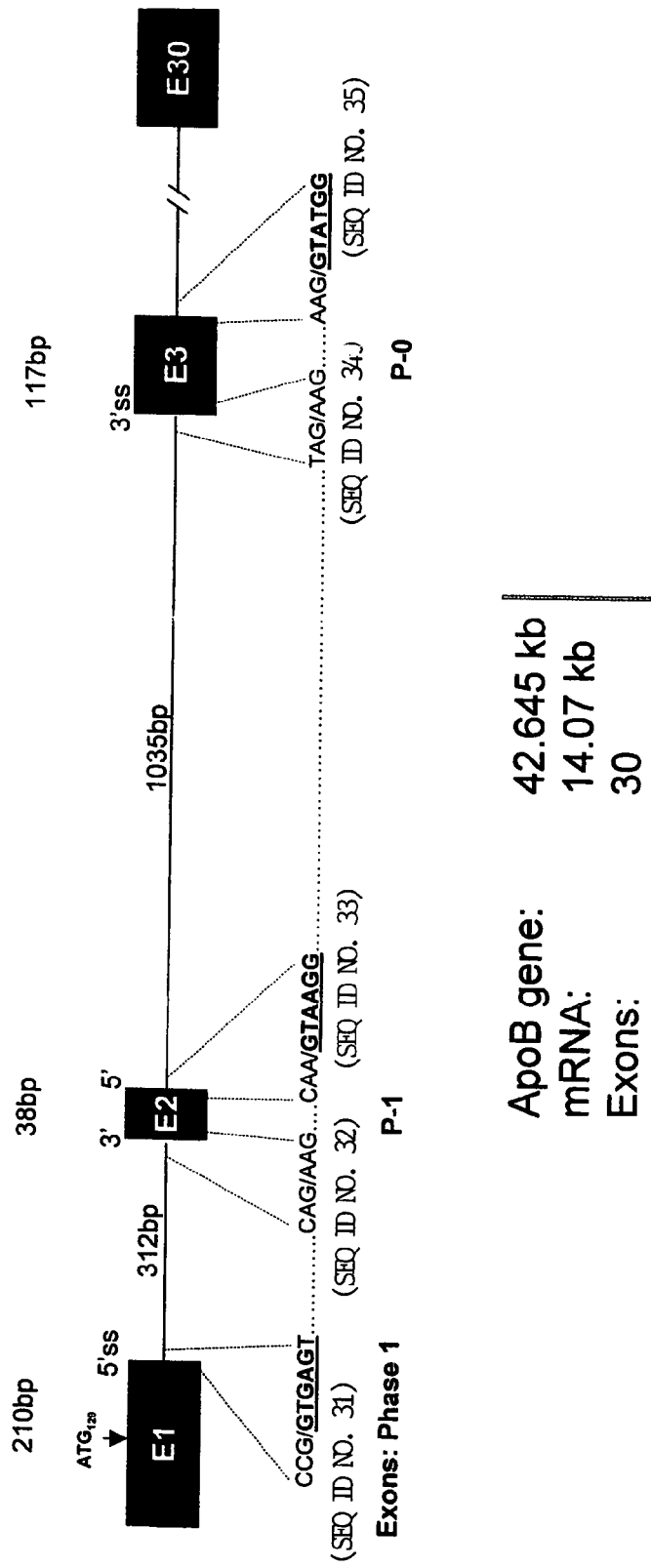

FIG. 7. Schematic structure of ApoB target pre-mRNA.

FIG. 8A. Mini-gene target and PTM structure showing a schematic structure of human apoB mini-gene target for in vitro studies.

FIG. 8B. Mini-gene target and PTM structure showing a schematic structure of human apoAI Milano PTM2.

Figure 9:
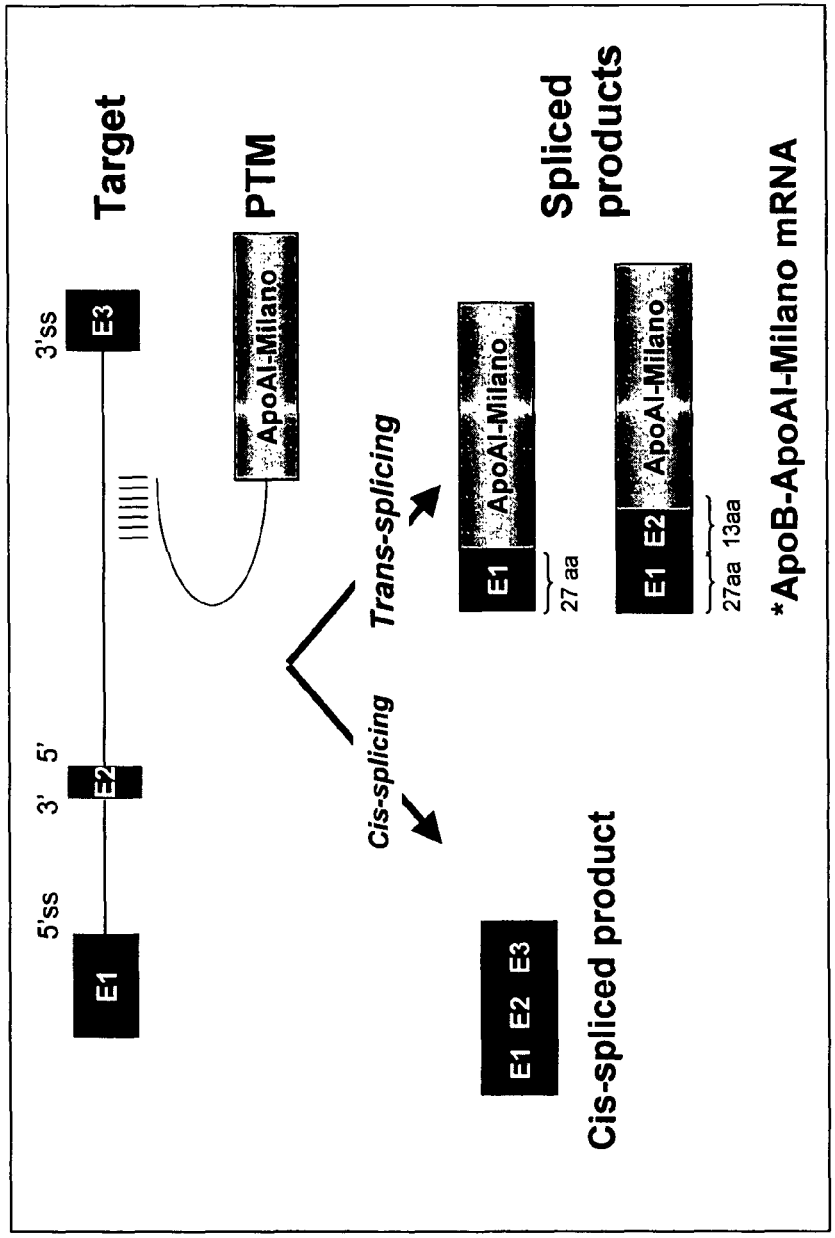

FIG. 9. Schematic illustration of trans-splicing reaction between apoB target pre mRNA and PTM).

FIG. 10. Human Albumin Gene Structure. (See, also Minghetti et al., 1986, J. Biol. Chem. 261:6747-6757).

FIG. 11. Human apoAI.

FIG. 12. Human apoAI Gene and mRNA structural details

Figure 13:
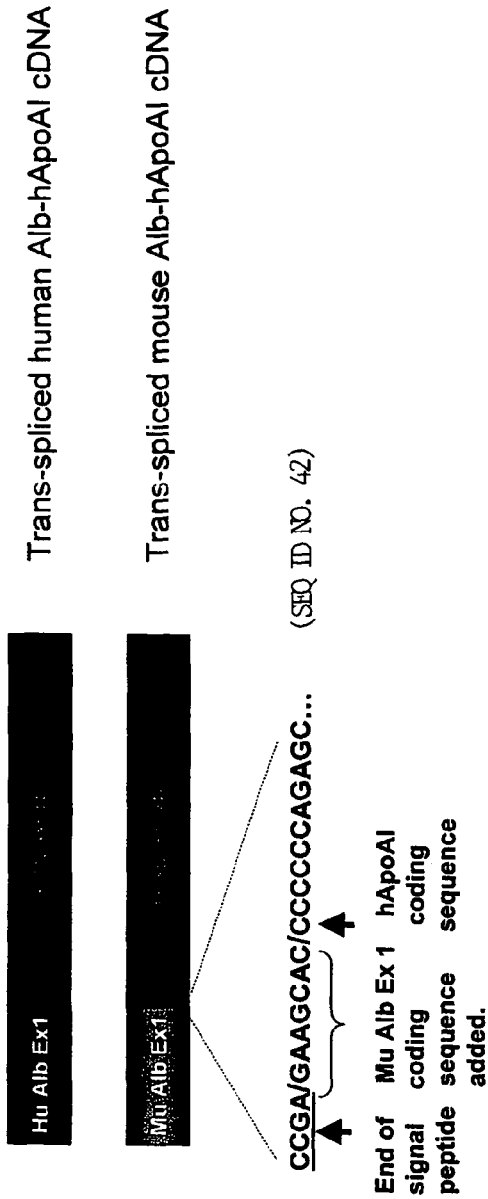

FIG. 13. Schematic illustration of human and mouse albumin exon 1/human apoAI trans-spliced cDNAs.

FIG. 14. Nucleotide sequences of human albumin exon 1/human apoAI (wild type) trans-spliced mRNA. Underlined sequence represents human albumin signal peptide; / indicates junction between albumin and apoAI. ATG and stop codon, TGA are indicated in italics.

FIG. 15. Western Analysis of Mouse and Human Alb/apoAI trans-spliced cDNAs in 293 cells.

FIG. 16. Western Analysis of Mouse and Human Alb/apoAI trans-spliced cDNAs in 293 and HepG2 cells.

FIG. 17. Target Construct for Binding Domain Screen. Schematic structure of 5' GFP-AlbIn1Ex2 target gene for in vitro studies. Target pre-mRNA construct contains partial coding sequence for GFP fluorescent protein followed by 5' splice site, albumin intron 1, 3' acceptor site and albumin exon 2.

FIG. 18. 5' GFP-AlbIn1Ex2 Pre-mRNA Target Sequence. Nucleotide sequence of 5' GFP-AlbIn1Ex2 gene for in vitro studies. Sequences shown in italics indicate first half of the coding sequence for GFP fluorescent protein followed by human albumin intron 1 and exon 2 sequences (underlined). "/" indicates 5' and 3' splice junctions.

Figure 19:
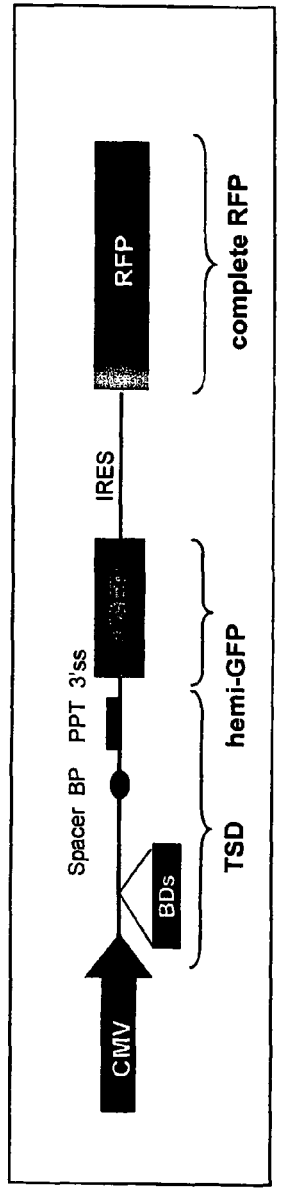

FIG. 19. PTM Cassette Used for Binding Domain Screen. Schematic structure of a prototype PTM expression cassette is shown. It consists of a trans-splicing domain (TSD) followed by a 24 nucleotide spacer, a 3' splice site including the consensus yeast branch point (BP), an extended polypyrimidine tract and the AG splice acceptor site. The TSD was fused to the remaining 3' GFP coding sequence. In addition, the PTM cassette also contain full length coding sequence for a second fluorescent reporter (DsRed2) and the expression is driven by an internal ribosome entry site (IRES) of the encephalomyocarditis virus (ECMV).

FIG. 20. Binding Domain Screening Strategies. (A) high capacity screen and (B) rational binding domain design strategy.

FIG. 21. Schematic of targeted trans-splicing of human apoAI into albumin target pre-mRNA.

Figure 22:
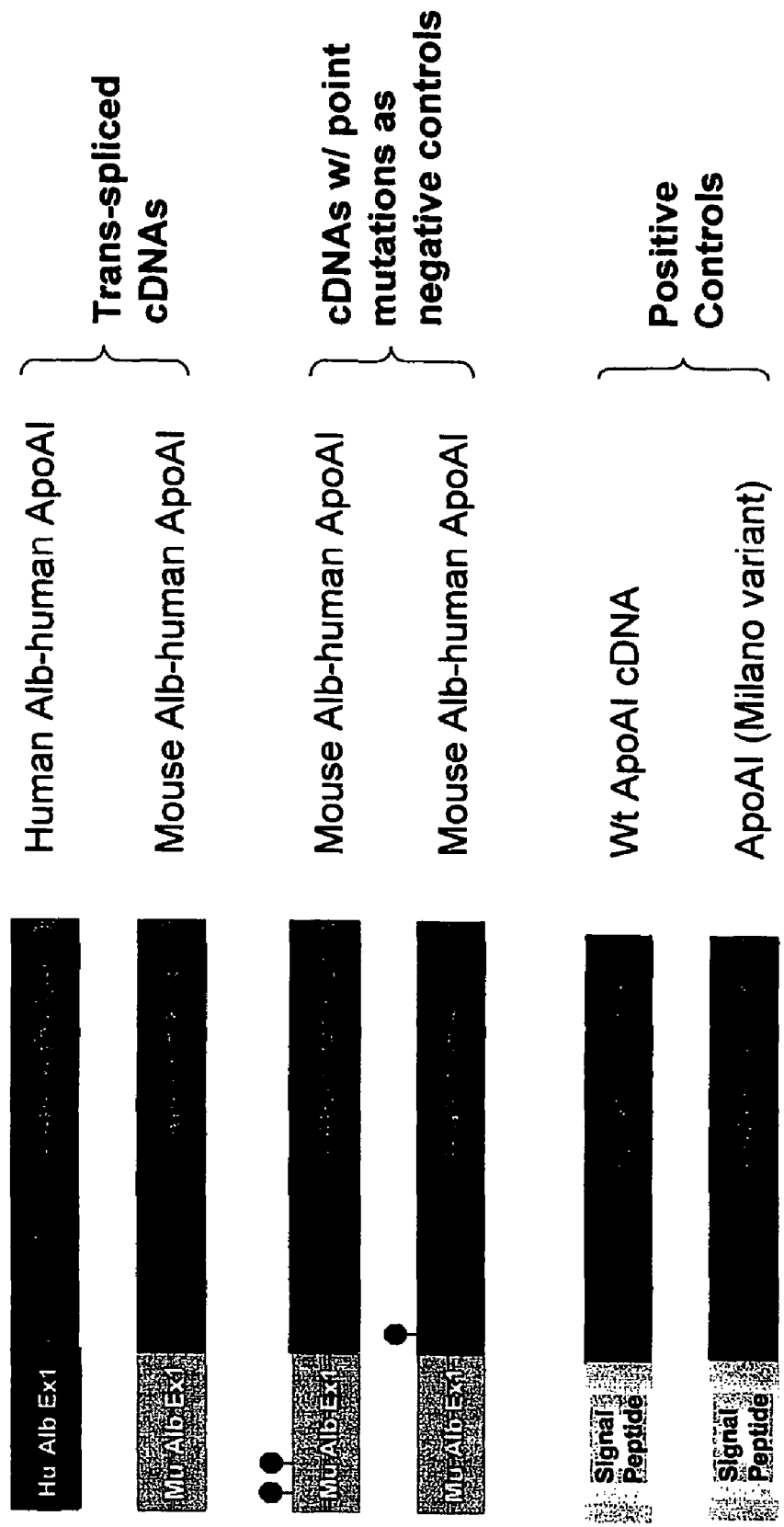

FIG. 22. Schematic of human and mouse apoAI trans-spliced cDNA constructs (test constructs), similar constructs with point (deletion) mutants (negative controls) and wild type human Apo A-I and milano variants (positive controls). ●Indicates point mutuation (deletion) that result in premature termination. No full-length protein was detected on Western blot.

FIG. 23. SDS gels showing human apoAI expression in 293 cells

Figure 24:
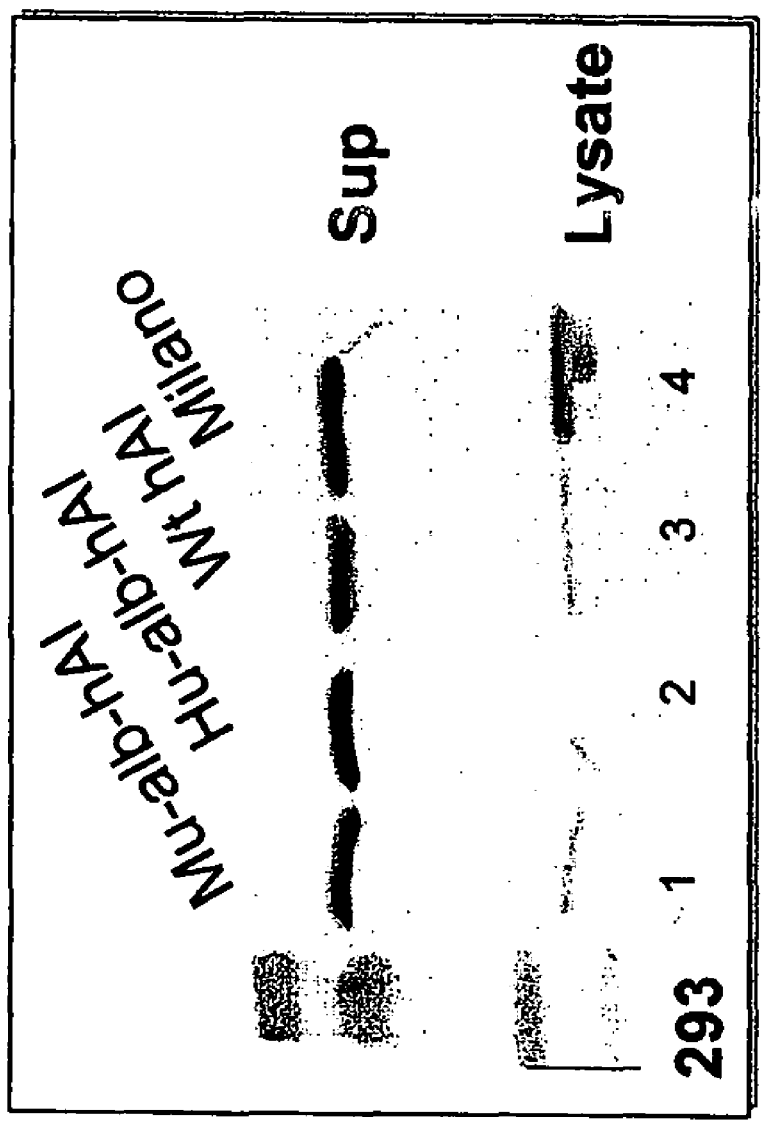

FIG. 24. Western blot showing expression and secretion of mature human apoAI protein in 293 cells. Lane 1, mouse Alb-hAI; lane 2, human Alb-hA1, lane 3, wt Apo A-I and lane 4, milano variant. Upper panel, protein in supernatant and lower panel, protein in cell lysate.

FIG. 25. Cholesterol efflux in 293 cells demonstrating the expression of functional human apoAI protein.

FIG. 26A. Schematic of FACS-based PTM selection strategy.

FIG. 26B. Comparison of high capacity screening (HCS) protocols.

FIG. 27. Schematic of pre-mRNA target used in HCS.

Figure 28:
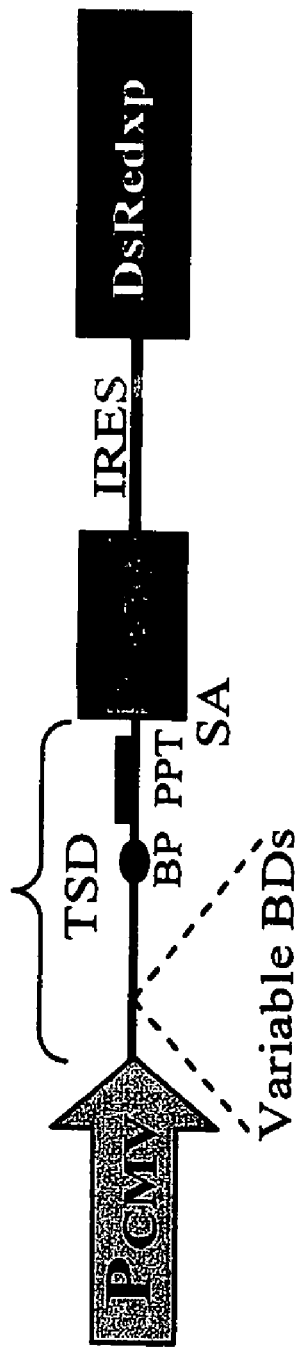

FIG. 28. Schematic of PTM cassette used in HCS. PTM cassette consists of a trans-splice domain including (TSD): variable BDs, short spacer, BP, PPT, 3' half of the coding sequence for zsG, IRES followed by the full length coding sequence for second reporter DsRedExpress. Abbreviations: 3'zsG, 3' half of the zsGreen fluorescent protein coding sequence; IRES, internal ribosome entry site, BD, binding domain; BP, branch point; PPT, polvpyrimitate tract. SA, splice acceptor site.

FIG. 29. PCR analysis of the mouse albumin binding domain (BD) library.

FIG. 30. High capacity screening (HCS) method and summary of results.

FIG. 31. Trans-splicing efficiency of PTMs selected from HCS.

FIG. 32. Bar graph showing trans-splicing efficiency and GFP fluorescence of various PTMs selected from HCS.

FIG. 33. Schematic showing the human apoAI PTM expression cassette used for proof of principle in vitro studies.

FIG. 34. Schematic diagram of the mouse albumin mini-gene pre-mRNA target.

FIG. 35. Trans-splicing of mAlbPTMs into albumin exon 1 in stable cells.

FIG. 36. Western blot analysis of trans-spliced human apoAI protein.

FIG. 37. PTM-mediated trans-splicing into endogenous albumin exon 1 in mice.

Figure 38:
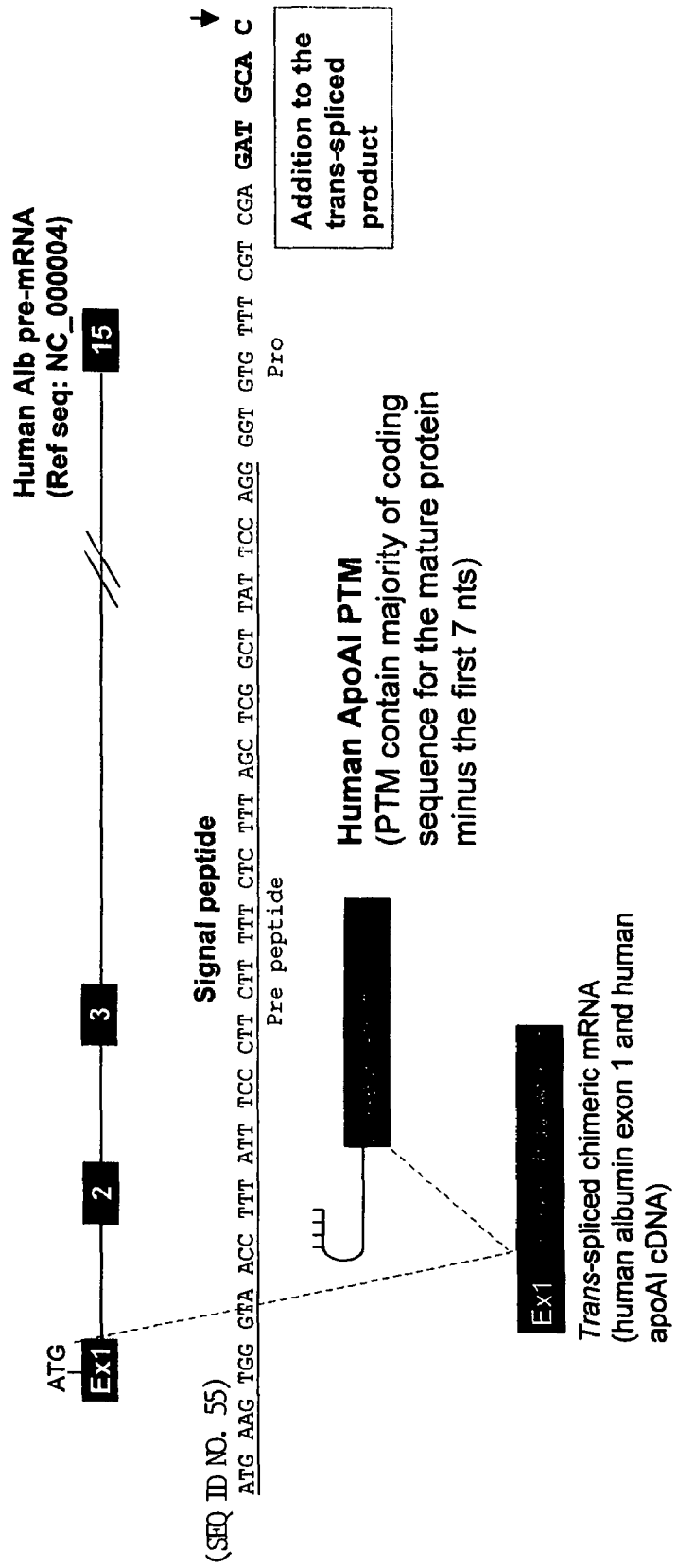

FIG. 38. Schematic diagram showing a human albumin targeting strategy to increase apoAI expression.

FIG. 39 Elimination of albumin sequence in the final trans-spliced product.

Figure 40:
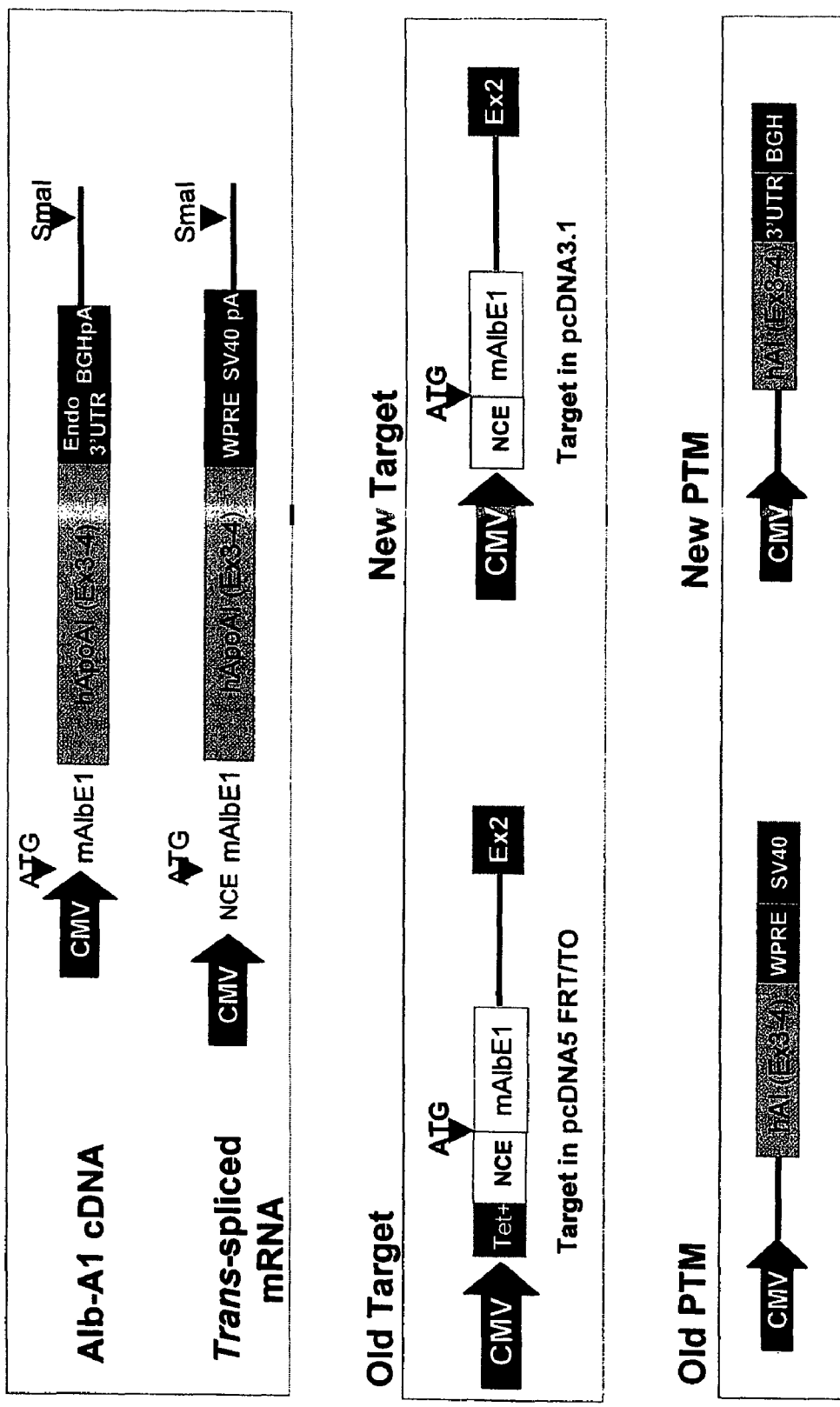

FIG. 40 Schematic drawings of mouse albumin-human apoAI (mAlb-hapoAI) cDNA, trans-spliced mRNA, old and new PTM and targets. NCE, non-coding exon; hAI, human apoAI and Ex, exon.

Figure 41:
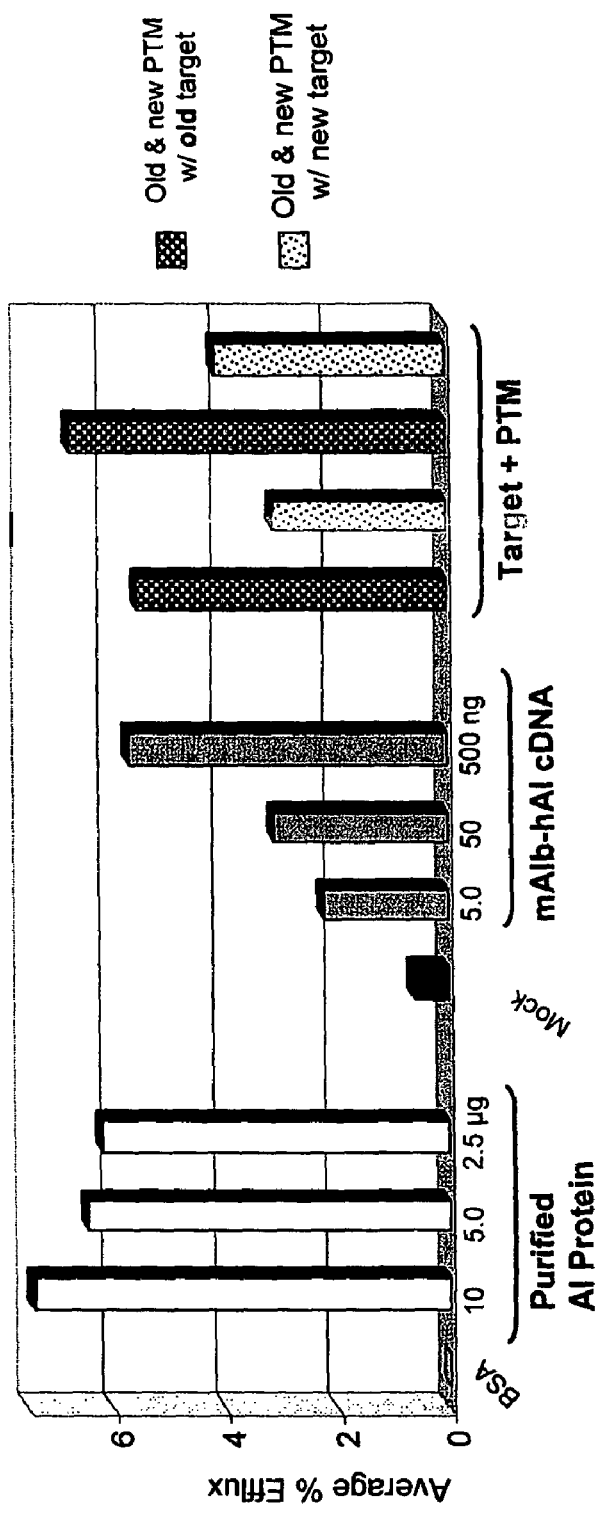

FIG. 41 Trans-splicing between target and PTM plasmids produces functional protein in 293 cells. 293 cells transfected with different concentrations of mAlb-hapoAI cDNA or PTM+target plasmids. 48 hrs post-transfection, media was collected, processed and assayed (efflux potential) for activity as described before.

Figure 42:
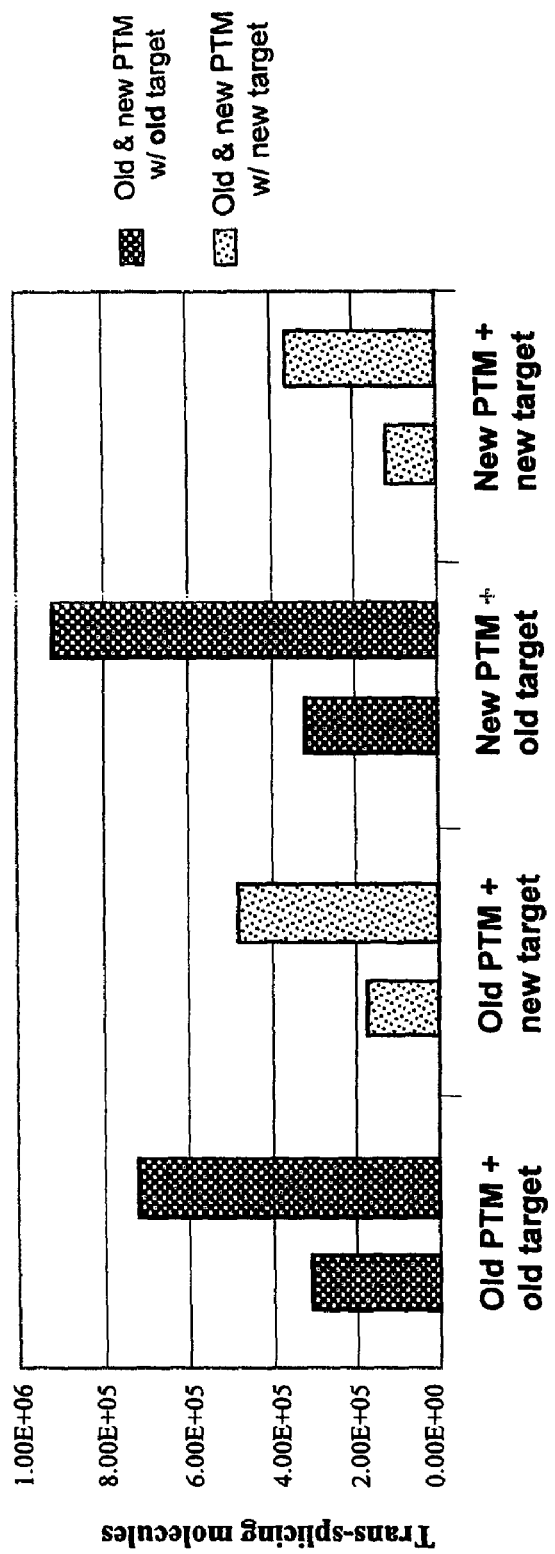

FIG. 42 Trans-splicing efficiency of the new and old PTMs in 293 cells. 293 cells transfected with different concentrations of PTM+target plasmids. 48 hrs post-transfection, total RNA isolated and trans-splicing efficiency was quantified by qRT-PCR using specific primers.

FIG. 43A RT-PCR results showing the presence of mouse mAlb-hapoAI mRNA

FIG. 43B RT-PCR results showing the presence of trans-spliced mRNA in mice.

FIG. 43C. RT-PCR results showing trans-splicing of human apoAI PTM into endogenous mouse albumin pre-mRNA in mice. MC, minicircles, PL, plasmid DNA; RT, reverse transcription and +/− indicate RT+ and RT− reactions.

Figure 44A:
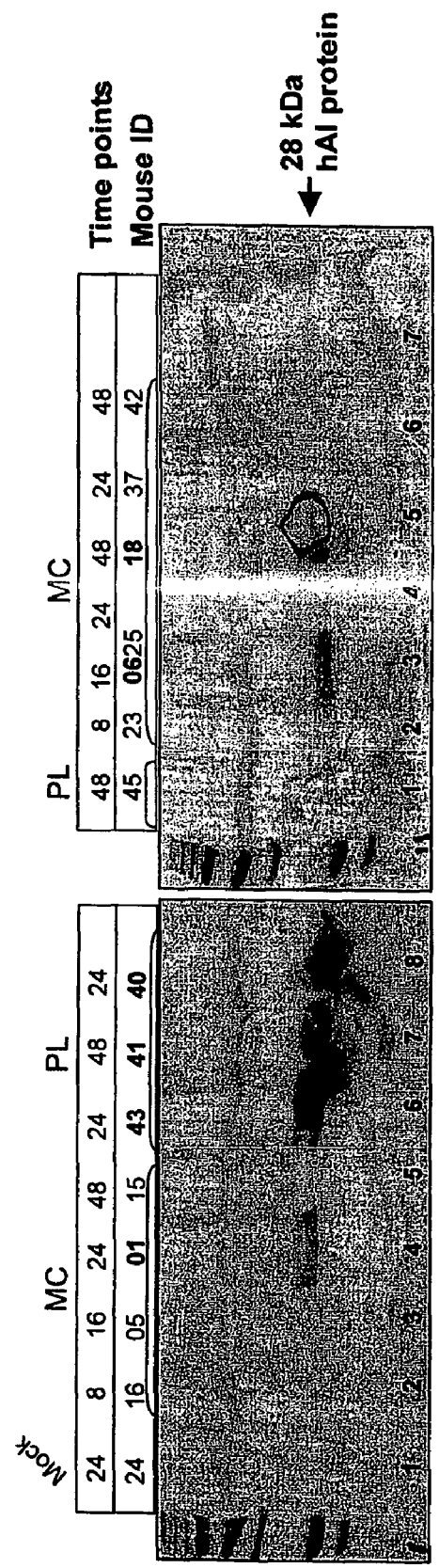

FIG. 44A. Western blot analysis of serum samples from mice injected with mAlb-hapoAI cDNA. 20 μl serum passed through Proto-Blue column (to deplete albumin+IgG) and analyzed by Western blot using human apoAI specific antibody. MC, minicircles and PL, plasmid DNA RT.

Figure 44B:
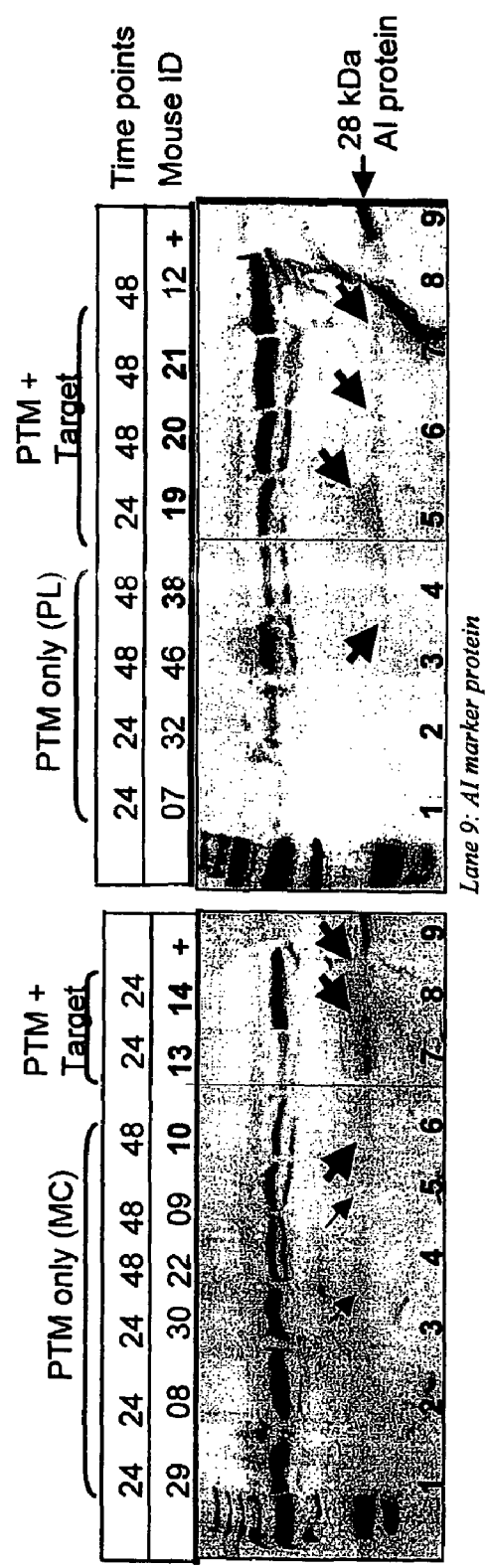

FIG. 44B. Western blot analysis of serum samples from mice injected with PTM only and PTM+Target plasmids. 20-50 μl serum passed through Proto-Blue column (to deplete albumin+IgG) and analyzed by Western blot using human apoAI specific antibody. MC, minicircles and PL, plasmid DNA.

FIG. 45A. Western blot analysis of serum samples from mice injected with PTM plasmid. 50 μl serum was immunoprcipitated and analyzed by Western blot using human apoAI specific antibody. Arrows indicate 28 kDa human apoAI protein.

FIG. 45B. Western blot analysis of serum samples from mice injected with cDNA plasmid. 10 μl serum was immunoprcipitated and analyzed by Western blot using human apoAI specific antibody.

FIG. 46. HDL analysis of serum samples from mice injected with PTM and mAlb-hapoAI cDNA plasmids.

FIG. 47. Schematic illustration of trans-splicing strategy to increase biological half-life of human apoAI protein. hAI, human apoAI and Ex, exon.

FIG. 48. Schematic illustration of trans-splicing (pro) strategy to improve function. Pro, sequence encoding for pro peptide.

FIG. 49. Schematic illustration of trans-splicing (pre-pro) strategy to improve function. Pre, sequence coding for pre signal peptide; Pro, sequence coding for pro signal peptide.

5. DETAILED DESCRIPTION OF THE INVENTION

The present invention relates to novel compositions comprising pre-trans-splicing molecules (PTMs) and the use of such molecules for generating novel nucleic acid molecules. The PTMs of the invention comprise (i) one or more target binding domains that are designed to specifically bind to a apoAI or apoB target pre-mRNA or other expressed pre-mRNA targets, such as albumin pre-mRNA, (ii) a 3' splice region that includes a branch point, pyrimidine tract and a 3' splice acceptor site and/or a 5' splice donor site; and (iii) additional nucleotide sequences such as those encoding for the the wild type apoAI, apoAI analogues or apoAI variants, especially the Milano variant. The PTMs of the invention may further comprise one or more spacer regions that separate the RNA splice site from the target binding domain.

The methods of the invention encompass contacting the PTMs of the invention with apoAI target pre-mRNA, or apoB target pre-mRNA, or other expressed pre-mRNA targets such as albumin target pre-mRNA, under conditions in which a portion of the PTM is trans-spliced to a portion of the target pre-mRNA to form a novel chimeric RNA that results in expression of the apoAI Milano variant or other apoAI variants, wild type apoAI, or an apoB/apoAI Milano chimeric protein, or other chimeric protein encompassing other variants of apoAI.

5.1. Structure of the Pre-Trans-Splicing Molecules

The present invention provides compositions for use in generating novel chimeric nucleic acid molecules through targeted trans-splicing. The PTMs of the invention comprise (i) one or more target binding domains that target binding of the PTM to an apoAI or apoB pre-mRNA or other expressed pre-mRNA targets such as, for example, albumin pre-mRNA (ii) a 3' splice region that includes a branch point, pyrimidine tract and a 3' splice acceptor site and/or 5' splice donor site; and (iii) coding sequences for apoAI Milano, other variants of apoAI or wild type apoAI. The PTMs of the invention may also include at least one of the following features:(a) binding domains targeted to intron sequences in close proximity to the 3' or 5' splice signals of the target intron, (b) mini introns, (c) ISAR (intronic splicing activator and repressor)—like cis-acting elements, and/or (d) ribozyme sequences. The PTMs of the invention may further comprise one or more spacer regions to separate the RNA splice site from the target binding domain.

The general design, construction and genetic engineering of such PTMs and demonstration of their ability to mediate successful trans-splicing reactions within the cell are described in detail in U.S. Pat. Nos. 6,083,702, 6,013,487 and 6,280,978 as well as patent application Ser. Nos. 09/941,492, 09/756,095, 09/756,096 and 09/756,097, the disclosures of which are incorporated by reference in their entirety herein.

The target binding domain of the PTM endows the PTM with a binding affinity for the target pre-mRNA, i.e., an apoAI or apoB target pre-mRNA, or other pre-mRNA targets such as, for example, albumin pre-mRNA. As used herein, a target binding domain is defined as any molecule, i.e., nucleotide, protein, chemical compound, etc., that confers specificity of binding and anchors the pre-mRNA closely in space to the PTM so that the spliceosome processing machinery of the nucleus can trans-splice a portion of the PTM to a portion of the pre-mRNA. The target pre-mRNA may be mammalian, such as but not limited to, mouse, rat, bovine, goat, or human pre-RNA.

The target binding domain of the PTM may contain multiple binding domains which are complementary to and in anti-sense orientation to the targeted region of the selected pre-mRNA, i.e., an apoAI, apoB or albumin target pre-mRNA. The target binding domains may comprise up to several thousand nucleotides. In preferred embodiments of the invention the binding domains may comprise at least 10 to 30 and up to several hundred or more nucleotides. The efficiency and/or specificity of the PTM may be increased significantly by increasing the length of the target binding domain. For example, the target binding domain may comprise several hundred nucleotides or more. In addition, although the target binding domain may be "linear" it is understood that the RNA will very likely fold to form a secondary "safety" structure that may sequester the PTM splice site(s) until the PTM encounters it's pre-mRNA target, thereby increasing the specificity of trans-splicing. A second target binding region may be placed at the 3' end of the molecule and can be incorporated into the PTM of the invention. Absolute complementarily, although preferred, is not required. A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (see, for example, Sambrook et al., 1989, *Molecular Cloning, A Laboratory Manual*, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

Binding may also be achieved through other mechanisms, for example, through triple helix formation, aptamer interactions, antibody interactions or protein/nucleic acid interactions such as those in which the PTM is engineered to recognize a specific RNA binding protein, i.e., a protein bound to a specific target pre-mRNA. Alternatively, the PTMs of the invention may be designed to recognize secondary structures, such as for example, hairpin structures resulting from intramolecular base pairing between nucleotides within an RNA molecule.

In a specific embodiment of the invention, the target binding domain is complementary and in anti-sense orientation to sequences of the apoAI, apoB, or albumin target pre-mRNA, which hold the PTM in close proximity to the target for trans-splicing. For example, a target binding domain may be defined as any molecule, i.e., nucleotide, protein, chemical compound, etc., that confers specificity of binding and anchors the apoAI, or apoB or albumin pre-mRNA closely in space to the PTM so that the spliceosome processing machinery of the nucleus can trans-splice a portion of the PTM to a portion of the apoAI, or apoB, or albumin pre-mRNA.

The PTM molecule also contains a 3' splice region that includes a branchpoint sequence and a 3' splice acceptor AG site and/or a 5' splice donor site. The 3' splice region may further comprise a polypyrimidine tract. Consensus sequences for the 5' splice donor site and the 3' splice region used in RNA splicing are well known in the art (see, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (SEQ ID NO. 1) (where A=adenosine, U=uracil, G=guanine, C=cytosine, R=purine and /=the splice site). The 3' splice site consists of three separate sequence elements: the branchpoint or branch site, a polypyrimidine tract and the 3' consensus sequence (YAG). The branch point consensus sequence in mammals is YNYURAC (SEQ ID NO. 2) (Y=pyrimidine; N=any nucleotide). The underlined A is the site of branch formation. A polypyrimidine tract is located between the branch point and the splice site acceptor and is important for efficient branch point utilization and 3' splice site recognition. Recently, pre-mRNA introns beginning with the dinucleotide AU and ending with the dinucleotide AC have been identified and referred to as U12 introns. U12 intron sequences as well as any sequences that function as splice acceptor/donor sequences may also be used to generate the PTMs of the invention.

A spacer region to separate the RNA splice site from the target binding domain may also be included in the PTM. The spacer region may be designed to include features such as (i) stop codons which would function to block translation of any unspliced PTM and/or (ii) sequences that enhance trans-splicing to the target pre-mRNA.

In a preferred embodiment of the invention, a "safety, stem-loop structure" is also incorporated into the spacer, binding domain, or elsewhere in the PTM to prevent non-specific trans-splicing (Puttaraju et al., 1999 *Nat. Biotech*, 17:246-252; Mansfield S G et al., 2000, *Gene therapy*, 7:1885-1895). This is a region of the PTM that covers elements of the 3' and/or 5' splice site of the PTM by relatively weak complementarity, preventing non-specific trans-splicing. The PTM is designed in such a way that upon hybridization of the binding/targeting portion(s) of the PTM, the 3' and/or 5' splice site is uncovered and becomes fully active.

Such "safety" sequences comprise one or more complementary stretches of cis-sequence (or could be a second, separate, strand of nucleic acid) which binds to one or both sides of the PTM branch point, pyrimidine tract, 3' splice site and/or 5' splice site (splicing elements), or could bind to parts of the splicing elements themselves. This "safety" binding prevents the splicing elements from being active (i.e. block U2 snRNP or other splicing factors from attaching to the PTM splice site recognition elements). The binding of the "safety" may be disrupted by the binding of the target binding region of the PTM to the target pre-mRNA, thus exposing and activating the PTM splicing elements (making them available to trans-splice into the target pre-mRNA).

Nucleotide sequences encoding for exon 4, exons 3-4, exons 2-4, or exons 1-4 of the apoAI Milano variant are also included in the PTM of the invention. For example, the nucleotide sequence can include those sequences encoding gene products missing or altered in known genetic diseases. In addition, nucleotide sequences encoding marker proteins or peptides which may be used to identify or image cells may be included in the PTMs of the invention. In yet another embodiment of the invention nucleotide sequences encoding affinity tags such as, HIS tags (6 consecutive histidine residues) (Janknecht, et al., 1991, *Proc. Natl. Acad. Sci. USA* 88:8972-8976), the C-terminus of glutathione-S-transferase (GST) (Smith and Johnson, 1986, *Proc. Natl. Acad. Sci. USA* 83:8703-8707) (Pharmacia), FLAG (Asp-Tyr-Lys-Asp-Asp-Asp-Lys) (Eastman Kodak/IBI, Rochester, N.Y.), or CDC2 PSTAIRE epitope tag can be included in PTM molecules for use in affinity purification.

In a preferred embodiment of the invention, the PTMs of the invention contain apoAI exon 4 with an Arg to Cys substitution at position 173 (hereinafter referred to as "Arg→Cys"), thereby leading to the expression of the apoAI Milano variant protein. A variety of different PTM molecules may be synthesized to substitute (Arg→Cys) at position 173. The PTMs of the invention may contain apoAI exon or exons, which when trans-spliced to the apoAI, or apoB, target pre-mRNA or other pre-mRNA targets, will result in the formation of a composite or chimeric RNA capable of encoding an apoAI Milano variant chimeric protein, or an apoB/apoAI Milano variant protein. The nucleotide sequence of the apoAI gene is known, as well as the mutation leading to expression of the Milano variant and incorporated herein in its entirety (FIG. 3A-B). Likewise, the nucleotide sequence of the apoB gene is known (FIG. 6).

The apoAI exon sequences to be included in the structure of the PTM are designed to include apoAI exon 4 sequences as depicted in FIG. 4. In such an instance, 3' exon replacement results in the formation of a chimeric RNA molecule that encodes the apoAI Milano variant protein having a Arg→Cys substitution at position 173.

The PTM's of the invention may be engineered to contain a single apoAI exon sequence, multiple apoAI exon sequences, or alternatively the complete set of 4 exon sequences. The number and identity of the apoAI sequences to be used in the PTMs will depend on the type of trans-splicing reaction, i.e., 5' exon replacement, 3' exon replacement or internal exon replacement, as well as the pre-mRNA targets.

Specific PTMs of the invention include, but are not limited to, those containing nucleic acids encoding apoAI exon 4 sequences. Such PTMs may be used for mediating a 3' exon replacement trans-splicing reaction as depicted in FIGS. 5, 9 and 21.

Specific PTMs of the invention include, but are not limited to, those containing nucleic acid sequences encoding apoAI-Milano. Such PTMs may be used for mediating a 5' exon replacement trans-splicing reaction. These PTMs would contain the N-terminal portion of the coding sequence, including the Milano mutation. In addition, PTMs of the invention may comprise a single apoAI variant exon or any combination of two or more apoAI variant exons.

Further, the PTMs of the invention include, but are not limited to, those containing nucleic acid sequences encoding wild type apoAI and/or apoAI analogues with extended half-life and efficacy.

The present invention further provides PTM molecules wherein the coding region of the PTM is engineered to contain mini-introns. The insertion of mini-introns into the coding sequence of the PTM is designed to increase definition of the exon and enhance recognition of the PTM splice sites. Mini-intron sequences to be inserted into the coding regions of the PTM include small naturally occurring introns or, alternatively, any intron sequences, including synthetic mini-introns, which include 5' consensus donor sites and 3' consensus sequences which include a branch point, a 3' splice site and in some instances a pyrimidine tract.

The mini-intron sequences are preferably between about 60-150 nucleotides in length, however, mini-intron sequences of increased lengths may also be used. In a preferred embodiment of the invention, the mini-intron comprises the 5' and 3' end of an endogenous intron. In preferred embodiments of the invention the 5' intron fragment is about 20 nucleotides in length and the 3' end is about 40 nucleotides in length.

In a specific embodiment of the invention, an intron of 528 nucleotides comprising the following sequences may be utilized. Sequences of the intron construct are as follows:

(SEQ ID NO. 3)
5' fragment sequence:
Gtagttcttttgttcttcactattaagaacttaatttggtgtccatgtct ctttttttttctagtttgtagtgctggaaggtattttggagaaattctt acatgagcattaggagaatgtatgggtgtagtgtcttgtataatagaaat -continued
tgttccactgataatttactctagttttttatttcctcatattattttca gtggcttttcttccacatctttatattttgcaccacattcaacactgta gcggccgc.

(SEQ ID NO. 4)
3' fragment sequence:
Ccaactatctgaatcatgtgcccttctctgtgaacctctatcataatac ttgtcacactgtattgtaattgtctcttttactttcccttgtatcttttg tgcatagcagagtacctgaaacaggaagtattttaaatattttgaatcaa atgagttaatagaatctttacaaataagaatatacacttctgcttaggat gataattggaggcaagtgaatcctgagcgtgatttgataatgacctaata atgatgggttttatttccag.

In an embodiment of the invention the Tia-1 binding sequences are inserted within 100 nucleotides from the 5' donor site (Del Gatto-Konczak et al., 2000, Mol. Cell Biol. 20:6287-6299). In a preferred embodiment of the invention the Tia-1 binding sequences are inserted within 50 nucleotides from the 5' donor site. In a more preferred embodiment of the invention the Tia-1 sequences are inserted within 20 nucleotides of the 5' donor site.

The compositions of the invention further comprise PTMs that have been engineered to include cis-acting ribozyme sequences. The inclusion of such sequences is designed to reduce PTM translation in the absence of trans-splicing or to produce a PTM with a specific length or defined end(s). The ribozyme sequences that may be inserted into the PTMs include any sequences that are capable of mediating a cis-acting (self-cleaving) RNA splicing reaction. Such ribozymes include but are not limited to hammerhead, hairpin and hepatitis delta virus ribozymes (see, Chow et al. 1994, *J Biol Chem* 269:25856-64).

In an embodiment of the invention, splicing enhancers such as, for example, sequences referred to as exonic splicing enhancers may also be included in the PTM design. Trans-acting splicing factors, namely the serine/arginine-rich (SR) proteins, have been shown to interact with such exonic splicing enhancers and modulate splicing (see, Tacke et al., 1999, *Curr. Opin. Cell Biol.* 11:358-362; Tian et al., 2001, *J. Biological Chemistry* 276:33833-33839; Fu, 1995, RNA 1:663-680). Nuclear localization signals may also be included in the PTM molecule (Dingwell and Laskey, 1986, *Ann. Rev. Cell Biol.* 2:367-390; Dingwell and Laskey, 1991, *Trends in Biochem. Sci.* 16:478-481). Such nuclear localization signals can be used to enhance the transport of synthetic PTMs into the nucleus where trans-splicing occurs.

Additional features can be added to the PTM molecule either after, or before, the nucleotide sequence encoding a translatable protein, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the PTM structure to prevent translation of unspliced PTMs. Further elements, such as a 3' hairpin structure, circularized RNA, nucleotide base modification, or synthetic analogs, can be incorporated into PTMs to promote or facilitate nuclear localization and spliceosomal incorporation, and intra-cellular stability.

PTMs may also be generated that require a double-trans-splicing reaction for generation of a chimeric trans-spliced product. Such PTMs could, for example, be used to replace an internal exon or exons which could be used for expression of an apoAI variant protein. PTMs designed to promote two trans-splicing reactions are engineered as described above, however, they contain both 5' donor sites and 3' splice acceptor sites. In addition, the PTMs may comprise two or more binding domains and splice regions. The splice regions may be placed between the multiple binding domains and splice sites or alternatively between the multiple binding domains.

Optimal PTMs for wild type apoAI or other pre-mRNA targets, such as albumin pre-mRNA, may be selected by spliceosome-mediated trans-splicing high capacity screen (HCS). Such screens include, but are not limited to, those described in patent application Ser. No. 10/693,192. Briefly, each new PTM library is clonally delivered to target cells by transfection of bacterial protoplasts or viral vectors encoding the PTMs. The 5' GFP-apoAI, apoB, or albumin targets are transfected using Lipofectamine reagents and the cells analyzed for GFP expression by FACS. Total RNA samples may also be prepared and analyzed for trans-splicing by quantitative real time PCR (qRT-PCR) using target and PTM specific primers for the presence of correctly spliced repaired products and the level of repaired product. Each trans-splicing domain (TSD) and binding domain is engineered with several unique restriction sites, so that when a suitable sequence is identified (based on the level of GFP function and qRT-PCR data), part of or the complete TSD, can be readily subcloned into a PTM cassette to produce PTMs of the invention.

When specific PTMs are to be synthesized in vitro (synthetic PTMs), such PTMs can be modified at the base moiety, sugar moiety, or phosphate backbone, for example, to improve stability of the molecule, hybridization to the target mRNA, transport into the cell, etc. For example, modification of a PTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule such as a peptides (e.g., for targeting host cell receptors in vivo), or an agent facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci.* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, *BioTechniques* 6:958-976) or intercalating agents (see, e.g., Zon, 1988, *Pharm. Res.* 5:539-549). To this end, the nucleic acid molecules may be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life. Possible modifications according to the present invention include, but are not limited to, the addition of flanking sequences of ribonucleotides to the 5' and/or 3' ends of the molecule. (See FIG. 47). In some circumstances where increased stability is desired, nucleic acids having modified internucleoside linkages such as 2'-O-methylation may be preferred. Nucleic acids containing modified internucleoside linkages may be synthesized using reagents and methods that are well known in the art (see, Uhlmann et al., 1990, *Chem. Rev.* 90:543-584; Schneider et al., 1990, *Tetrahedron Lett.* 31:335 and references cited therein).

The synthetic PTMs of the present invention are preferably modified in such a way as to increase their stability in the cells. Since RNA molecules are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease cleavage. In addition, the synthetic PTMs can be produced as nuclease resistant circular molecules with enhanced stability to prevent degradation by nucleases (Puttaraju et al., 1995, *Nucleic Acids Symposium Series No.* 33:49-51; Puttaraju et al., 1993, *Nucleic Acid Research* 21:4253-4258). Other modifications may also be required, for example to enhance binding, to enhance cellular uptake, to improve pharmacology or pharmacokinetics or to improve other pharmaceutically desirable characteristics.

Modifications, which may be made to the structure of the synthetic PTMs include but are not limited to backbone modifications such as use of:

(i) phosphorothioates (X or Y or W or Z=S or any combination of two or more with the remainder as O). e.g. Y=S (Stein, C. A., et al., 1988, *Nucleic Acids Res.*, 16:3209-3221), X=S (Cosstick, R., et al., 1989, *Tetrahedron Letters*, 30:4693-4696), Y and Z=S (Brill, W. K.-D., et al., 1989, *J. Amer. Chem. Soc.*, 111:2321-2322); (ii) methylphosphonates (e.g. Z=methyl (Miller, P. S., et al., 1980, *J. Biol. Chem.*, 255:9659-9665); (iii) phosphoramidates (Z=N-(alkyl)$_2$ e.g. alkyl methyl, ethyl, butyl) (Z=morpholine or piperazine) (Agrawal, S., et al., 1988, *Proc. Natl. Acad. Sci. USA* 85:7079-7083) (X or W=NH) (Mag, M., et al., 1988, *Nucleic Acids Res.*, 16:3525-3543); (iv) phosphotriesters (Z=O-alkyl e.g. methyl, ethyl, etc.) (Miller, P. S., et al., 1982, *Biochemistry*, 21:5468-5474); and (v) phosphorus-free linkages (e.g. carbamate, acetamidate, acetate) (Gait, M. J., et al., 1974, *J. Chem. Soc. Perkin I*, 1684-1686; Gait, M. J., et al., 1979, *J. Chem. Soc. Perkin I*, 1389-1394).

In addition, sugar modifications may be incorporated into the PTMs of the invention. Such modifications include the use of: (i) 2'-ribonucleosides (R=H); (ii) 2'-O-methylated nucleosides (R=OMe) ) (Sproat, B. S., et al., 1989, *Nucleic Acids Res.*, 17:3373-3386); and (iii) 2'-fluoro-2'-riboxynucleosides (R=F) (Krug, A., et al., 1989, *Nucleosides and Nucleotides*, 8:1473-1483).

Further, base modifications that may be made to the PTMs, including but not limited to use of: (i) pyrimidine derivatives substituted in the 5-position (e.g. methyl, bromo, fluoro etc) or replacing a carbonyl group by an amino group (Piccirilli, J. A., et al., 1990, *Nature*, 343:33-37); (ii) purine derivatives lacking specific nitrogen atoms (e.g. 7-deaza adenine, hypoxanthine) or functionalized in the 8-position (e.g. 8-azido adenine, 8-bromo adenine) (for a review see Jones, A. S., 1979, *Int. J. Biolog. Macromolecules*, 1: 194-207).

In addition, the PTMs may be covalently linked to reactive functional groups, such as: (i) psoralens (Miller, P. S., et al., 1988, *Nucleic Acids Res.*, Special Pub. No. 20, 113-114), phenanthrolines (Sun, J-S., et al., 1988, *Biochemistry*, 27:6039-6045), mustards (Vlassov, V. V., et al., 1988, *Gene*, 72:313-322) (irreversible cross-linking agents with or without the need for co-reagents); (ii) acridine (intercalating agents) (Helene, C., et al., 1985, *Biochimie*, 67:777-783); (iii) thiol derivatives (reversible disulphide formation with proteins) (Connolly, B. A., and Newman, P. C., 1989, *Nucleic Acids Res.*, 17:4957-4974); (iv) aldehydes (Schiff's base formation); (v) azido, bromo groups (UV cross-linking); or (vi) ellipticines (photolytic cross-linking) (Perrouault, L., et al., 1990, *Nature*, 344:358-360).

In an embodiment of the invention, oligonucleotide mimetics in which the sugar and internucleoside linkage, i.e., the backbone of the nucleotide units, are replaced with novel groups can be used. For example, one such oligonucleotide mimetic which has been shown to bind with a higher affinity to DNA and RNA than natural oligonucleotides is referred to as a peptide nucleic acid (PNA) (for review see, Uhlmann, E. 1998, *Biol. Chem.* 379:1045-52). Thus, PNA may be incorporated into synthetic PTMs to increase their stability and/or binding affinity for the target pre-mRNA.

In another embodiment of the invention synthetic PTMs may covalently linked to lipophilic groups or other reagents capable of improving uptake by cells. For example, the PTM molecules may be covalently linked to: (i) cholesterol (Letsinger, R. L., et al., 1989, *Proc. Natl. Acad. Sci. USA* 86:6553-6556); (ii) polyamines (Lemaitre, M., et al., 1987, *Proc. Natl. Acad. Sci. USA* 84:648-652); other soluble polymers (e.g. polyethylene glycol) to improve the efficiently with which the PTMs are delivered to a cell. In addition, combinations of the above identified modifications may be utilized to increase the stability and delivery of PTMs into the target cell. The PTMs of the invention can be used in methods designed to produce a novel chimeric RNA in a target cell.

The methods of the present invention comprise delivering to the target cell a PTM which may be in any form used by one skilled in the art, for example, an RNA molecule, or a DNA vector which is transcribed into a RNA molecule, wherein said PTM binds to a pre-mRNA and mediates a trans-splicing reaction resulting in formation of a chimeric RNA comprising a portion of the PTM molecule spliced to a portion of the pre-mRNA. Furthermore, the invention also encompasses additional methods for modifying or converting mRNAs such as use of trans-splicing ribozymes and other means that are known to skilled practitioners in the field.

In a specific embodiment of the invention, the PTMs of the invention can be used in methods designed to produce a novel chimeric RNA in a target cell so as to result in expression of the apoAI Milano or other variant proteins. The methods of the present invention comprise delivering to a cell a PTM which may be in any form used by one skilled in the art, for example, an RNA molecule, or a DNA vector which is transcribed into a RNA molecule, wherein said PTM binds to a apoAI or apoB pre-mRNA and mediates a trans-splicing reaction resulting in formation of a chimeric RNA comprising the portion of the PTM molecule having the apo-1 Milano mutation spliced to a portion of the pre-mRNA.

In another specific embodiment of the invention, the PTMs of the invention can be used in methods designed to produce a novel chimeric RNA in a target cell so as to result in the substitution of albumin expression with expression of the wild type apoAI, apoAI Milano or other variant proteins. The methods of the present invention comprise delivering to a cell a PTM which may be in any form used by one skilled in the art, for example, an RNA molecule, or a DNA vector which is transcribed into a RNA molecule, wherein said PTM binds to an albumin pre-mRNA and mediates a trans-splicing reaction resulting in formation of a chimeric RNA comprising the portion of the PTM molecule encoding wild type apoAI, or apoAI Milano variant spliced to a portion of the pre-mRNA.

5.2. Synthesis of the Trans-Splicing Molecules

The nucleic acid molecules of the invention can be RNA or DNA or derivatives or modified versions thereof, single-stranded or double-stranded. By nucleic acid is meant a PTM molecule or a nucleic acid molecule encoding a PTM molecule, whether composed of deoxyribonucleotides or ribonucleosides, and whether composed of phosphodiester linkages or modified linkages. The term nucleic acid also specifically includes nucleic acids composed of bases other than the five biologically occurring bases (adenine, guanine, thymine, cytosine and uracil). In addition, the PTMs of the invention may comprise, DNA/RNA, RNA/protein or DNA/RNA/protein chimeric molecules that are designed to enhance the stability of the PTMs.

The PTMs of the invention can be prepared by any method known in the art for the synthesis of nucleic acid molecules. For example, the nucleic acids may be chemically synthesized using commercially available reagents and synthesizers by methods that are well known in the art (see, e.g., Gait, 1985, *Oligonucleotide Synthesis: A Practical Approach*, IRL Press, Oxford, England).

Alternatively, synthetic PTMs can be generated by in vitro transcription of DNA sequences encoding the PTM of interest. Such DNA sequences can be incorporated into a wide variety of vectors downstream from suitable RNA polymerase promoters such as the T7, SP6, or T3 polymerase promoters. Consensus RNA polymerase promoter sequences include the following:

```
                                       (SEQ ID NO. 5)
T7:         TAATACGACTCACTATAGGGAGA (SEQ ID NO. 6)
SP6:        ATTTAGGTGACACTATAGAAGNG (SEQ ID NO. 7)
T3:         AATTAACCCTCACTAAAGGGAGA.
```

The base in bold is the first base incorporated into RNA during transcription. The underline indicates the minimum sequence required for efficient transcription.

RNAs may be produced in high yield via in vitro transcription using plasmids such as SPS65 and Bluescript (Promega Corporation, Madison, Wis.). In addition, RNA amplification methods such as Q-β amplification can be utilized to produce the PTM of interest.

The PTMs may be purified by any suitable means, as are well known in the art. For example, the PTMs can be purified by gel filtration, affinity or antibody interactions, reverse phase chromatography or gel electrophoresis. Of course, the skilled artisan will recognize that the method of purification will depend in part on the size, charge and shape of the nucleic acid to be purified.

The PTM's of the invention, whether synthesized chemically, in vitro, or in vivo, can be synthesized in the presence of modified or substituted nucleotides to increase stability, uptake or binding of the PTM to a target pre-mRNA. In addition, following synthesis of the PTM, the PTMs may be modified with peptides, chemical agents, antibodies, or nucleic acid molecules, for example, to enhance the physical properties of the PTM molecules. Such modifications are well known to those of skill in the art.

In instances where a nucleic acid molecule encoding a PTM is utilized, cloning techniques known in the art may be used for cloning of the nucleic acid molecule into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

The DNA encoding the PTM of interest may be recombinantly engineered into a variety of host vector systems that also provide for replication of the DNA in large scale and contain the necessary elements for directing the transcription of the PTM. The use of such a construct to transfect target cells in the patient will result in the transcription of sufficient amounts of PTMs that will form complementary base pairs with the endogenously expressed pre-mRNA targets, such as for example, apoAI or apoB pre-mRNA target, and thereby facilitate a trans-splicing reaction between the complexed nucleic acid molecules. For example, a vector can be introduced in vivo such that is taken up by a cell and directs the transcription of the PTM molecule. Such a vector can remain episomal or become chromosomally integrated, as long as it can be transcribed to produce the desired RNA, i.e., PTM. Such vectors can be constructed by recombinant DNA technology methods standard in the art. A vector can also be introduced into a cell ex vivo and the transfected/transduced cells returned to the patient.

Vectors encoding the PTM of interest can be plasmid, viral, or others known in the art, used for replication and expression in mammalian cells. Expression of the sequence encoding the PTM can be regulated by any promoter/enhancer sequences known in the art to act in mammalian, preferably human cells. Such promoters/enhancers can be inducible or constitutive. Such promoters include but are not limited to: the SV40 early promoter region (Benoist, C. and Chambon, P. 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad. Sci. USA* 78:1441-1445), the regulatory sequences of the metallothionein gene (Brinster et al., 1982, *Nature* 296:39-42), the viral CMV promoter, the human chorionic gonadotropin-β promoter (Hollenberg et al., 1994, *Mol. Cell. Endocrinology* 106:111-119), etc.

In a specific embodiment of the invention, liver specific promoter/enhancer sequences may be used to promote the synthesis of PTMs in liver cells for expression of the apoAI Milano variant protein. Such promoters include, for example, the albumin, transthyretin, CMV enhancers/chicken beta-actin promoter, ApoE enhancer alpha1-antitrypsin promoter and endogenous apoAI or apo-B promoter elements. In addition, the liver-specific microglobulin promoter cassette optimized for apoAI or apo-B gene expression may be used, as well as, post-transcriptional elements such as the wood chuck post-transcriptional regulatory element (WPRE).

Any type of plasmid, cosmid, YAC or viral vector can be used to prepare the recombinant DNA construct which can be introduced directly into the tissue site. Alternatively, viral vectors can be used which selectively infect the desired target cell. Vectors for use in the practice of the invention include any eukaryotic expression vectors, including but not limited to viral expression vectors such as those derived from the class of retroviruses, adenoviruses or adeno-associated viruses.

A number of selection systems can also be used, including but not limited to selection for expression of the herpes simplex virus thymidine kinase, hypoxanthine-guanine phosphoribosyltransferase and adenine phosphoribosyl transferase protein in tk-, hgprt- or aprt-deficient cells, respectively. Also, anti-metabolic resistance can be used as the basis of selection for dihydrofolate transferase (dhfr), which confers resistance to methotrexate; xanthine-guanine phosphoribosyl transferase (gpt), which confers resistance to mycophenolic acid; neomycin (neo), which confers resistance to aminoglycoside G-418; and hygromycin B phosphotransferase (hygro) which confers resistance to hygromycin. In a preferred embodiment of the invention, the cell culture is transformed at a low ratio of vector to cell such that there will be only a single vector, or a limited number of vectors, present in any one cell.

5.3. Uses and Administration of Trans-Splicing Molecules

5.3.1. Use of PTM Molecules for Expression of ApoAI Milano Variants

The compositions and methods of the present invention are designed to substitute apoAI, or apoB expression, or other pre-mRNA targets, such as albumin, with wild-type apoAI, apoAI Milano or other apoAI variant expression. Specifically, targeted trans-splicing, including double-trans-splicing reactions, 3' exon replacement and/or 5' exon replacement can be used to substitute apoAI, apoB, or albumin sequences with either wild type apoAI or apoAI Milano sequences resulting in expression of apoAI wild type or Milano variant.

Various delivery systems are known and can be used to transfer the compositions of the invention into cells, e.g. encapsulation in liposomes, microparticles, microcapsules, recombinant cells capable of expressing the composition, receptor-mediated endocytosis (see, e.g., Wu and Wu, 1987, *J. Biol. Chem.* 262:4429-4432), construction of a nucleic acid as part of a retroviral, adenoviral, adeno-associated viral or other vector, incorporation into a plasmid or mini-circle, injection of DNA, electroporation, calcium phosphate mediated transfection, etc.

The compositions and methods can be used to provide a gene encoding a wild-type apoAI, apoAI Milano, apoB/apoAI wild type or Milano, alb/apoAI wild type or milano chimeric protein to cells of an individual where expression of said gene products reduces plaque formation.

Specifically, the compositions and methods can be used to provide sequences encoding a wild type apoAI, an apoAI Milano variant molecule, or apoB/apoAI or alb/apoAI chimeric protein to cells of an individual to reduce the plaque formation normally associated with vascular disorders leading to heart attacks and stroke.

In a preferred embodiment, nucleic acids comprising a sequence encoding a PTM are administered to promote PTM function, by way of gene delivery and expression into a host cell. In this embodiment of the invention, the nucleic acid mediates an effect by promoting PTM production. Any of the methods for gene delivery into a host cell available in the art can be used according to the present invention. For general reviews of the methods of gene delivery see Strauss, M. and Barranger, J. A., 1997, Concepts in Gene Therapy, by Walter de Gruyter & Co., Berlin; Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 33:573-596; Mulligan, 1993, *Science* 260:926-932; and Morgan and Anderson, 1993, *Ann. Rev. Biochem.* 62:191-217; 1993, TIBTECH 11(5): 155-215. Exemplary methods are described below.

Delivery of the PTM into a host cell may be either direct, in which case the host is directly exposed to the PTM or PTM encoding nucleic acid molecule, or indirect, in which case, host cells are first transformed with the PTM or PTM encoding nucleic acid molecule in vitro or ex vivo, then transplanted into the host. These two approaches are known, respectively, as in vivo or ex vivo gene delivery.

In a specific embodiment, the nucleic acid is directly administered in vivo, where it is expressed to produce the PTM. This can be accomplished by any of numerous methods known in the art, e.g., by constructing it as part of an appropriate nucleic acid expression vector and administering it so that it becomes intracellular, e.g. by infection using a defective or attenuated retroviral or other viral vector (see U.S. Pat. No. 4,980,286), or by direct injection of naked DNA, or by use of microparticle bombardment (e.g., a gene gun; Biolistic, Dupont, Bio-Rad), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, *J. Biol. Chem.* 262:4429-4432).

In a specific embodiment, a viral vector that contains the PTM can be used. For example, a retroviral, including lentiviral, vector can be utilized that has been modified to delete retroviral sequences that are not necessary for packaging of the viral genome and integration into host cell DNA (see Miller et al., 1993, *Meth. Enzymol.* 217:581-599). Alternatively, adenoviral or adeno-associated viral vectors can be used for gene delivery to cells or tissues. (see, Kozarsky and Wilson, 1993, *Current Opinion in Genetics and Development* 3:499-503 for a review of adenovirus-based gene delivery).

In a preferred embodiment of the invention an adeno-associated viral vector may be used to deliver nucleic acid molecules capable of encoding the PTM. The vector is designed so that, depending on the level of expression desired, the promoter and/or enhancer element of choice may be inserted into the vector.

Another approach to gene delivery into a cell involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. The resulting recombinant cells can be delivered to a host by various methods known in the art. In a preferred embodiment, the cell used for gene delivery is autologous to the host's cell.

In a specific embodiment of the invention, hepatic stem cells, oval cells, or hepatocytes may be removed from a subject and transfected with a nucleic acid molecule capable of encoding a PTM designed to produce, upon trans-splicing, a wild-type apoAI, an apoAI Milano or other apoAI variant protein and/or apoB/apoAI or alb/apoAI chimeric protein. Cells may be further selected, using routine methods known to those of skill in the art, for integration of the nucleic acid molecule into the genome thereby providing a stable cell line expressing the PTM of interest. Such cells are then transplanted into the subject, thereby providing a source of wild type apoAI, or apoAI Milano variant protein.

The present invention also provides for pharmaceutical compositions comprising an effective amount of a PTM or a nucleic acid encoding a PTM, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

In specific embodiments, pharmaceutical compositions are administered: to subjects with diseases or disorders involving accumulation of plaque in the vascular system, for example, in hosts where aberrant levels of apoAI and apoB protein are expressed. The activity of the protein encoded for by the chimeric mRNA resulting from the PTM mediated trans-splicing reaction can be readily detected, e.g., by obtaining a host tissue sample (e.g., from biopsy tissue, or a blood sample) and assaying in vitro for mRNA or protein levels or activity of the expressed chimeric mRNA.

In specific embodiments, pharmaceutical compositions are administered in diseases or disorders involving the accumulation of plaque in the vascular system, for example, in hosts where apoAI and/or apoB are aberrantly expressed, or expressed at low levels. Such disorders include but are not limited to vascular disorders that frequently lead to atherosclerosis, heart attacks or strokes.

Many methods standard in the art can be thus employed, including but not limited to immunoassays to detect and/or visualize the protein, i.e., wild type apoAI, apoAI Milano or apoB/apoAI Milano chimeric protein, encoded for by the chimeric mRNA (e.g., Western blot, immunoprecipitation followed by sodium dodecyl sulfate polyacrylamide gel electrophoresis, immunocytochemistry, etc.) and/or hybridization assays to detect formation of chimeric mRNA expression by detecting and/or visualizing the presence of chimeric mRNA (e.g., Northern assays, dot blots, in situ hybridization, and Reverse-Transcription PCR, etc.), etc.

In a specific embodiment, it may be desirable to administer the pharmaceutical compositions of the invention locally to the area in need of treatment, i.e., liver tissue. This may be achieved by, for example, and not by way of limitation, local infusion during surgery, topical application, e.g., in conjunction with a wound dressing after surgery, by injection, by means of a catheter or stent, by means of an endoscope, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels.

The PTM will be administered in amounts which are effective to produce the desired effect in the targeted cell. Effective dosages of the PTMs can be determined through procedures well known to those in the art which address such parameters as biological half-life, bioavailability and toxicity. The amount of the composition of the invention which will be effective will depend on the severity of the vascular disorder being treated, and can be determined by standard clinical techniques. Such techniques include analysis of blood samples to determine the level of apoAI or ApoB/apoAI or alb/apoAI chimeric protein expression. In addition, in vitro assays may optionally be employed to help identify optimal dosage ranges.

The present invention also provides a pharmaceutical pack or kit comprising one or more containers filled with one or more of the ingredients of the pharmaceutical compositions of the invention optionally associated with such container(s) can be a notice in the form prescribed by a governmental agency regulating the manufacture, use or sale of pharmaceuticals or biological products, which notice reflects approval by the agency of manufacture, use or sale for human administration.

5.3.2 Trans-Splicing Strategy to Improve Human ApoAI Function and Half-Life

Albumin is a soluble, monomeric protein that comprises about one-half of the blood serum protein and exhibits a relatively slow clearance profile compared to many plasma proteins. Because of these properties, albumin is an ideal candidate to create chimeric proteins to slow clearance profile of potential therapeutic proteins. The half-life of human serum albumin is ~20-22 days. Apolipoprotein AI (apoAI) is the major component of high density lipoprotein (HDL), and there is an inverse correlation between HDL concentration vs. number of cardiovascular incidents. See Sirtori C R et al., 1999, *Atherosclerosis* 142:29-40; Genest J 2003, *J. Inherit. Metab. Dis.* 26:267-287; Nissen et al., 2003, *JAMA* 290, 2292-2300; Brewer B H, 2004, *Am Heart J*, 148, S14-S18; Brewer B H, 2004, *N Engl J Med*, 350, 1491-1494, the disclosures of which are hereby incorporated by reference. The half-life of human apoAI protein is ~10-times lower than that of the human serum albumin. Thus, by extending the half-life of human apoAI protein by, for example, trans-splicing into albumin exon 13, more benefit would be realized per unit amount of apoAI protein. Accordingly, the methods and nucleic acid molecules of the present invention may be used to increase plasma levels of apoAI and high density lipoprotein for patients with or at risk for atherosclerosis.

In addition, as shown in FIG. 47, the targeting of other albumin introns may be used to increase half-life of human apoAI. For example, PTMs according to the present invention may contain albumin exons 14 and 15, in addition to the majority of the coding sequence for human apoAI. The resulting trans-spliced product, therefore, would contain the entire albumin coding sequence plus the human apoAI coding sequence and may be used to produce an albumin-apoAI chimeric protein with extended half-life and increased efficacy. It will be readily apparent to those skilled in the art that PTMs with other exon combinations may be constructed and used according to the claimed methods and nucleic acid molecules of the present invention. Moreover, the methods and nucleic acid molecules of the claimed invention may include the (a) human apoAI "pro" peptide and (b) "pre-pro" apoAI peptide to improve the function of the trans-spliced human apoAI protein in vivo. The strategy was designed to take advantage of the endogenous native cellular machinery to enhance recognition, processing and secretion of the final trans-spliced protein to the site of action similar to endogenous apoAI protein. This strategy is illustrated in FIGS. 48 and 49.

6. EXAMPLE

Expression of Human Apolipoprotein (ApoA-I)

6.1: Albumin-Human ApoA-I Chimeric Proteins

The present study was undertaken to evaluate the albumin targeting strategy (FIG. 21) for the production of human apoAI protein, a major component of high density lipoprotein (HDL) or other variants and subsequently increase HDL concentration as a treatment for individuals having or at risk for cardio vascular disease (CHD). The rationale for selecting albumin as a target is because of its elevated expression in liver. High albumin pre-mRNA concentration results in abundant targets for trans-splicing. The concept involves targeted trans-splicing of wild type human apoAI or apoAI analogues into albumin pre-mRNA target; and the goal is to increase apoAI expression. This study evaluates the effect of albumin sequence human apoAI protein expression, secretion and function.

The albumin-hapoAI trans-spliced product was evaluated for function in vivo. As used herein with reference to trans-spliced albumin-human apoAI described in this application indicates human apoAI plus 7 nucleotides derived from albumin (mouse or human) target pre-mRNA, and, hereafter referred to as trans-spliced chimeric mRNA or trans-spliced human apoAI protein. Human and mouse versions of the albumin-human apoAI cDNA controls (FIG. 22) to mimic the final trans-spliced mRNA were constructed and tested for expression, processing and function in 293 and hepatoma cells (HepG2). The cDNA constructs were constructed using long complementary oligonucleotides and PCR products consisting of albumin exon 1 and human apoAI exon 3 and 4. Briefly, the coding sequence of mouse and human albumin exon 1 were assembled using the following long oligos:

```
                                           (SEQ ID NO. 8)
mouse Alb forward primer:
ATGAAGTGGGTAACCTTTCTCCTCCTCCTCTTCGTCTCCGGCTCTGCTTT
TTCCAGGGGTGTGTTTCGCCGAGAAGCACCC, (SEQ ID NO. 9)
reverse primer:
GGGTGCTTCTCGGCGAAACACACCCCTGGAAAAAGCAGAGCCGGAGACGA
AGAGGAGGAGGAGAAAGGTTACCCACTTCATG,
and (SEQ ID NO. 10)
human Alb forward primer:
ATGAAGTGGGTAACCTTTATTTCCCTTCTTTTTCTCTTTAGCTCGGCTTA
TTCCAGGGGTGTGTTTCGTCGAGATGCACCC, (SEQ ID NO. 11)
reverse primer:
GGGTGCATCTCGACGAAACACACCCCTGGAATAAGCCGAGCTAAAGAGAA
AAAGAAGGGAAATAAAGGTTACCCACTTCATG.
```

The underlined nucleotides indicate the end of albumin exon 1 sequence and 2 "C"s at the 3' end of the forward primers overlap to human apoAI.

The human apoAI coding sequence was PCR amplified using a cDNA clone (ATCC: clone #MGC-1249) and primers: Apo23 (5'-CCCCAGAGCCCCTGGGATCGAGTG) (SEQ ID NO. 12) and Apo5 (5'-CTAG AAGCTT CCCACTTTGGAAACGTTTAT TCTGAGCACC GG) (SEQ ID NO. 13). The PCR product was blunted at the 5' end and then digested with Hind III (indicated in bold) restriction enzyme. The resulting product was first ligated with mouse or human albumin exon 1 and then cloned into pcDNA3.1 expression vector (Invitrogen). Expression plasmids containing the entire coding sequence of human apoAI including the signal peptide into pcDNA3.1 to generate wild type human apoAI, and the Milano variant which contains an Arg to Cys substitution at position 173 (R173C) expression plasmids were also constructed as positive controls. The final constructs were verified by sequencing.

6.2: Production, Expression and Secretion of Albumin-ApoA-I Proteins in 293 Cells The effect of albumin exon 1 sequence on expression and processing of human apoAI protein was evaluated by transfecting human and mouse cDNA plasmids along with a negative (deletion mutant) and a positive control cDNAs (wt apoAI) into 293 cells. After transfection, cells were rinsed 2× with serum free DMEM and incubated with serum free advanced DMEM media (Invitrogen). After 48 hrs post-transfection, media was collected, concentrated, analyzed for the expression of human apoAI protein.

Coomassie Blue staining of the gel revealed that both the mouse and the human cDNAs produced the predicted ~28 kDa protein band which co-migrated with that of wt apoAI demonstrating good expression, processing and secretion in 293 cells (FIG. 23. lanes 2-3, 6-7). In addition, these data also showed that the level of expression was similar to that of wt apoAI (FIG. 23. lane 4, 8) indicating no adverse effects of albumin sequence on human apoAI expression and processing. On the other hand, no such band was detected in mock transfected cells and in cells that received mouse cDNA with a 2 nucleotide deletion in the signal peptide (FIG. 23. lane 1 and 5).

The identity of the band that was observed in SDS gels as human apoAI was confirmed by Western analysis using a monoclonal human apoAI antibody (Biodesign, Cat. # H45625). About ~5-10 µg total protein from the supernatant or the total cell lysate from cells transfected with cDNA control constructs, wt apoAI and Milano variant was analyzed on a 12% SDS gel and transferred onto a nylon membrane and incubated with human anti-apoAI antibody. Western results confirmed the production of human apoAI protein with an apparent molecular mass of 28 kDa predicted for the mature protein. Western data also indicated the presence of >90% of the mature human apoAI protein from the cDNAs or wt apoAI in the supernatant compared to a cell lysate demonstrating normal processing and secretion in 293 cells (FIG. 24; compare lanes 1 & 2 with 3). Similar results were also observed with hepatoma (HepG2) cells transfected with cDNA constructs.

6.3: Trans-Spliced Albumin—Human ApoA-I Protein is Functionally Active

The effect of the 7 nucleotides from albumin on human apoAI function was evaluated by measuring ATP-binding cassette transporter protein (ABC1) mediated transfer of cellular cholesterol into apoAI acceptor. The release of radiolabeled cellular cholesterol to lipid free human apoAI was quantified and the efflux values obtained with trans-spliced proteins were compared with those from wt apoAI and negative control samples. Control HeLa and HeLa cells stably transfected with an ABC1 encoding plasmid were grown to near confluency. Cells were then loaded with 1 µCi/ml $^3$H cholesterol. After equilibrating for 24 hrs, cells were washed 3× with serum free media and incubated with a serial dilution of the media containing the trans-spliced proteins (supernatant from 293 cells transfected w/cDNA constructs, normalized for apoAI protein concentration) or with 10 µg/wild type apoAI protein as positive control. Cells were allowed to efflux for 18 hrs. After the efflux period, medium was collected and an aliquot of the medium was then counted by liquid scintillation counting. The remaining counts in the cell fraction were determined after an over night extraction with isopropanol. The percent efflux was calculated by dividing the counts in the efflux media by the sum of the counts in the media plus the cell fraction. DMEM/BSA media was used as a blank and was subtracted from the radioactive counts obtained in the presence of an acceptor in the efflux media.

The amount of ABC1 mediated efflux observed with trans-spliced proteins (mouse and human proteins) was similar to that of wt apoAI (FIG. 25). The efflux data also demonstrated that the absolute efflux activity observed with the trans-spliced proteins were comparable or slightly better than the wt apoAI protein across the concentration range tested indicating the absence of any major adverse effects due to albumin sequence in the final trans-spliced product on apoAI function. These results provide strong evidence about the effectiveness of the compositions of the present invention for the production of functional biologically active proteins in vivo.

7. EXAMPLE

High Capacity Screens for Isolation of Optimal Binding Domains for Albumin Targets A high capacity screen (HCS) to identify optimal binding domains for mouse albumin pre-mRNA target was performed as described before (U.S. patent application Ser. No. 10/693, 192, filed Oct. 24, 2003) (FIG. 26A) with various modifications (FIG. 26B).

7.1: High Capacity Screen Pre-mRNA Target

Mouse albumin intron 1 and exon 2 comprising nucleotides 114 through 877 a total of 763 by (Ref. seq. NC_000071) (FIG. 18), was PCR amplified using the genomic DNA and primers mAlb15 (5'-CTAG GGATCC GTTTTAT-GTTTTTTCATCTCTG) (SEQ ID NO. 14) and mAlb8 (5'-CTAG GCGGCCGC_AGGCCTTTGAAATGTTGT-TCTCC) (SEQ ID NO. 15). The PCR product was then digested with Bam HI and Not I (indicated in bold) and cloned into an existing HCS target plasmid to generate pc5'zsG-mIn1-Ex2 plasmid (FIG. 27). Stable cells expressing the 5' half of the coding sequence for the green fluorescent protein (GFP) (zsGreen from Clontech) coupled to intron 1 and exon 2 of mouse albumin gene was established in 293 cells by transfecting the target plasmid followed by hygromycin selection. After 2 weeks of selection, hygromycin resistant clones were pooled, characterized by RT-PCR and used for HCS.

7.2: Mouse Albumin PTM Binding Domain Library

The mouse albumin sequence comprising intron 1 and exon 2 was PCR amplified using genomic DNA and primers as described above, digested with Bam HI and Not I and ligated to generate a large concatemerized fragment (~10 kb). This step was introduced to increase BD complexity. The concatemerized DNA was then fragmented into small pieces by sonication and fractionated on a 3% agarose gel. Fragment size ranging from 50-250 nucleotides were gel purified, ends were repaired using Klenow enzyme and cloned into PTM cassette described before (U.S. patent application Ser. No. 10/693,192, filed Oct. 24, 2003) (FIG. 28).

PCR analysis of the library colonies showed >87% recombination efficiency and produced a complex library with >$10^6$ independent clones with BDs varying in size from 50-250 nts (FIG. 29). The primary library was amplified in bacteria and used for screening the optimal BDs by HCS.

7.3: PTM Selection Strategy

Following the FACS-based PTM selection strategy described before (U.S. patent application Ser. No. 10/693, 192, filed Oct. 24, 2003), a mouse albumin (mAlb) binding domain (BD) library using the assay cells expressing the 5'zsG-mIn1-Ex2 pre-mRNA target was tested. Several of the existing steps were modified and several new steps were added as outlined in FIG. 26B.

Briefly, on day 1, COS-7 cells were plated and transfected with 5'zsG-mIn1-Ex2 target plasmid using Lipo2000 reagent. On day 2, ~$10^6$ independent PTM clones were delivered to assay cells expressing 5'zsG-mIn1-Ex2 pre-mRNA as protoplasts. As illustrated in the FIG. 30, cells were sorted after 24 hr by FACS, and cells expressing high GFP and proportionate RFP were collected in 2 fractions i.e., high green (HG) and low green (LG) fractions, instead of a single fraction as previously described. PTMs from the collected cells were rescued by HIRT DNA extraction followed by EcoR V digestion to reduce target plasmid contamination in the final HIRT DNA preparation. About 40 binding domain containing PTMs from LG and HG fractions were initially tested by parallel transfection. Trans-splicing efficiency of these PTMs was assessed by FACS analysis.

As predicted, the percent GFP positive (GFP+) cells and the mean GFP fluorescence were higher in PTMs from the HG fraction compared to the LG fraction in a 2:1 ratio (FIG. 30).

A hundred more BD-containing clones from the HG fraction were isolated and tested by parallel transfection and the results are summarized in FIG. 31. GFP mean fluorescence was used as an indicator for assessing trans-splicing efficiency of the individual PTMs. Based on the GFP mean fluorescence, the trans-splicing efficiency of the majority of the PTMs selected from the HCS were either similar or slightly higher than the rationally designed model PTM (FIG. 31). However, several PTMs with considerably higher (1.5 to 2-fold) trans-splicing compared with the model PTM were present. In the current screen, a ratio of 1:20 of superior PTMs vs. the rest was obtained.

From this step, the top 20 PTMs were selected for further characterization by parallel transfection, followed by molecular analysis using reverse transcription (RT) real time quantitative PCR (RT-qPCR) for specific trans-splicing, and the results are summarized in FIG. 32. Total RNA was isolated and trans-splicing efficiency was measured by RT-qPCR. Target and PTM specific primers were used for measuring specific trans-splicing, and total splicing was measured using primers specific for the 5'zsG exon as previously described. Based on the qPCR or GFP mean fluorescence values up to ~5-10 fold enrichment (after normalization) for trans-splicing efficiency was detected with PTMs selected from the HCS compared to a rationally designed model PTM (FIG. 32). Similar results, i.e. enhancement in trans-splicing efficiency, was observed with the enriched library (LG and HG samples) compared with the starting library, which is consistent with previous screen.

The effect of BD orientation and sequence position on trans-splicing efficiency and specificity was also analyzed. The sequence of random clones from the starting PTM library were compared with the enriched library i.e., PTMs selected after one round of enrichment.

Sequence analysis of the PTMs from the starting library revealed that ~51% of the BDs were in correct (antisense) orientation compared to 49% incorrect orientation. The BD size varied from 40 nt and up to 336 nt and also showed good distribution indicating the complexity of the mAlb BD library. In contrast, sequence analysis of the PTMs selected from the enriched library, as expected, showed an increase in correct orientation BDs (88%) and the mean BD length was significantly higher than the starting library, which is consistent with previous work demonstrating that longer BDs are more efficient (Puttaraju et al., 2001). Based on molecular and GFP mean fluorescence values, lead PTMs # 88, 97, 143 and 158 were selected for functional studies. n addition to the lead PTMs mentioned above, several PTMs with significantly higher trans-splicing have been selected and compared with model PTMs, e.g., 82, 90, 93, 122, 123 and 152.

8. EXAMPLE

Trans-Splicing of Human Apolipoprotein ApoAI in Cells

8.1. Human Apolipoprotein (ApoAI) PTM

Detailed structure of a human apolipoproteinAI (apoAI) PTM used in this example to show in vitro proof of principle is shown in FIG. 33. The PTM cassette consists of a trans-splicing domain (TSD) that include unique restriction sites, NheI and SacII, for cloning the lead binding domains (BDs), a 24 nucleotide spacer region, a strong 3' splice site including the consensus yeast branch point (BP), an extended polypyrimidine tract (19 nucleotides long), a splice acceptor site (CAG dinucleotide) followed by the majority of the coding sequence for wild type human apoAI mRNA from nt 118 through nt 842 (Ref seq. NM_000039 and as shown in FIG. 3A). The PTM cassette also contains the SV40 polyadenylation site and woodchuck hepatitis post-transcriptional regulatory element (WPRE) to enhance the stability of trans-spliced message. The entire cassette is cloned into pcDNA3.1 vector backbone, which contains cytomegalovirus promoter (Invitrogen). In addition, the vector backbone was further modified to include Maz4 (transcriptional pause site) sequence to reduce cryptic cis-splicing between vector ampicillin gene and PTM 3' splice site. PTMs used for functional studies mAlbPTM97C2 and mAlbPTM158 were generated by cloning 279 bp and 149 bp BD sequence into the PTM cassette between NheI and SacII sites and were verified by sequencing.

8.2 Mouse Albumin Minigene Target Pre-mRNA

For demonstrating in vitro apoAI function, a mouse albumin mini-gene target consisting of exon 1, intron 1 and exon 2 was used. A schematic diagram of the pre-mRNA target is shown in FIG. 34. The mouse albumin coordinates are as described in Ref Seq. NC_000071. The mouse albumin Ex1-In1-Ex2 pre-mRNA target (mAlbEx1-In1-Ex2) constructed as follows: an 877 by fragment corresponding to nucleotides 1 through 877 was PCR amplified using the following mouse genomic DNA and primers: mAlb-Ex1F (5'-ctagGCTAGC ACCTTT CCTATCAACCCCACTAGC) (SEQ ID NO. 16) and mAlb8 (5'-ctagGCGGCCGC AGGCCTTTGAAATGT-TGTTCTCC) (SEQ ID NO. 17). These primers contain unique restriction sites at the end of the fragment (indicated in bold). The PCR product was digested with Nhe I and Not I and cloned into inducible expression vector pcDNA5/FRT/TO designed to use with Flip-In T-Rex system (Invitrogen). The final construct (pcDNATOfrt-mAlbEx1-In1-Ex2) contains the following features: CMV promoter, Tet operator, SV40 polyadenylation site and hygromycin selection marker for establishing stable cell lines.

8.3: Generation of a Stable Cell Line Expressing Albumin Target

Using the target plasmid described above, a stable target cell line that expressed the mouse albumin mini-gene target consist of exon 1, intron 1 and exon 2 was generated. Analysis of total RNA from cells transfected with target plasmid (pcD-NATOfrt-mAlbEx1-In1-Ex2) by RT-PCR produced the expected cis-spliced product, but no albumin protein. Upon confirming the splicing pattern of mouse albumin mini-gene target pre-mRNA, a stable cell line in Flip-In T-Rex 293 cells was established by transfecting the target plasmid followed by hygromycin selection. After selecting for a period of ~2 weeks, hygromycin resistant clones were pooled and maintained in hygromycin until used.

8.4: Efficient Trans-Splicing of Human ApoAI PTMs

Human apoAI PTMs selected from the HCS showed efficient and accurate trans-splicing to mouse albumin pre-mRNA in stable cells. PTM mediated trans-splicing and production of mouse albumin-human apoAI chimeric mRNA was evaluated by transfecting stable cells with mAlbPTM97C2 and mAlbPTM158, along with a splice mutant lacking the TSD (splice incompetent PTM) and mock transfection. Total RNA isolated from these cells was analyzed by RT-PCR using mouse albumin target and human apoAI PTM specific primers. These primers produced the predicted 390 bp product only in cells that received functional PTMs (FIG. 35, lanes 2-4 and 6). No such product was detected in cells transfected with the splice mutant or in mock transfection (FIG. 35, lane 1 and 5). The PCR product was purified and was directly sequenced, confirming the precise trans-splicing to the predicted splice sites of the PTM and the target pre-mRNA in stable cells (FIG. 35).

Real-time quantitative RT-PCR was used to quantify the fraction of mouse albumin pre-mRNA transcripts converted into chimeric mRNAs by PTMs. Primers for real-time qPCR were designed to discriminate between target exon 1 and trans-spliced mRNAs. Using the protocols described previously, trans-splicing efficiency of mAlbPTM97C2 and mAlbPTM158 was quantified.

Mouse albumin specific PTMs 97C2 and 158 showed a trans-splicing efficiency of 5.6% and 3.45%, respectively. These data confirmed robust trans-splicing between mouse albumin mini-gene target pre-mRNA and PTMs in stable cells.

8.5: Trans-Splicing and Production of Full-Length Protein

The PTM-mediated trans-splicing was assessed for the ability to produce the protein product of trans-splicing human apoAI into mouse albumin pre-mRNA in stable cells. Briefly, assay cells expressing the mouse albumin mini-gene pre-mRNA was transfected with mAlbPTMs (97C2 and 158), trans-spliced cDNA as a positive control, and splice mutant with a point mutation (G>T) at splice junction as a negative control. Cells were washed after 5 hrs with serum free media and incubated with advanced DMEM serum free medium. After 48 hrs, the medium was collected, concentrated and analyzed by Western blot. Production of full-length human apoAI protein was demonstrated using anti-human apoAI antibody as described above.

Accurate trans-splicing between mouse albumin exon 1 and the PTM would result in a 28 kDa albumin-human apoAI chimeric protein. Trans-splicing mediated production of full-length mature human apoAI protein is evident in cells transfected with functional PTMs (97C2 and 158) (FIG. 36, lanes 2-3) but not in controls, i.e., cells transfected with a splice mutant or in mock (FIG. 36, lanes 4-5) and it also co-migrated with the human apoAI protein produced using cDNA control plasmid (FIG. 36, lane 1-3). These studies again confirmed precise trans-splicing between the mouse albumin exon 1 and human apoAI PTMs, resulting in the production of full-length human apoAI protein in stable cells.

9. EXAMPLE

Trans-Splicing to Endogenous Mouse Albumin Pre-mRNA in Mice

The efficacy of the lead PTMs selected from the high capacity screen (HCS) were evaluated in vivo. Fifty micrograms of mAlbPTM97C2 (PTM only) or 20 µg of mouse albumin mini-gene target plus 30 µg of mAlbPTM97C2 plasmids were mixed with jet-PEI-Gal (Q-Biogen) reagent and injected via the tail vein into normal C57BL/6 mice. Liver and serum samples were collected at 24 and 48 hrs time points. Total and poly A mRNA was isolated and analyzed by RT-PCR using mouse albumin exon 1 specific and human apoAI PTM specific primers.

Trans-splicing was detected in a single round in mice that received both mini-gene target plus PTM plasmids, as well as in mice that received PTM only (FIG. 37, lane 3, 8 & 9). Each positive RT-PCR product was purified and sequenced demonstrating the precise trans-splicing of mouse albumin exon 1 into human apoAI coding sequence at the predicted splice sites (FIG. 37, lower panel). These results demonstrated accurate trans-splicing between the PTM and the endogenous albumin pre-mRNA target in mice and further validated albumin targeting strategy in vivo.

FIG. 38 describes a strategy to increase apoAI expression by targeting to human albumin sequences by inclusion of a signal peptide. FIG. 39 describes various means of eliminating albumin sequences in the final trans-spliced product, i.e. to produce a trans-spliced product that is identical to the wild type human apoAI without any albumin sequence.

10. EXAMPLE

In Vitro Trans-Splicing of Human ApoAI into Mouse Albumin Pre-mRNA: Functionality of the Product The function of the human apoAI protein produced through trans-splicing of human apoAI into mouse albumin pre-mRNA has been evaluated in vitro. This was assessed by measuring, ATP-binding cassette transporter protein (ABC1) mediated, transfer of cellular cholesterol into apoAI acceptor. The release of radio-labeled cellular cholesterol to lipid free human apoAI was quantified and the efflux values obtained with trans-spliced protein were compared with that from wild type human apoAI protein. Human embryonic kidney cells (HEK293) were transfected with mouse albumin PTM (mAlbPTM97C2) containing either: the apoAI natural 3'UTR+bovine growth hormone poly A signal (BGH pA); or WPRE 3'UTR+SV40 poly A signal (SV40 pA) along with mouse albumin mini-gene targets (FIG. 40). 48 hrs post-transfection, supernatant was collected, concentrated and assayed for cholesterol efflux. HeLa cells transfected with ABC1 plasmid and HeLa control cells were grown to near confluency. Cells were then loaded with 1 µCi/ml $^3$H cholesterol. After equilibrating for 24 hrs, the cells were washed and incubated with media containing the trans-spliced human apoAI protein (supernatant from HEK293 cells transfected with PTM+target or cDNA control plasmid that mimics trans-splicing) or with different concentrations (2.5 µg, 5 µg, or 10 µg) of wild type purified apoAI protein as positive control. Cells were then allowed to efflux for 18 hrs. After the efflux period, medium was collected and an aliquot was then counted by liquid scintillation counting. The remaining counts in the cell fraction were determined after an over night extraction with isopropanol. The percent efflux was calculated by dividing the counts in the efflux media by the sum of the counts in the medium plus the cell fraction. DMEM/BSA medium was used as a blank and was subtracted from the radioactive counts obtained in the presence of an acceptor in the efflux media. As shown in FIG. 41, the amount of ABC1-mediated efflux observed with trans-spliced protein was significantly above the background and was similar to that of wt apoAI produced from control cDNA plasmid. The above described results indicate (a) that human apoAI protein produced through trans-splicing is functional and (b) the absence of adverse effects due to albumin sequence in the final trans-spliced mRNA on apoAI function.

Trans-splicing efficiency at the RNA level was quantified by real time RT-PCR (qRT-PCR) and the results are shown in FIG. 42. Based on qRT-PCR results it is clear that both PTMs, i.e., PTM with apoAI natural 3'UTR plus bovine growth hormone (BGH) poly A signal (new PTM) and the PTM with WPRE 3'UTR plus SV40 pA signal (old PTM), showed similar trans-splicing efficiency at the RNA level. The accuracy of trans-splicing was confirmed by direct sequencing of the RT-PCR product.

11 EXAMPLE

In Vivo Trans-Splicing of Human ApoAI into Mouse Albumin Pre-mRNA

Trans-splicing to an endogenous mouse albumin pre-mRNA target has been shown to produce human apoAI protein and HDL in mice. In particular, to verify the efficacy of the lead PTMs selected from high capacity screen (HCS) and to demonstrate trans-splicing of PTM into endogenous mouse albumin target followed by production of human apoAI protein, the following experiment has been performed. Fifty micrograms of: mAlbPTM97C2 (PTM only); 30 μg of PTM+ 15 μg of mini-gene target (additional target plasmid to increase pre-mRNA concentration); or 20 μg of control cDNA plasmid that mimic trans-spliced mRNA were hydrodynamically injected via the tail vein into normal C57BL/6 mice. Liver and serum samples were collected at 8, 16, 24 and 48 hrs time points. Total and polyA mRNA was isolated and analyzed by end point RT-PCR using mouse albumin exon 1 specific (ACCTTTCTCCTCCTCCTCTTCGT) (SEQ ID NO. 18) and human apoAI PTM specific primers (ACATAGTCTCTGCCGCTGTCTTT) (SEQ ID NO. 19). As shown in FIG. 43A the presence of trans-spliced chimeric mRNA was detected in 11 out of 14 mice that were injected with cDNA control plasmid, indicating good delivery of the plasmid DNA. Next, PTM trans-splicing to endogenous mouse albumin pre-mRNA target was evaluated using the target and PTM specific primers as described above. Trans-splicing between mouse albumin target pre-mRNA and PTM was readily detected in a single round of PCR with 1 μg of total RNA and 25 cycles of amplification. All samples from mice that received both the mini-gene target and the PTM plasmids were positive for trans-splicing (FIG. 43B). In comparison, 10 out of 13 mice were positive for trans-splicing that received the PTM only (FIG. 43C). Each positive RT-PCR product was purified and sequenced demonstrating precise trans-splicing of human apoAI coding sequence into mouse albumin exon 1 at the predicted splice sites. These results demonstrate accurate trans-splicing between the PTM and the endogenous albumin pre-mRNA target in mice and further validate albumin targeting strategy for the production of therapeutic proteins in vivo.

In addition, accurate trans-splicing to the endogenous mouse albumin pre-mRNA target to produce human apoAI protein in mice was demonstrated. Serum samples were collected from mice injected with PTM only, PTM+target and cDNA for the production of human apoAI protein were tested by Western blot. Approximately, 20-50 μl serum was passed through ProteoPrep™Blue affinity column (Sigma-Aldrich, Product Code PROT BA). This step was introduced to eliminate albumin and IgGs which make up greater than 70% of the proteins in serum and to increase sample loads to better visualize lower abundant proteins. Samples separated by 12% SDS-PAGE were transferred to nitrocellulose membranes and probed with a human specific apoAI monoclonal antibody (Biodesign International, Cat # H45625M). Proteins were visualized by a chemiluminescence kit (Invitrogen, Cat# WB7103). Western blot results indicated the appearance of human apoAI protein as early as 16 hrs post-injection in mice injected with cDNA control plasmids. In this group, 7 out of 14 samples were positive for human apoAI protein. (FIG. 44A). In mice that received both target and PTM, 5 out of 6 samples were positive for human apoAI protein. In mice that received the PTM only (targeting endogenous target), 4 out of 10 samples were positive for human apoAI protein. These results demonstrate the accurate trans-splicing of human apoAI sequence into endogenous mouse albumin exon 1 leading to the production of human apoAI protein (FIG. 44B).

12 EXAMPLE

In Vivo Trans-Splicing of Minicircle Vector DNA for Expression of Human ApoAI Protein Minicircles are DNA vectors that lack the bacterial DNA sequence that is implicated in the silencing of gene expression in vivo. See, for example, Chen Z Y, He C Y, Ehrhardt A, Kay M A. (2003) DNA vectors devoid of bacterial DNA result in persistent and high-level transgene expression in vivo. *Mol Ther.* 8:495-500; Chen Z Y, He C Y, Meuse L, Kay M A. (2004) Silencing of episomal transgene expression by plasmid bacterial DNA elements in vivo. *Gene Ther.* 11:856-864 the disclosures of which are hereby incorporated by reference.

Minicircles were tested by cloning the mAlbPTM97C2 expression cassette into minicircle vector. Fifty to seventy five micrograms of mAlbPTM97C2 (functional PTM), mAlbPTM97C2-splice mutant (defective PTM) or control cDNA (mimics trans-spliced mRNA) in the form of minicircles were hydrodynamically injected via tail vein into normal C57BL/6 mice. Liver and serum samples were collected at 48 hrs through 4 week time points. RNA analysis by qRT-PCR using mouse albumin exon 1 specific forward primer and human apoAI specific reverse primer confirmed the trans-splicing of mouse albumin PTM into endogenous mouse albumin pre-mRNA target. As shown in Table 1, the results obtained with a splice mutant PTM were similar to background observed in the mock group. The presence of trans-spliced mRNA was readily detected at 4 week post-injection indicating minicicrles can be used as a non-viral PTM delivery system.

TABLE 1

Trans-splicing in mice - qRT-PCR Results

| Group | Mouse ID | Weight | Injection remarks | time | nor-TS |
|---|---|---|---|---|---|
| A. Mock | 4 | 21.9 | ok | 48 h | 1.18E+00 |
| B. SM, 50 ug | 6 | 19.2 | 1.8 ml | 48 h | 1.48E+00 |
| | 9 | 18.6 | 1.7 ml | | 2.07E+00 |
| | 10 | 19.6 | 1.7 ml | | 5.70E+00 |
| B. SM, 50 ug | 1 | 19.4 | 1.8 ml, slow recovery | 4 wk | 1.48 |
| | 2 | 18.5 | 1.8 ml, B | | 2.07 |
| | 7 | 18.3 | 1.8 ml | | 5.70 |
| C. PTM, 75 ug | 11 | 22.1 | 1.8 ml, B | 48 h | 1.89E+00 |
| | 12 | 19.7 | 1.7 ml, Brett tried, Jun completed | | 9.42E+01 |
| | 13 | 21.8 | 1.8 ml, B | | |
| | 15 | 16.9 | 1.6 ml | | 1.35E+03 |
| | 16 | 20.2 | 1.8 ml | | 1.29E+02 |

TABLE 1-continued

Trans-splicing in mice - qRT-PCR Results

| Group | Mouse ID | Weight | Injection remarks | time | nor-TS |
|---|---|---|---|---|---|
| C. PTM, 75 ug | 17 | 18.3 | 1 ml | 1 wk | 2.18 |
|  | 18 | 18.5 | 1.8 ml, B |  | 1.09 |
|  | 19 | 18.6 | 1.6 ml |  | 31.50 |
|  | 20 | 20.1 | 1.7 ml |  | 188.71 |
|  | 25 | 20.9 | 1.8 ml |  | 44.55 |
| C. PTM, 75 ug | 21 | 18.9 | 1.7 ml | 2 wk | 47.84 |
|  | 22 | 17.4 | 1.6 ml |  | 64.03 |
|  | 23 | 19.9 | 1.7 ml |  |  |
|  | 24 | 20.1 | 1.7 ml, B several attemps |  | 1.40 |
|  | 28 | 18.6 | 1.7 ml, B |  |  |
| C. PTM, 75 ug | 26 | 18.2 | 1.7 ml, B | 4 wk | 0.19 |
|  | 27 | 19.6 | 1.7 ml |  | 25.92 |
|  | 29 | 21.3 | 1.8 ml, B |  | 1.33 |
|  | 30 | 16.5 | 1.5 ml |  | 3.93 |
|  | 35 | 19.4 | 1.7 ml |  | 7.25 |
| D. mAlb-hAI cDNA, 50 ug | 42 | 18.9 | 1.7 ml | 48 h | 1.53E+05 |
|  | 43 | 18.4 | 1.7 ml, B |  | 1.25E+05 |
|  | 44 | 15.4 | 1.5 ml |  | 8.56E+05 |
|  | 46 | 20.2 | 1.8 ml, B | 4 wk | 9.2E+03 |
|  | 47 | 22.2 | 1.8 ml, B 3 hrs later |  | 4.6E+03 |
|  | 48 | 18.1 | 1.7 ml |  | 9.8E+01 |

Western blot analysis of serum samples from mice injected with minicircles encoding the PTM confirmed the production of human apoAI protein through trans-splicing. Ten to fifty micro liter serum samples were immunoprecipitated using human specific apoAI antibody. After elution, samples were concentrated, analyzed on a 12% SDS-PAGE and probed with the same antibody (human specific apoAI antibody) that was used for immunoprecipitation. The blot was developed using an ECL kit (Invitrogen, Cat # WB7104). Western results clearly showed the presence of a 28 kDa protein band that co-migrated with the positive control purified apoAI protein (FIG. 45A). The presence of human apoAI protein was also detected in 4 week serum samples (FIG. 45B). These results not only confirmed the production of human apoAI protein through trans-splicing of PTM into endogenous mouse albumin pre-mRNA target in mice, but also demonstrated the utility of minicircles as a non-viral PTM delivery system.

13 EXAMPLE

In Vivo Trans-Splicing of Human ApoAI PTM into Mouse Albumin Pre-mRNA Increases High-Density Lipoprotein (HDL)

One of the main objectives of the current study is to determine whether production of human apoAI protein through trans-splicing contributes to HDL increase in vivo. To test this, mice were injected with mouse albumin PTM (PTM only) and control cDNA plasmid (mimics trans-spliced mRNA), as described above. Serum samples were collected at different time points (48 hrs through 4 weeks) and total HDL-cholesterol was determined by dextran sulfate precipitation method and the results were compared with controls. Specifically, 12 µl of serum was mixed with 4 µl dextran sulfate precipitation reagent plus 30 µl saline and, after 10 min at room temperature, was centrifuged for 30 min (4° C.) at 12,000 rpm. The clear supernatant (40 µl) was mixed with 169 µl saline and total cholesterol was measured using FPLC. The baseline total HDL-cholesterol in the control group averaged to about 60 mg/dL. At 48 hrs time point, ~25% increase in total HDL-cholesterol was observed in the control cDNA group that expresses an mRNA that is identical to trans-spliced mRNA. In contrast, no significant increase was observed in the PTM group at 48 hrs. However, as shown in FIG. 46, significant increases (25-50%) in total HDL-cholesterol was observed in serum samples collected at 1, 2 and 4 week time points in mice treated with PTM only and also mice treated with cDNA. Accordingly, the results presented in this application clearly show: (a) successful and accurate trans-splicing of mouse albumin PTM into mouse albumin target pre-mRNA, (b) production of human apoAI protein through trans-splicing and, most importantly, (c) production of human apoAI protein through trans-splicing in mice leads to significant (25-50%) increase in HDL level over the baseline. Increases in HDL blood levels are associated with reduced risk of cardiovascular disease. Numerous reports have indicated that "increasing the HDL cholesterol level by 1 mg may reduce cardiovascular risk by 2-3 percent (Castelli W P. Cholesterol and lipids in the risk of coronary artery disease—the Framingham Study. Can J Cardiol 1988; 4 [Suppl A]:5-10A; Third Report of the National Cholesterol Education Program [NCEP] Expert Panel on Detection, Evaluation and Treatment of High Blood Cholesterol in Adults [Adult Treatment Panel III]. Final Report. Bethesda [Md.]: National Cholesterol Education Program, National Heart, Lung, and Blood Institute, National Institutes of Health; September 2002. NIH Publication 02-5215. Brewer B H, 2004, *Am Heart J,* 148, S14-S18; Brewer B H, 2004, *N Engl J Med,* 350, 1491-1494)

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

We claim:

1. A cell comprising a nucleic acid molecule wherein said nucleic acid molecule comprises:
   (a) one or more target binding domains that target binding of the nucleic acid molecule to a target pre-mRNA expressed within the cell, wherein said target binding domain targets a human albumin pre-mRNA target of the cell genome;
   (b) a 3' splice region comprising a branch point and a 3' splice acceptor site;
   (c) a spacer region that separates the 3' splice region from the target binding domain; and
   (d) a nucleotide sequence to be trans-spliced to the target pre-mRNA wherein said nucleotide sequence encodes an apoAI polypeptide;
   wherein said nucleic acid molecule is recognized by nuclear splicing components within the cell.

2. A cell comprising a nucleic acid molecule wherein said nucleic acid molecule comprises:
   (a) one or more target binding domains that target binding of the nucleic acid molecule to a target pre-mRNA expressed within the cell, wherein said target binding domain targets a human albumin pre-mRNA target of the cell genome;
   (b) a 3' splice acceptor site;
   (c) a spacer region that separates the 3' splice region from the target binding domain; and
   (d) a nucleotide sequence to be trans-spliced to the target pre-mRNA wherein said nucleotide sequence encodes an apoAI polypeptide;
   wherein said nucleic acid molecule is recognized by nuclear splicing components within the cell.

3. A cell comprising a nucleic acid molecule wherein said nucleic acid molecule comprises:
   (a) one or more target binding domains that target binding of the nucleic acid molecule to a target pre-mRNA expressed within the cell, wherein said target binding domain targets a human albumin pre-mRNA target of the cell genome;
   (b) a 5' splice site;
   (c) a spacer region that separates the 5' splice site from the target binding domain; and
   (d) a nucleotide sequence to be trans-spliced to the target pre-mRNA wherein said nucleotide sequence encodes an apoAI polypeptide;
   wherein said nucleic acid molecule is recognized by nuclear splicing components within the cell.

4. The cell of claim 1 wherein the nucleic acid molecule further comprises a 5' donor site.

5. The cell of claim 1 wherein the 3' splice region further comprises a pyrimidine tract.

6. The cell of claim 1, 2 or 3 wherein said nucleic acid molecule further comprises a safety sequence comprising one or more complementary sequences that bind to one or both sides of the 5' splice site.

7. The cell of claim 1, 2 or 3 wherein the apoAI polypeptide is a pre-pro-apoAI.

8. The cell of claim 1, 2 or 3 wherein the cell is a hepatocyte.

9. The cell of claim 1, 2 or 3 wherein the nucleic acid molecule further comprises a safety nucleotide sequence comprising one or more complementary sequences that bind to one or more sides of the 3' splice region.

10. A cell comprising a recombinant vector wherein said vector expresses a nucleic acid molecule comprising:
    (a) one or more target binding domains that target binding of the nucleic acid molecule to a target pre-mRNA expressed within the cell, wherein said target binding domain targets a human albumin pre-mRNA target of the cell genome;
    (b) a 3' splice region comprising a branch point and a 3' splice acceptor site;
    (c) a spacer region that separates the 3' splice region from the target binding domain; and
    (d) a nucleotide sequence to be trans-spliced to the target pre-mRNA wherein said nucleotide sequence encodes an apoAI polypeptide
    wherein said nucleic acid molecule is recognized by nuclear splicing components within the cell.

11. A cell comprising a recombinant vector wherein said vector expresses a nucleic acid molecule comprising:
    (a) one or more target binding domains that target binding of the nucleic acid molecule to a target pre-mRNA expressed within the cell, wherein said target binding domain targets a human albumin pre-mRNA target of the cell genome;
    (b) a 3' splice acceptor site;
    (c) a spacer region that separates the 3' splice region from the target binding domain; and
    (d) a nucleotide sequence to be trans-spliced to the target pre-mRNA wherein said nucleotide sequence encodes an apoAI polypeptide;
    wherein said nucleic acid molecule is recognized by nuclear splicing components within the cell.

12. A cell comprising a recombinant vector wherein said vector expresses a nucleic acid molecule comprising:
    (a) one or more target binding domains that target binding of the nucleic acid molecule to a target pre-mRNA expressed within the cell, wherein said target binding domain targets a human albumin pre-mRNA target of the cell genome;
    (b) a 5' splice site;
    (c) a spacer region that separates the 5' splice site from the target binding domain; and
    (d) a nucleotide sequence to be trans-spliced to the target pre-mRNA wherein said nucleotide sequence encodes an apoAI polypeptide;
    wherein said nucleic acid molecule is recognized by nuclear splicing components within the cell.

13. The cell of claim 10 wherein the nucleic acid molecule further comprises a 5' donor site.

14. The cell of claim 10 wherein the 3' splice region further comprises a pyrimidine tract.

15. The cell of claim 10, 11 or 12 wherein the nucleic acid molecule further comprises a safety nucleotide sequence comprising one or more complementary sequences that bind to one or more sides of the 3' splice region.

16. The cell of claim 10, 11 or 12 wherein the apoAI polypeptide is a pre-pro-apoAI.

17. The cell of claim 10, 11 or 12 wherein the cell is a hepatocyte.

18. A method of producing a chimeric RNA molecule in a cell comprising:
   contacting a target pre-mRNA expressed in the cell with a nucleic acid molecule recognized by nuclear splicing components wherein said nucleic acid molecule comprises:
   (a) one or more target binding domains that target binding of the nucleic acid molecule to a target pre-mRNA expressed within the cell, wherein said target binding domain targets a human albumin pre-mRNA target of the cell genome;
   (b) a 3' splice region comprising a branch point and a 3' splice acceptor site;
   (c) a spacer region that separates the 3' splice region from the target binding domain; and
   (d) a nucleotide sequence to be trans-spliced to the target pre-mRNA wherein said nucleotide sequence encodes an apoAI polypeptide;
   under conditions in which a portion of the nucleic acid molecule is trans-spliced to a portion of the target pre-mRNA to form a chimeric RNA within the cell.

19. A method of producing a chimeric RNA molecule in a cell comprising:
   contacting target pre-mRNAs expressed in the cell with a nucleic acid molecule recognized by nuclear splicing components wherein said nucleic acid molecule comprises:
   (a) one or more target binding domains that target binding of the nucleic acid molecule to target pre-mRNA expressed within the cell, wherein said target binding domain targets a human albumin pre-mRNA target of the cell genome;
   (b) a 3' splice acceptor site;
   (c) a spacer region that separates the 3' splice region from the target binding domain; and
   (d) a nucleotide sequence to be trans-spliced to the target pre-mRNA wherein said nucleotide sequence encodes an apoAI polypeptide;
   under conditions in which a portion of the nucleic acid molecule is trans-spliced to a portion of the target pre-mRNA to form a chimeric RNA within the cell.

20. A method of producing a chimeric RNA molecule in a cell comprising:
   contacting a target pre-mRNA expressed within the cell with a nucleic acid molecule recognized by nuclear splicing components wherein said nucleic acid molecule comprises:
   (a) one or more target binding domains that target binding of the nucleic acid molecule to target pre-mRNA expressed within the cell, wherein said target binding domain targets a human albumin pre-mRNA target of the cell genome;
   (b) a 5' splice site;
   (c) a spacer region that separates the 5' splice site from the target binding domain; and
   (d) a nucleotide sequence to be trans-spliced to the target pre-mRNA wherein said nucleotide sequence encodes an apoAI polypeptide;
   wherein said nucleic acid molecule is recognized by nuclear splicing components within the cell.

21. The method of claim 18 wherein the nucleic acid molecule further comprises a 5' donor site.

22. The method of claim 18 wherein the 3' splice region further comprises a pyrimidine tract.

23. The method of claim 18, 19 or 20 wherein the nucleic acid molecule further comprises a safety nucleotide sequence comprising one or more complementary sequences that bind to one or more sides of the 3' splice region.

24. The method of claim 18, 19 or 20 wherein the apoAI polypeptide is a pre-proapoAI.

25. The method of claim 18, 19 or 20 wherein the cell is a hepatocyte.

* * * * *